United States Patent [19]

Ruesch

[11] Patent Number: 4,872,351
[45] Date of Patent: Oct. 10, 1989

[54] NET OIL COMPUTER

[75] Inventor: James R. Ruesch, Boulder, Colo.

[73] Assignee: Micro Motion Incorporated, Boulder, Colo.

[21] Appl. No.: 339,128

[22] Filed: Apr. 14, 1989

Related U.S. Application Data

[63] Continuation of Ser. No. 235,234, Aug. 23, 1988, abandoned, which is a continuation of Ser. No. 916,780, Oct. 9, 1986, abandoned.

[51] Int. Cl.$^4$ .............................................. G01F 1/74
[52] U.S. Cl. .................................................. 73/861.04
[58] Field of Search ............... 73/861.04, 32 A, 861.35

[56] References Cited

U.S. PATENT DOCUMENTS 4,689,989  9/1987  Aslesen et al. ................... 73/861.04

Primary Examiner—Michael J. Tokar
Assistant Examiner—Robert P. Bell
Attorney, Agent, or Firm—Peter L. Michaelson

[57] ABSTRACT

Apparatus and accompanying methods for implementing both an accurate densimeter and a net oil computer utilizing a common Coriolis meter assembly is described. In essence, this apparatus measures density of an unknown fluid by first determining the period at which both flow tubes contained within a dual tube Coriolis meter oscillate while the unknown fluid passes therethrough. This apparatus then squares the result. Thereafter, the density of the unknown fluid is determined as a linear function that relates the squared tube period measurement for the unknown fluid, and squared tube period measurements and known density values for two known fluids, such as air and water, that have previously and successively passed through the meter during calibration. When used as a net oil computer, the inventive system obtains mass flow and temperature measurements from the same flow tubes. By using measured density and mass flow values of an oil-water emulsion that flows through the same Coriolis meter, the inventive system can advantageously provide both volumetric and mass based measurements of the flow rate and totalized flow of the entire emulsion and of the individual water and oil components present therein.

36 Claims, 27 Drawing Sheets

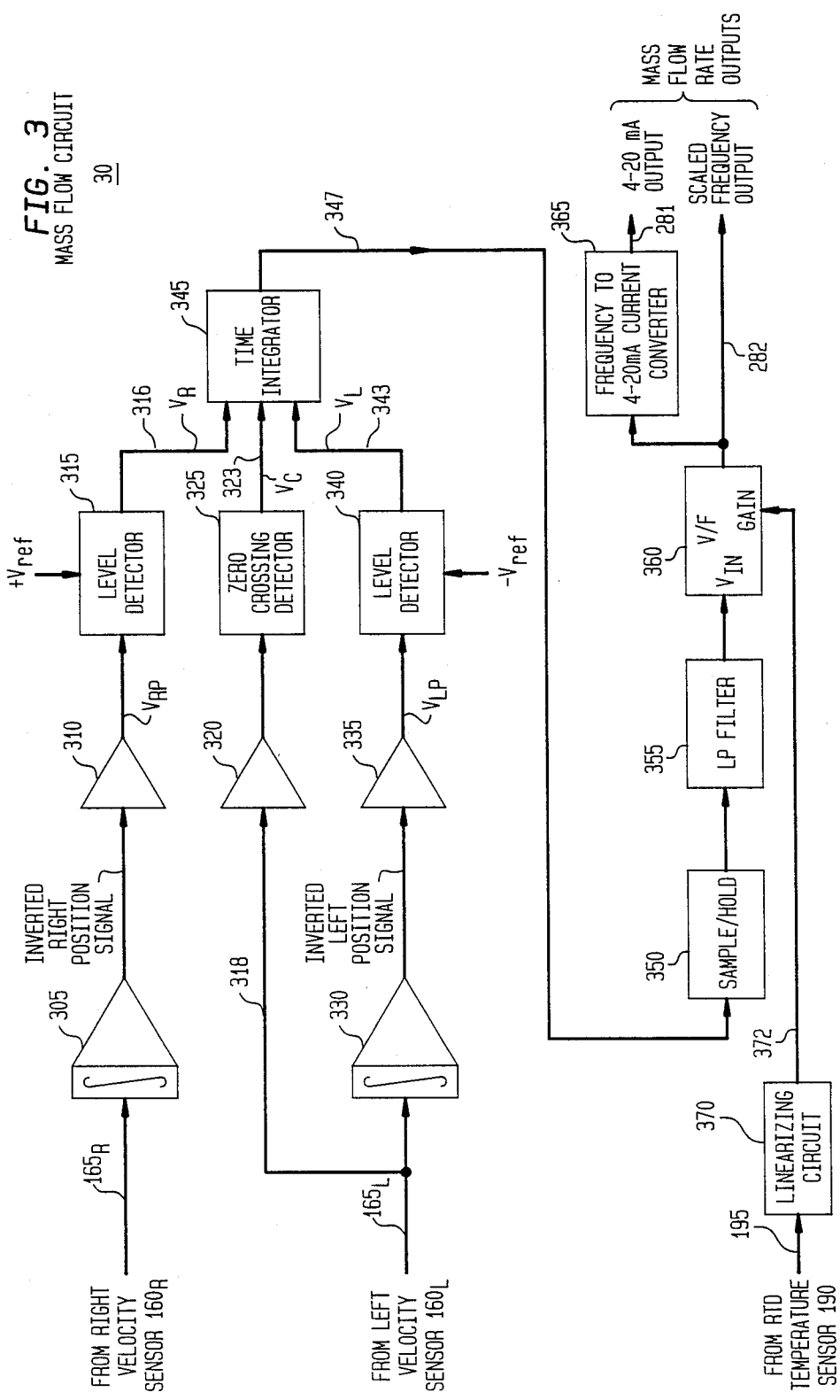

FLOW (POSITIVE DIRECTION)

FLOW TUBE DRIVE CIRCUIT

TUBE PERIOD INTERRUPT ROUTINE 800

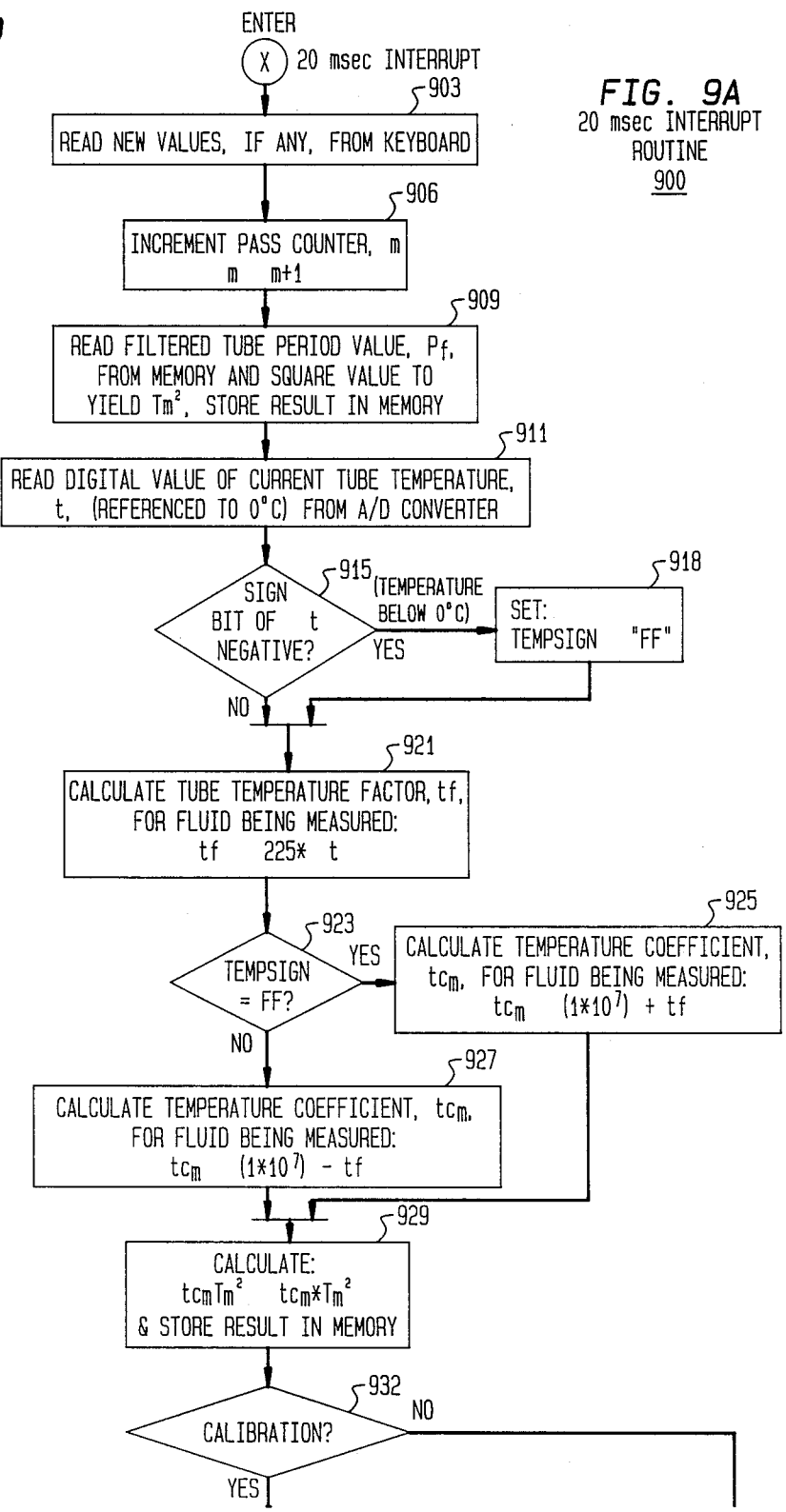

DRT PARAMETER
CALCULATION AND
TRANSMISSION ROUTINE
1000

| FIG. 11A |
| FIG. 11B |
| FIG. 11C |

TEMPERATURE COMPENSATED OIL DENSITY ROUTINE 1100

| FIG. 12A |
| FIG. 12B |

TEMPERATURE COMPENSATED WATER DENSITY ROUTINE 1200

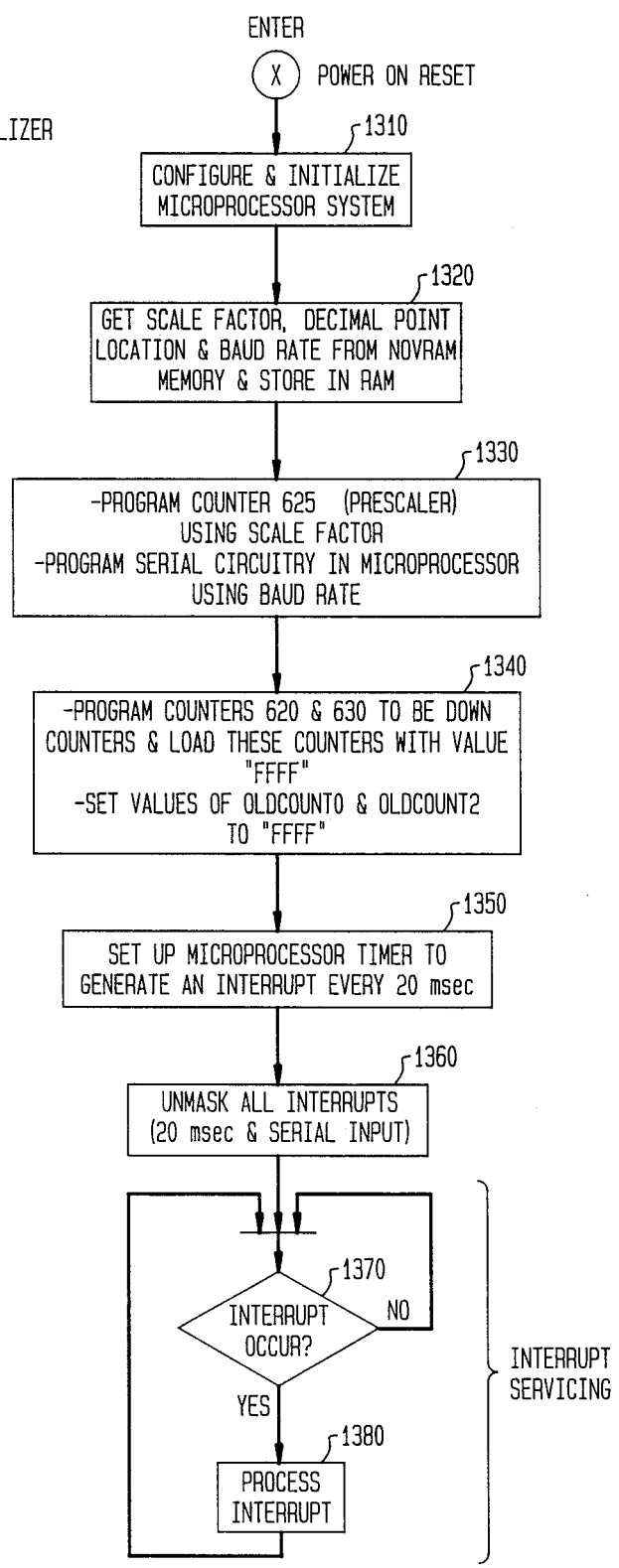

SERIAL INPUT
INTERRUPT ROUTINE 1400

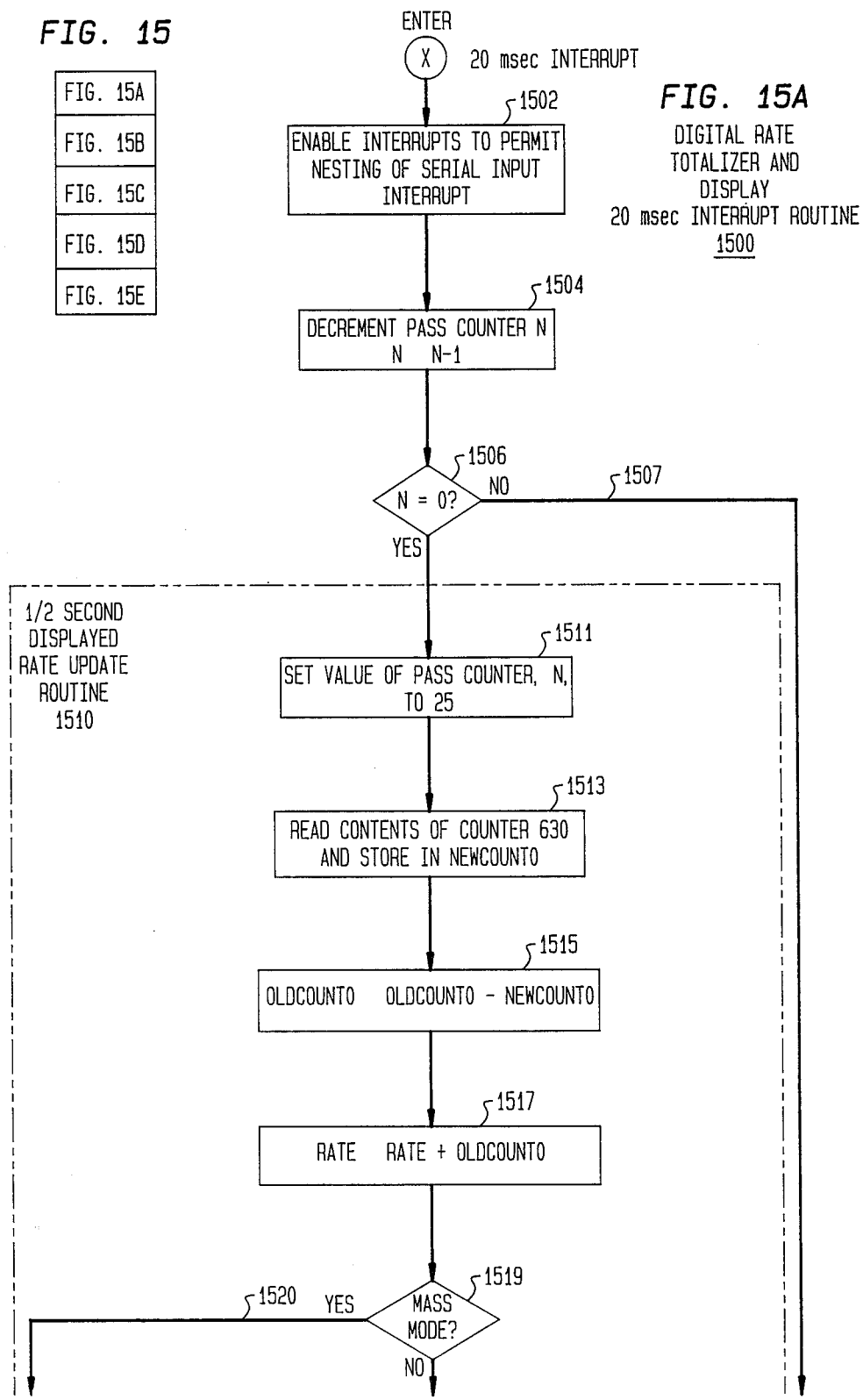

NET OIL COMPUTER

CROSS REFERENCE TO RELATED APPLICATION

The reader is referred to my co-pending United States patent application entitled "APPARATUS AND METHODS FOR MEASURING THE DENSITY OF AN UNKNOWN FLUID USING CORIOLIS METER", Ser. No. 06/916,973, filed Oct. 19, 1989 now abandoned has been assigned to the present assignee and which claims subject matter described herein.

This application is a continuation of my co-pending patent application Ser. No. 07/235,234, filed Aug. 28, 1988, and entitled "NET OIL COMPUTER," which is a continuation of my patent application Ser. No. 06/916,780, filed Oct. 9, 1986, now abandoned.

BACKGROUND OF THE INVENTION

1. Field of the Invention

The present invention relates to apparatus and accompanying methods for implementing both an accurate densimeter and a net oil computer utilizing a common Coriolis mass flow rate meter.

2. Description of the Prior Art

Very often, the need arises to measure the density of a process fluid. This can be seen in two different examples. First, in the food industry, liquid sucrose is frequently used as a sweetening agent in a food sweetener. To provide an acceptably sweet taste, the amount of sucrose appearing in tho sweetener, and hence the density of the sweetener, must fall within a prescribed range. Therefore, manufacturers must constantly measure the density of the sweetener as it is being manufactured and accordingly adjust various process parameters to ensure that the sweetener contains sufficient sucrose to produce the proper taste. Second, in the petroleum industry, the lubricating ability of oil is related to its density which changes with temperature. Thus, to ensure that a quantity of oil will provide proper lubrication in a given application, the density of the oil must be known before the oil is placed into service. Therefore, during the oil refining process, the density of refined oil is first measured, and then, once known, is visibly marked on its container in terms of a range, e.g. 10W30, situated within a scale established by the American Petroleum Institute (API).

Coriolis mass flow meters can be used to measure density of an unknown process fluid. In general, as taught, for example, in U.S. Pat. No. 4,491,025 (issued to J. E. Smith et. al. on Jan. 1, 1985), a Coriolis meter can contain two parallel conduits, each typically being a U-shaped flow tube. Each flow tube is driven such that it oscillates about an axis. As the process fluid flows through each oscillating flow tube, movement of the fluid produces reactionary Coriolis forces that are perpendicularly oriented to both the velocity of the fluid and the angular velocity of tube. These reactionary Coriolis forces cause each tube to twist about a torsional axis that with U-shaped flow tubes is normal to its binding axis. Both tubes are oppositely driven such that each tube behaves as a separate tine of a tuning fork and thereby advantageously cancels any undesirable vibrations that might otherwise mask the Coriolis forces. The resonant frequency at which each flow tube oscillates depends upon its total mass, i.e. the mass of the empty tube itself plus the mass of the fluid flowing therethrough. Inasmuch as the total mass will vary as the density of the fluid flowing through the tube varies, the resonant frequency will likewise vary with any changes in density.

Now, as specifically taught in my U.S. Pat. No. 4,491,000 (issued Jan. 1, 1985 to the same assignee as the present application and hereinafter referred to as the '009 patent), the density of an unknown fluid flowing through an oscillating flow tube is proportional to the square of the period at which the tube resonates. In the '009 patent, I described an analog circuit that computes density through use of two serially connected integrators. A reference voltage is applied to the first integrator. Inasmuch as the spring constant of each flow tube varies with temperature and thereby changes the resonant frequency, the reference voltage is appropriately compensated for temperature variations of the tube. Both integrators operate for a period of time equivalent to the square of the resonant period. In this manner, the output signal generated by the analog circuit provides a product of a temperature dependent function and the square of the value of the resonant period. With appropriate scaling of the reference voltage, the output analog signal provides a direct readout of the density measurements (in specific gravity units) of the unknown fluid that flows through the flow tube.

While this circuit provides accurate density measurements unfortunately it possesses several drawbacks. First, for certain applications, density measurements to an accuracy of one part in 10,000 are necessary. An accuracy of this magnitude is generally not available through an analog circuit unless highly precise analog components are used. Such components are disadvantageously quite expensive. Second, the analog circuit disclosed in the '009 patent can not be independently calibrated to compensate for changing characteristics of the electronic components—such as offset, drift, aging and the like. Specifically, this circuit is calibrated on a "lumped" basis, i.e. by first passing a known fluid, such as water, through the meter and then adjusting the circuit to provide the proper density reading at its output. This process compensates for any errors that occur at the time of calibration that are attributable either to physical (empirical) errors in measuring density using a Coriolis mass flow meter or to errors generated by the changing characteristics of the electrical components themselves. Unfortunately, after the circuit has been calibrated in this fashion, component characteristics will subsequently change over time and thereby inject errors into the density readings produced by the circuit. This, in turn, will eventually necessitate an entire recalibration. Third, it is often desirable in many applications to provide density measurements in units other than specific gravity units, e.g. % sucrose (or "brix") for the food industry; API units and/or pounds/barrel for the oil industry; and % solids, grams/cubic centimeter (cc), kilograms/cubic meter, pounds/gallon, pounds/cubic foot, or the like for other industries. Although an analog density signal can be readily scaled to other units, doing so often necessitates the use of customized circuitry with accompanying added expense.

In addition, many currently available densimeters do not provide density measurements based upon the full stream of a process fluid that flows through a process line and thus, in many applications, provide inaccurate density measurements of the fluid. Specifically, these meters disadvantageously utilize flow tubes that have a rather small diameter. Consequently, if such a meter is used to measure the density of a fluid flowing through a rather large line, then the line is tapped and a small portion of the fluid in the line is diverted from the line, in what is commonly referred to as a "side stream", and routed through the meter. Oftentimes, the fluid flowing in the side stream does not accurately represent the entire process fluid flowing through the line. For example, in certain applications, the process fluid may be a slurry containing relatively light liquid matter and relatively heavy solid matter. The solid matter, being denser than the liquid matter, will tend to flow along the bottom of the fluid stream with the liquid matter flowing immediately above. As a result, the side stream, depending where the line has been tapped along its cross-section, may contain a greater percentage of the liquid over the solid matter than that which occurs in the slurry that actually flows through the line. Some densimeter manufacturers claim that if the tap is taken along the middle of the line, then the density of the side stream will accurately represent the average density of the slurry hen flowing through the line. In practice, the actual percentage of solids that constitutes the slurry will dictate whether the density of the side stream, taken along the midpoint of the line, truly represents the density of the entire process fluid. Inasmuch as this percentage rarely equals 50%, this claim is generally not true. Consequently, in many applications, erroneous density measurements are produced by those meters that rely on measuring the density of the process fluid that flows in a side stream.

Moreover, all densimeters need to be calibrated using a fluid (a calibration fluid) having a known density. This density is specified at a certain temperature. Unfortunately, the density of most fluids varies with temperature: some fluids exhibit a significant variation, while other fluids exhibit relatively little variation. Consequently, many currently available densimeters require that the temperature of the calibration fluid must be carefully controlled before the fluid is injected into the densimeter for calibration. First, this necessitates that the container holding the fluid must be placed in a temperature bath for a sufficiently long period of time so that the fluid will stabilize to a desired temperature. Second, provisions must ba made to ensure that the temperature of the fluid will not change as the fluid is pumped through the meter. Accurately controlling the temperature of a fluid and then accurately maintaining its temperature, while the fluid is being pumped through the meter, is both a costly and tedious process.

Furthermore, as one can appreciate, density measurements also find particular utility in ascertaining the percentage and volumetric measure of each of two immiscible substances flowing in a two component flow stream (emulsion). One common use involves determining the amount of oil that occurs in an oil-water stream flowing through a pipeline. Specifically, saltwater often co-exists with crude oil in a common geologic formation. As such, both substances are often pumped up together by a working oil well and simultaneously travel through piping to a downstream location at which the saltwater is ultimately separated from the crude oil. To accurately determine the amount of crude oil traveling through the pipe, well operators utilize a "net oil computer" to ascertain the amount of crude oil, on a percentage and volumetric basis of the total oil-water flow stream, that emanates from the well Net oil computers often utilize density measurements in calculating the percentage and volumetric measure of crude oil. Given the large quantities of crude oil that are usually involved, any small inaccuracies in measuring density can disadvantageously accumulate, over a relatively short interval of time, to a large error in a totalized volumetric measure. Unfortunately, many presently available densimeters do not provide a sufficiently accurate density reading, to one part in 10,000 as noted above, to yield a relatively large totalized volumetric measurement with an acceptably low error.

Therefore, a need exists in the art for a densimeter which is accurate to at least one part in 10,000; which uses relatively inexpensive components; which substantially eliminates any error caused by changing characteristics of any of the electronic components; which provides easy conversion of density measurements from specific gravity units to any other unit, and which does not measure density using a side stream or require the use of a temperature controlled calibration fluid.

SUMMARY OF THE INVENTION

Accordingly, an object of the present invention is to provide an accurate densimeter.

Another object is to provide such a densimeter which use relatively inexpensive components.

A further object is to provide such a densimeter that is relatively insensitive to changing component characteristics, such as drift, aging, offset and the like.

A further object is to provide such a densimeter that readily converts measured density readings into any other desired unit.

A further object is to provide such a densimeter which does not measure density through a side stream.

A further object is to provide such a densimeter which does not require the use of a temperature controlled calibration fluid.

Lastly an additional object is to provide an accurate net oil computer.

These and other objects are achieved in accordance with the principles of the present invention by a metering system that employs a common Coriolis mass flow rate meter to implement both an accurate densimeter and a net oil computer. In essence, this apparatus measures density of an unknown fluid by first determining the period at which one of two flow tubes contained within the Coriolis meter oscillates while the unknown fluid passes therethrough This apparatus then squares the result. Thereafter, the density of the unknown fluid is determined as a linear function of the squared tube period measurement for the unknown fluid, and squared tube period measurements and known density values for two known fluids, such as air and water, that have previously and successively passed through the meter during calibration The inventive system advantageously functions as a net oil computer by obtaining mass flow and temperature measurements from the same flow tubes. By using the measured density and mass flow values of an oil-water emulsion that flows through the same Coriolis meter, the inventive system provides volumetric measurements of the flow rate and totalized flow of the entire emulsion and of the individual water and oil components present therein.

In accordance with a specific embodiment of the invention, the inventive metering system contains a mass flow rate circuit, a densimeter processor and a digital rate totalizer and display circuit (DRT). The mass flow rate circuit determines tho mass flow rate of a fluid as it passes through two parallel vibrating flow tubes of the Coriolis meter. This circuit relies on using tube velocity information obtained from ferromagnetic velocity sensors attached to the tubes, and flow tube temperature obtained through a temperature sensor, such as an RTD, mounted to one of the flow tubes. The measured mass flow rate is provided as an output from the inventive system for connection to downstream process control equipment and is also applied, as an input, to the DRT.

The densimeter processor, which is a microprocessor based system, determines the density of this fluid as it passes through the flow tubes. To do so, the densimeter processor processes velocity information provided by one of the ferromagnetic sensors to determine the period at which the flow tubes vibrate. In addition, the densimeter processor has previously measured the tube periods and temperatures for two fluids, having known density values, that have successively passed through the flow tubes during meter calibration Based upon these past measurements obtained during calibration, the densimeter processor calculates density of the unknown fluid as a linear function relating the squared tube period measurement for the unknown fluid and the squared tube period measurements and known density values for the two known fluids. The assured density value is available as an output from the inventive system for connection to downstream process control equipment and, along with other parameters, is also serially supplied as an input to the DRT.

In applications where the inventive system is used as a net oil computer, the unknown fluid is a crude oil-saltwater emulsion that flows through the meter. As such, the density of the unknown fluid is that of the emulsion. In order for the inventive system to provide separate volumetric flow measurements of the oil and water components present in the emulsion, the densimeter processor first determines the density of the emulsion attributable to each component. This is accomplished using a user supplied reference density value for each component which is then compensated by the densimeter processor for the actual tube temperature as measured by the densimeter. Based upon these temperature compensated density values, the densimeter processor then calculates water cut and oil cut density ratios as well as a mass to volume conversion factor for the entire emulsion. The values of these ratios and the conversion factor are then transmitted serially by the densimeter processor to the DRT, which is itself a microprocessor system. The DRT utilizes the mass flow rate to provide totalized mass flow and then, using the mass to volume conversion factor supplied by the densimeter processor, calculates equivalent volumetric flow rate and totalized volumetric flow for the entire oil-water emulsion. Thereafter, the DRT utilizes the water cut and oil cut density ratios, also supplied by the densimeter processor, to separately calculate volumetric flow rates for the oil and water components. These separate volumetric flow rates are then totalized to generate a corresponding totalized volumetric flow value for each component.

In accordance with a feature of the invention, the inventive system, when used as a net oil computer, can also advantageously provide separate mass flow rate measurements of the oil and water components that constitute the oil-water emulsion, and totalized mass flow measurements for each component and for the entire emulsion. This is accomplished by appropriately modifying the density ratios calculated by the densimeter processor and supplied to the DRT The DRT then calculates the mass flow rate of each component in the emulsion using these modified ratios and thereafter separately totalizes these flow rates to generate a corresponding totalized mass flow value for each component.

BRIEF DESCRIPTION OF THE DRAWINGS

The teachings of the present invention may be clearly understood by considering the following detailed description in conjunction with the accompanying drawings in which:

FIG. 3 is a block diagram of Mass Flow Rate Circuit 30, shown in FIG. 2;

FIG. 9 is a diagram showing the correct alignment of the respective drawing sheets for FIGS. 9A-9D;

FIGS. 9A-9D collectively depict a flowchart cf msec Interrupt Routine 900 which is also executed by Densimeter Processor 50;

FIG. 13 depicts a flowchart of Main Program that is executed by DRT 60, shown in FIG. 6;

FIG. 15 is a diagram showing the correct alignment of the drawing sheets for FIGS. 15A-15E; and FIGS. 15A-15E collectively depict a flowchart of 20msec Interrupt Routine 1300 which is also executed by DRT 60.

To facilitate understanding, identical reference numerals have been used to denote identical elements common to the figures.

DETAILED DESCRIPTION

A. Overall System Description

Figure 1:
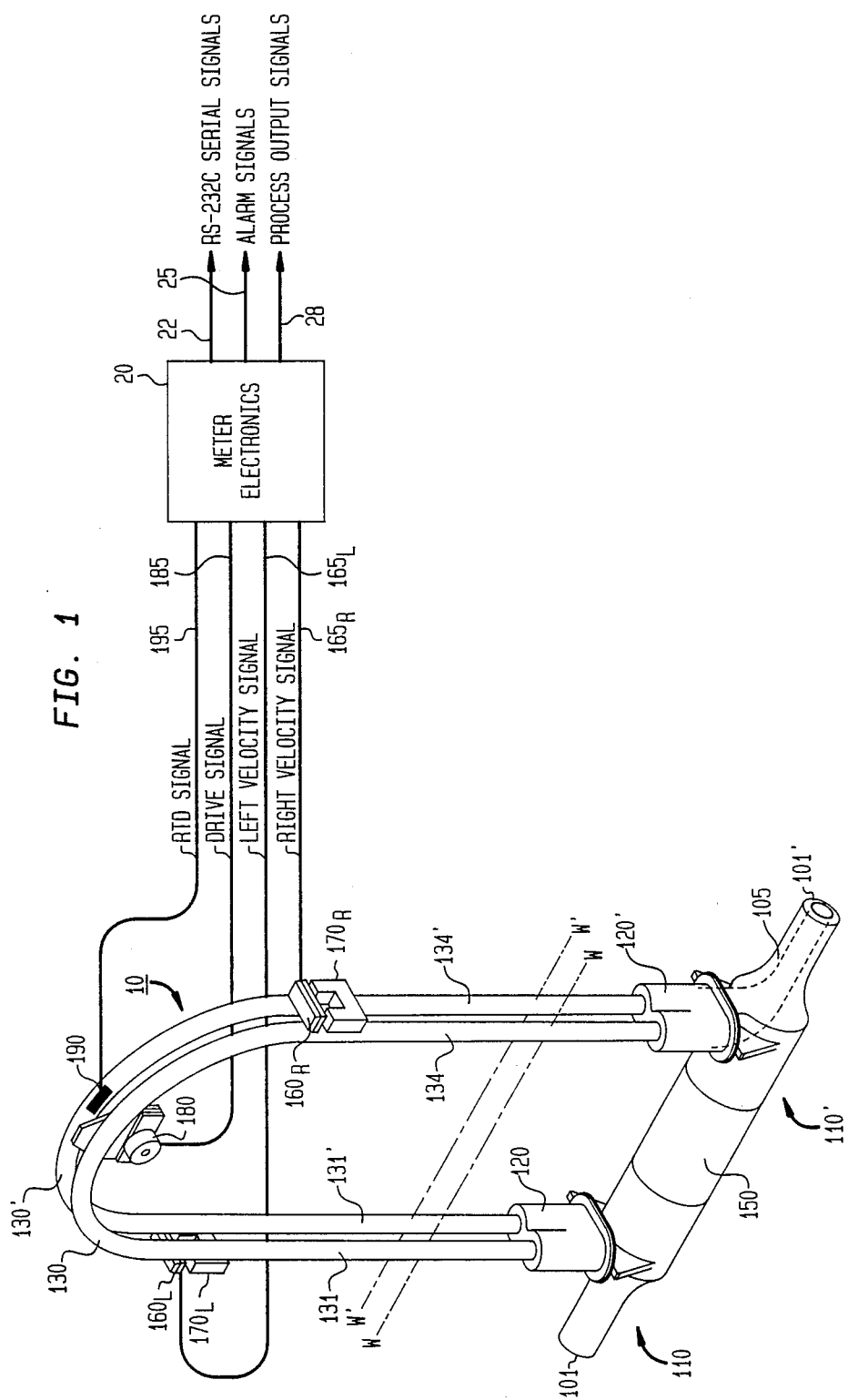
FIG. 1 is an overall diagram of a metering system which embodies the teachings of the present invention.

FIG. 1 shows an overall diagram of a metering system embodying the principles of the present invention. This system not only measures the density of an unknown fluid but also, when used to measure an oil-water flow stream, advantageously functions as a net oil computer.

Specifically, as shown, the system consists of two basic components: Coriolis meter assembly 10 and meter electronics 20. As shown, Coriolis meter assembly 10 includes a pair of manifolds 110 and 110'; tubular member 150; a pair of parallel flow tubes 130 and 130'; drive mechanism 180; a pair of velocity sensing coils $160_L$ and $160_R$; and a pair permanent magnets $170_L$ and $170_R$. Tubes 130 and 130' are substantially U-shaped and have their ends attached to tube mounting blocks 120 and 120', which are in turn secured to respective manifolds 110 and 110', Both flow tubes are free of pressure sensitive joints.

With the side legs of tubes 130 and 130' fixedly attached to tube mounting blocks 120 and 120' and these blocks, in turn, fixedly attached to manifolds 110 and 110', as shown in FIG. 1, a continuous closed fluid path is provided through Coriolis meter assembly 10. Specifically, when meter 10 is connected, via inlet end 101 and outlet end 101', into a conduit system (not fluid flowing shown) in which the density of a therethrough is to, be determined, fluid enters the meter through an orifice in inlet end 101 of manifold 110 and is conducted through a passageway therein having a gradually changing cross-section to tube mounting block 20. There, the fluid is divided and routed through flow tubes 130 and 130'. Upon exiting flow tubes 130 and 130', the fluid is recombined in a single stream within tube mounting block 120' and is thereafter routed to manifold 110'. Within manifold 110' the fluid flows through a passageway having a similar gradually changing cross-section to that of manifold 110—as shown by dotted lines 105—to an orifice in outlet end 101'. At end 101' the fluid reenters the conduit system. Tubular member 150 does not conduct any fluid. Instead, this member serves to axially align manifolds 110 and 110' and maintain the spacing therebetween by a pre-determined amount so that these manifolds will readily receive mounting blocks 120 and 120' and flow tubes 130 and 130'.

U-shaped flow tubes 130 and 130' are selected and mounted so as to have substantially the same moments of inertia and spring constants about bending axes W—W and W'-W', respectively. These bending axes are perpendicular to the side legs of the U-shaped flow tubes and are located near respective tube mounting blocks 120 and 120'. The U-shaped flow tubes extend outwardly from the mounting blocks in an essentially parallel fashion and have substantially equal moments of inertia and equal spring constants about their respective bending axes. Inasmuch as the spring constant of the tubes changes with temperature, resistive temperature detector (RTD) 190 equally a platinum RTD device is mounted to one of (typical the flow tubes, here tube 130', to continuously measure the temperature of the tube. The temperature of the tube and hence the voltage appearing across the RTD, for a given current passing therethrough, will be governed by the temperature of the fluid passing through the flow tube. The temperature dependent voltage appearing across the RTD is used, as discussed in detail later, by meter electronics 20 to appropriately compensate the value of the spring constant for any changes in tube temperature. The RTD is connected to meter electronics 20 by lead 195.

Figure 4:
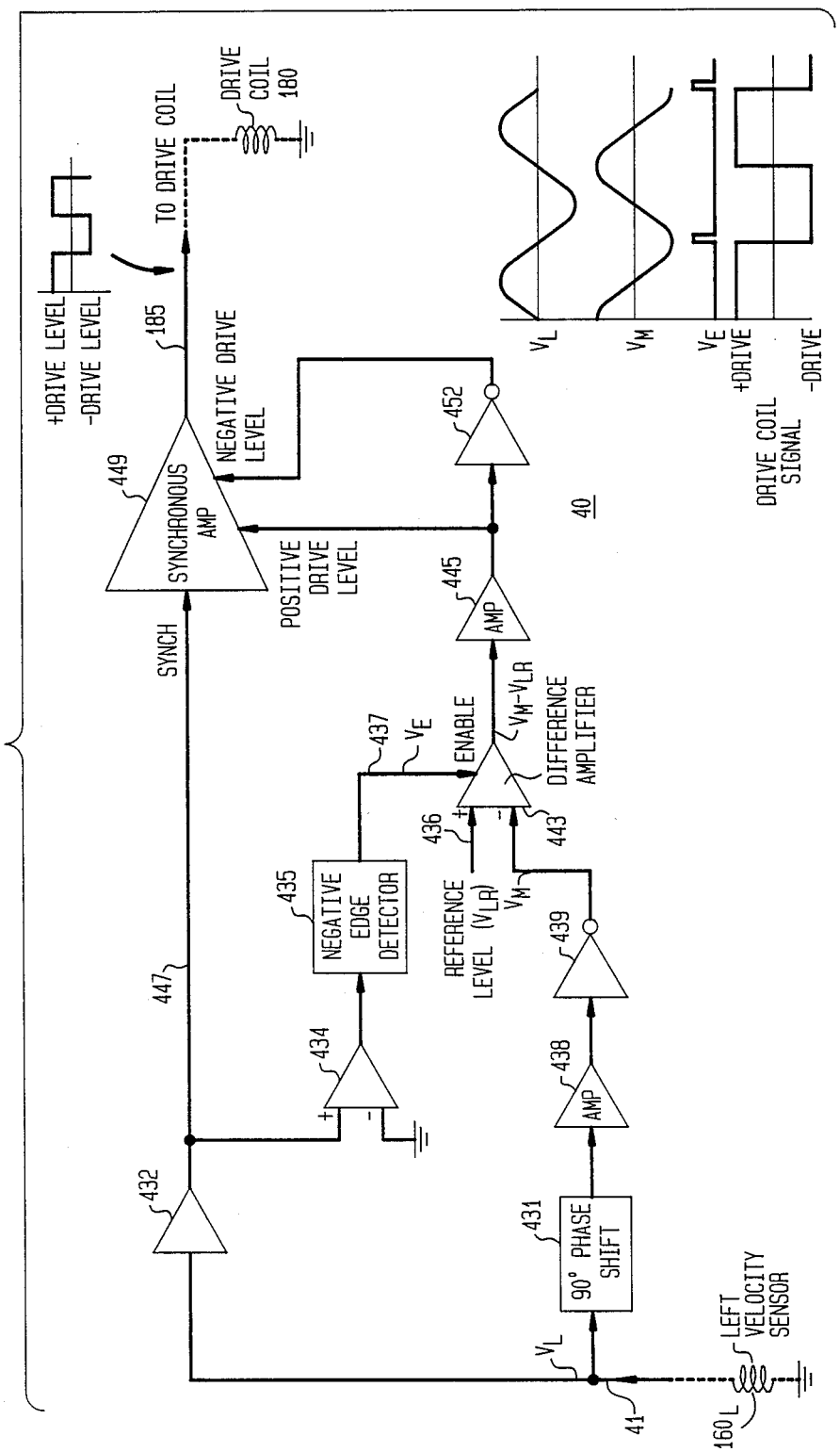
FIG. 4 is a block diagram of Flow Tuba Drive Circuit 40, also shown in FIG. 2.

Both of these flow tubes are sinusoidally driven in opposite directions about their respective bending axes and at essentially their common resonant frequency. In this manner, both flow tubes will vibrate in the same manner as do the tines of a tuning fork. Drive mechanism 180 supplies the sinusoidal oscillatory driving forces to tubes 130 and 130'. This drive mechanism can consist of any one of many well known arrangements, such as a magnet and a coil through which an alternating current is passed, for sinusoidally vibrating both flow tubes at a common frequency. A suitable oscillatory drive signal, as discussed in detail below in conjunction with FIG. 4, is applied by meter electronics 20, via lead 185, to drive mechanism 180.

As long as fluid flows through both tubes while these tubes are sinusoidally driven in opposite directions, Coriolis forces will be generated along adjacent side legs of each of flow tubes 130 and 130' but in opposite directions, i e. the Coriolis force generated in side leg 131 will oppose that generated in side leg 131'. This phenomenon occurs because although the fluid flows through the flow tubes in essentially the same parallel direction, the angular velocity vectors for the oscillating flow tubes are situated in opposite though essentially parallel directions. Accordingly, during one-half of the oscillation cycle of both flow tubes, side legs 131 and 131' will be twisted closer together than the minimum distance occurring between these legs produced by just the oscillatory movement of the tubes generated by drive mechanism 180. During the next half-cycle, the generated Coriolis forces will twist the side legs 131 and 131' further apart than the maximum distance occurring between these legs produced by just the oscillatory movement of the tubes generated by drive mechanism 180.

During oscillation of the tubes, the adjacent side legs, which are forced closer together than their counterpart side legs, will pass through the mid-planes of oscillation before their counterparts do The time interval which elapses from the instant one pair of adjacent side legs passes through its mid-plane of oscillation to the instant the counterpart pair of side legs, i.e., those forced further apart, passes through its respective mid-plane of oscillation is proportional to the total mass flow rate of the fluid flowing through meter assembly 10. The reader is referred to the U.S. Pat. No. 4,491,025 (issued to J. E. Smith et. al. on January , 1985) for a far more detailed discussion of the principles of operation of parallel path Coriolis flow meters than that just presented and, specifically, for the teaching that the mass flow rate can be determined from measurement of such time intervals.

To measure the time interval occurring between passage of the flow tube side-legs through their respective mid-planes of oscillation coils $160_L$ and $160_R$ are attached to either one of tubes 130 and 130' near their free ends and permanent magnets $170_L$ and $170_R$ are also attached near the free ends of the other one of the tubes. Magnets $170_L$ and $170_R$ are disposed so as to have coils $160_L$ and $160_R$ located in the volume surrounds the respective permanent magnets and in which the magnetic flux fields are essentially uniform. With this configuration, the electrical signal outputs generated by coils $160_L$ and $160_R$ provide a velocity profile of the complete travel of the tube and can be processed, as set forth in detail later, to determine the time interval and, in turn, the mass flow rate of the fluid passing through both tubes. In particular, coils $160_L$ and $160_R$ produce the left and right velocity signals that appear on leads $165_L$ and $165_R$ respectively. The fact that the midplane of oscillation is used as a timing reference point should not be considered as a limitation. Any predetermined point in the velocity signal can be used as the reference point for measuring the time interval that occurs between these two signals.

Furthermore, as taught in the art, such as in my U.S. Pat. No. 4,491,009 (issued on Jan. 1, 1985), the resonant frequency at which each flow tube will vibrate is a function of the square root of the spring constant of the tube divided by the total mass of the flow tube, i.e. the mass of the empty tube itself plus the mass of the fluid flowing therethrough. Inasmuch as the mass of the fluid flowing tough meter assembly 10 is directly proportional to the density of this fluid, then the density of this fluid is proportional to the square of the period at which the flow tube oscillates multiplied by the temperature dependent spring constant of the tube. Hence, by determining the period at which one of the flow tubes oscillates and by appropriately scaling the result, an accurate measure of the density of the fluid flowing through the tube can be obtained. The period is determined using the signal produced by one of the tube velocity sensors, illustratively left velocity signal appearing on lead $165_L$ produced by coil $160_L$.

As noted, meter electronics 20 accepts as input the RTD signal appearing on lead 195, and left and right velocity signals appearing on leads $165_L$ and $165_R$, respectively. Meter electronics 20 also produces, as noted, sinusoidal drive signal appearing on lead 185. The meter electronics, as explained below, processes the left velocity signal and the RTD temperature to determine the density of the fluid passing through meter assembly and also processes both velocity signals and the RTD signal to determine the mass flow rate of this fluid. This mass flow rate is provided by meter electronics 20 on leads 28 in analog form, illustratively 4–20 mA signals and frequency outputs for easy interfacing to other process control equipment, and in RS-232C serial form on serial communication lines 22. Contact closures are provided on leads 25 by meter electronics 20 to indicate various alarm conditions, such as, for example, if the measured mass flow rate either exceeds a predetermined maximum set-point or falls below a predetermined minimum set-point.

In addition, if the metering system is used to measure an oil-water flow stream (emulsion), meter electronics 20 advantageously functions as an accurate net oil computer. In particular, once the density and mass flow rate have been ascertained for this flow stream, meter electronics 20, in a manner set fort detail below, uses these two parameters to accurately and separately calculate the volumetric flow rate and totalized volumetric flow of the entire flow stream, and of the oil and water components that pass through meter assembly 10. This flow information is displayed, as is the fluid density and totalized mass flow rate of the entire flow stream, by the meter electronics.

Figure 2:
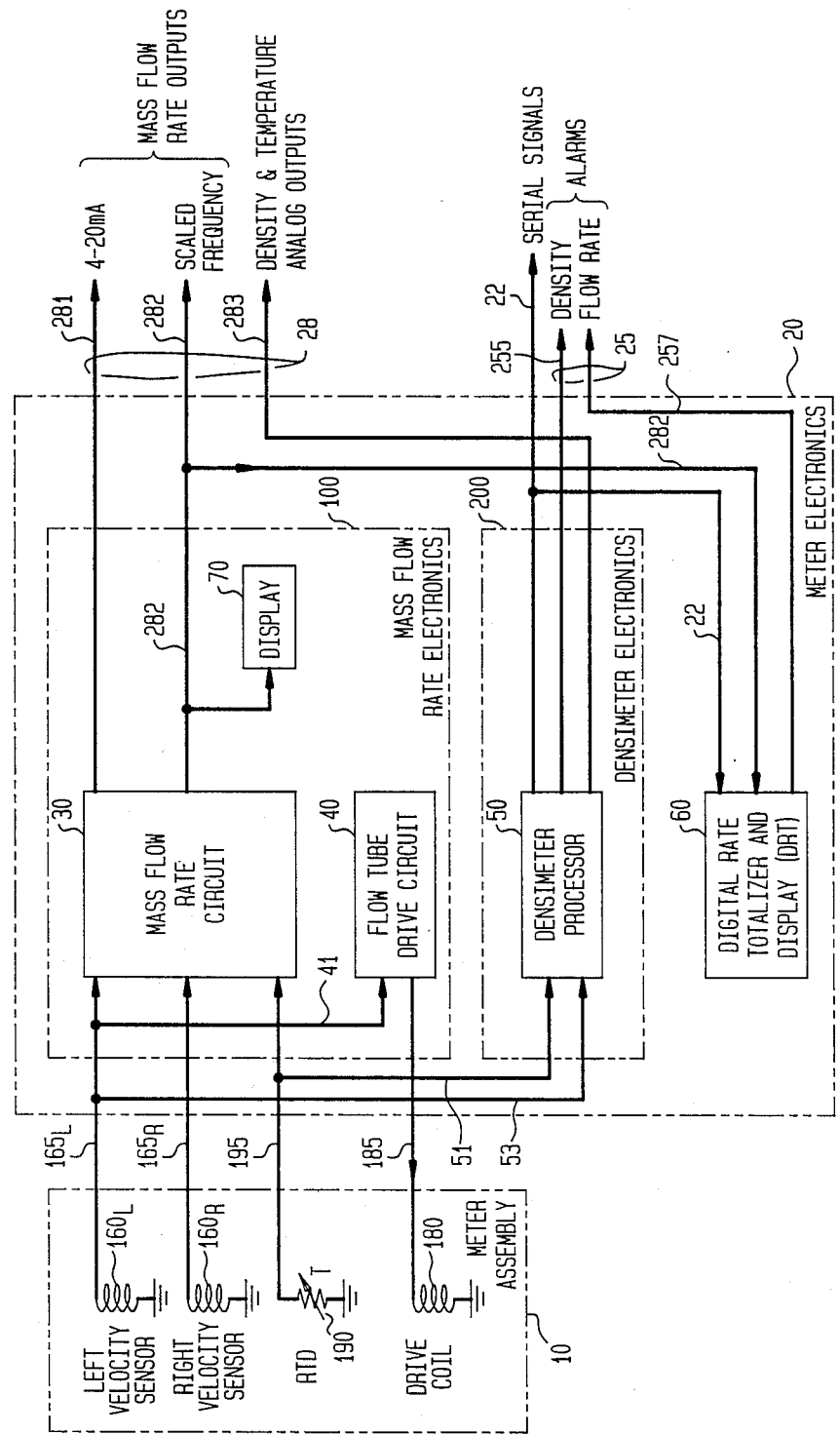
FIG. 2 is a block diagram of Meter Electronics 20 shown in FIG. 1.

A block diagram of meter electronics 20 is depicted in FIG. 2. Here, as shown, meter electric consists of mass flow rate electronics 100 which includes mass flow rate circuit 30, flow tube drive circuit 40 and display 70; densimeter electronics 200 which includes densimeter processor 50; and digital rate totalizer and display circuit (DRT) 60.

Mass flow rate circuit 30 processes the left and right velocity signals appearing over leads $165_L$ and $165_R$, respectively, along with the RTD signal appearing on lead 195, as explained in detail below in conjunction with FIG. 3, to determine the mass flow rate of the fluid passing through meter assembly 10. The resulting mass flow rate information is provided as a 4–20 mA output signal over lead 281, for easy connection to additional process control equipment, and as a scaled frequency signal over lead 282 for easy connection to a remote totalizer. The signals appearing on leads 281, 282 and 283 form the process signals that collectively appear on leads 28 shown in FIG. 1.

Flow tube drive circuit 40, depicted in FIG. 2 and as explained in detail in conjunction with FIG. 4, provides a square wave drive signal, via lead 185, to drive coil 180. This circuit synchronizes the square wave drive signal to the left velocity signal which appears on leads 165L and 41.

Figure 5:
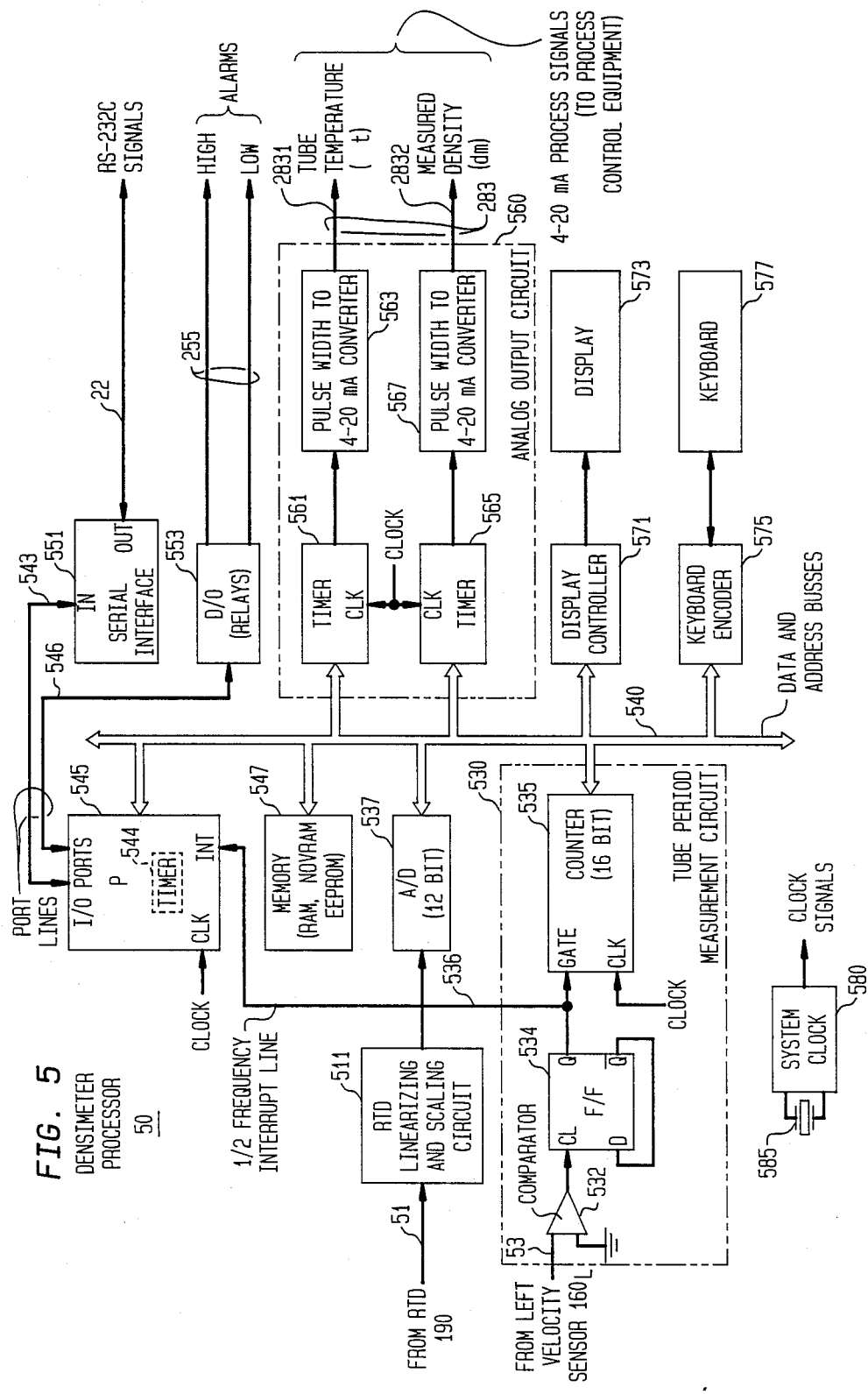
FIG. 5 is a block diagram of the hardware that constitutes Densimeter Processor 50, also shown in FIG.

Densimeter processor 50, in a manner explained in detail in conjunction With FIG. 5, processes the left velocity signal appearing on leads $165_L$ and 53 and the RTD signal appearing on leads 195 and 51 to determine the density of the fluid flowing through meter assembly 10. In essence, this apparatus measures density of an unknown fluid by first determining the period at which both flow tubes contained within the Coriolis meter oscillate while the unknown fluid passes therethrough. This apparatus then squares the result. Thereafter, the density of the unknown fluid is determined as a linear function that relates the squared tube period measurement for the unknown fluid, and squared tube period measurements and known density values for two known fluids, such as air and water, that have previously and successively passed through meter assembly 10 during calibration (as discussed in detail below). Measured density (dm) and tube temperature outputs (delta t, i.e. tube temperature referenced to 0 degrees C) are provided in serial RS-232C form over serial communication lines 22, and in analog 4–20 mA form over leads 283. High and low alarm contact closures are provided over leads 255.

Digital rate totalizer and display circuit DRT 60 provides volumetric flow rate and totalized volumetric flow measurements. To do this, DRT 60 receives measured mass flow rate measurements, in the form of a scaled frequency signal over lead 282, from mass flow rate circuit 30 located within mass flow rate electronics 100 and various density based conversion factors calculated by and serially transmitted over serial communication lines 22 by densimeter processor 50 situated within densimeter electronics 200. DRT 60 possesses the capability to calculate volumetric flow rate and totalized volumetric flow in standard volumetric measurements (e.g. standard barrels/day) for each component in a multi-component fluid stream. Suitable contact closures are provided over leads 257 for indicating desired alarm conditions.

If the inventive metering system is used to measure an oil-water flow stream, then this system can advantageously function as a net oil. Specifically, mass flow rate circuit 30 first measures the mass flow rate of the oil-water emulsion. At the same time, the density of the flowing emulsion is measured by densimeter processor 50. Given the measured density value along with various constants previously entered by the user (such as standard crude oil and saltwater densities at 60 degrees F), densimeter processor 50 calculates various parameters: a mass to volume conversion factor, and oil cut and water cut density ratios. These three parameters are then transmitted by the densimeter processor to DRT 60. The DRT then uses these parameters to separately calculate the volumetric flow rate of the entire flow stream and of the water and oil components (in, for example, standard barrels/day). Thereafter, digital rate totalizer and display 60 separately totalizes these volumetric flow rates to yield totalized volumetric flow measurements of the entire flow stream and of the individual water and oil components. The volumetric flow and totalized flow measurements for the entire stream or either the water or oil components can be separately displayed. Furthermore, as set forth below, DRT 60 can also separately calculate and display mass flow rate and totalized mass flow for the entire flow stream and for the individual oil and water components.

B. Mass Flow Rate Circuit

Figure 3A:
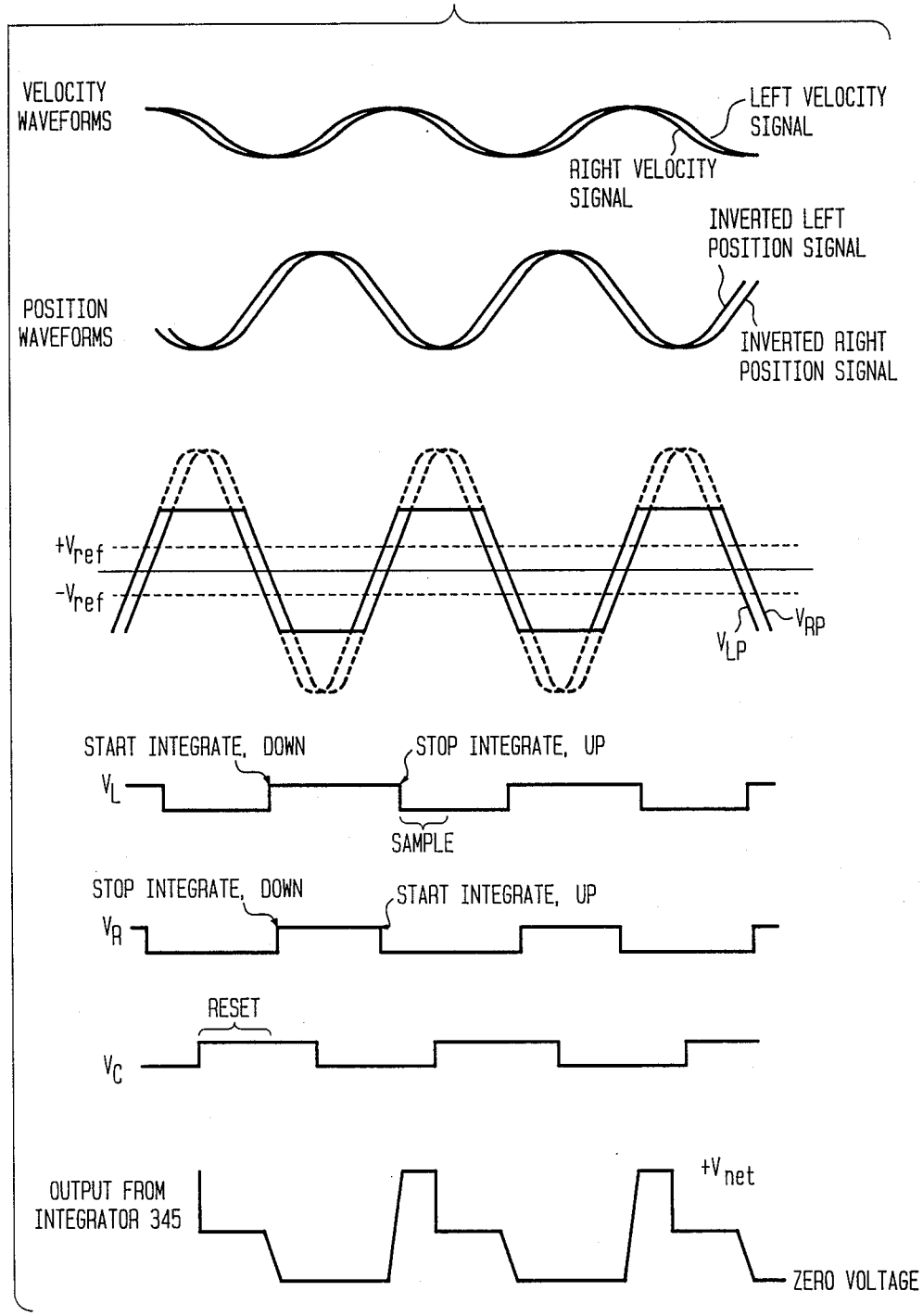
FIG. 3A depicts various waveforms that occur within Mass Flow Rate Circuit 30 shown in FIG. 2 for conditions of positive flow.
Figure 3B:
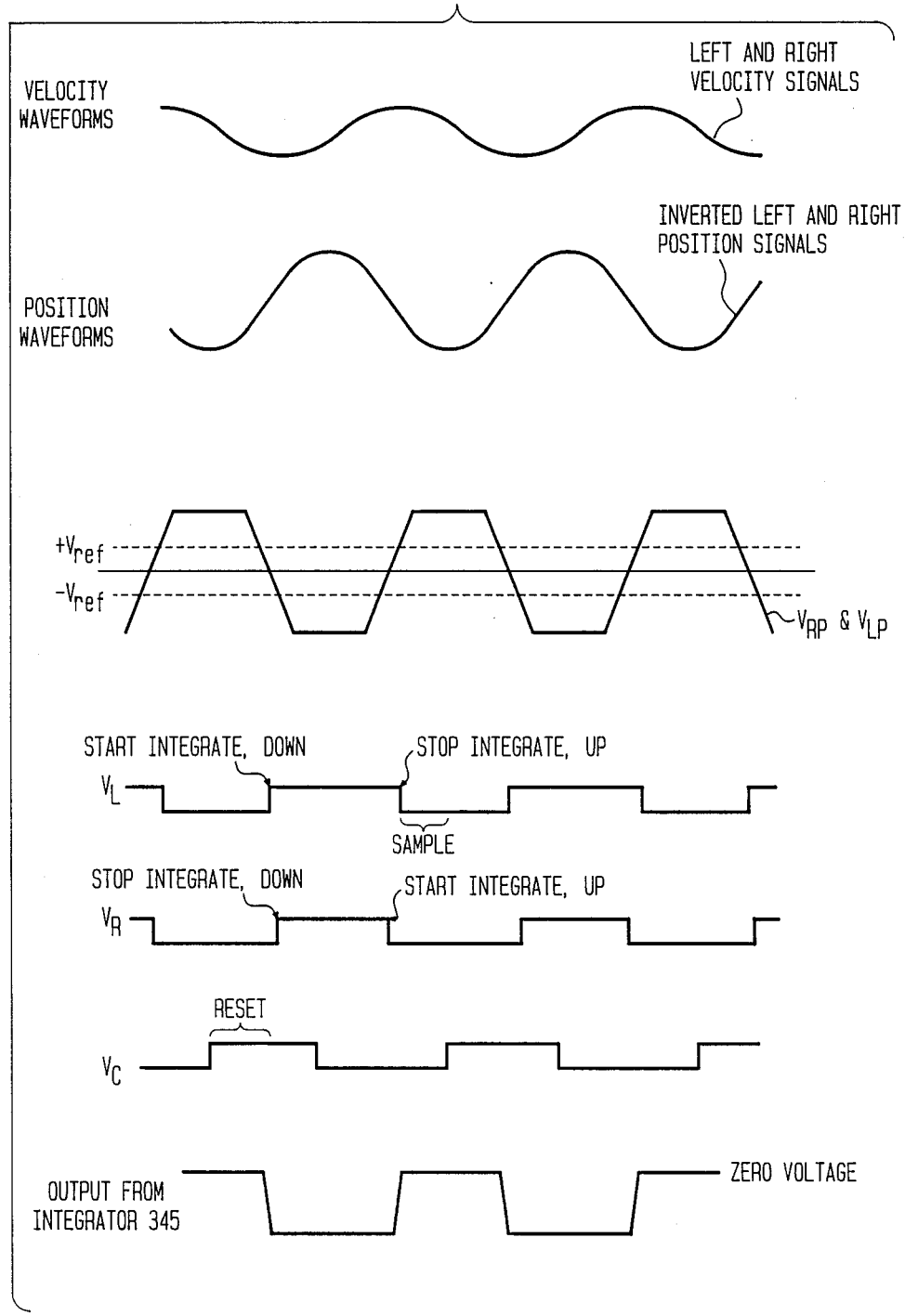
FIG. 3B depicts corresponding waveforms to those shown in FIG. 3A for conditions of no flow.

FIG. 3 depicts a block diagram of mass flow rate circuit 30, shown in FIG. 2, with the corresponding waveforms generated by this circuit under conditions of positive flow shown in FIG. 3A and no flow shown in FIG. 3B.

Here, incoming sinusoidal velocity signals from right and left velocity sensors $160_R$ and $160_L$, are applied via leads $165_R$ and $165_L$, to integrators 305 and 330, respectively. With fluid flowing in a positive direction, i.e. into meter assembly 10 through inlet end 101 (see FIG. 1), the Coriolis forces generated thereby will cause the right flow tube to pass through its mid-plane of oscillation before the left tube passes through its corresponding mid-plane of oscillation. As a result, the right velocity signal will lead the left velocity signal, as is evident in the velocity waveforms shown in FIG. 3A. This time difference is substantially proportional to the flow rate. As a result of the operation of integrators 305 and 330, both velocity signals are shifted in phase by ninety degrees and inverted to yield inverted right and left position signals. The outputs of integrators 305 and 330 are amplified and clipped by amplifiers 310 and 335, respectively. The resulting clipped right and left position signals $V_{RP}$ and $V_{LP}$, and are compared to respective positive and negative reference levels, $+V_{ref}$ and $-V_{ref}$, by level detectors 315 and 340, respectively. Time integrator 345 integrates the time difference existing between the output signals $V_R$ and $V_L$, produced by level detectors 315 and 340 and appearing on leads 316 and 343, respectively. Reset signal $V_C$, appearing on lead 323, is used to reset integrator 345 and thereby define the point in time at which integration begins. Reset signal $V_C$ is formed by first applying the left velocity signal appearing on leads $165_L$ and 318 to amplifier 320 which amplifies and clips this signal and thereafter applying the resulting signal to zero crossing detector 325. Specifically, as illustrated in FIG. 3A, integrator 345 will reset itself during the time interval occurring between a rising edge on reset signal $V_C$ and a rising edge on signal $V_L$ (the reset condition). Thereafter, integrator 345 will negatively integrate the time period occurring between the rising edges on signals $V_L$ and $V_R$ and then positively integrate the time difference occurring between the falling edges on signals $V_R$ and $V_L$. The output of integrator 345 is applied to sample and hold (S/H) circuit 350. This circuit samples the output voltage produced by integrator 345 after positive integration has ceased and before a reset condition has occurred and, in turn, produces a value equivalent to the value of the sampled integrator output voltage. Thereafter, S/H circuit 350 maintains its output at this value during the remainder of the next integration cycle. As such, for a positive flow, the output of S/H circuit 350 will track the net positive voltage $+V_{net}$ produced by integrator 345. This net positive voltage is proportional to the time difference between the velocity signals and hence to the mass flow rate. For flows occurring in the reverse direction, the Coriolis forces are reversed and the net integrator output voltage and that produced by the sample and hold circuit will be negative rather than positive. For conditions of no flow, as shown in FIG. 3B, the left and right velocity waveforms will be in phase as will be the inverted left and right position signals and voltages $V_{LP}$ and $V_{RP}$. Consequently, a zero valued net output voltage will be produced by integrator 345 immediately prior to the occurrence of a reset condition.

The output of sample and hold 350 is smoothed by low pass filter 355 and thereafter applied to voltage-to-frequency converter 360. This converter is adjusted to produce a scaled frequency output on lead 282, typically 0–10,000 Hertz, which is proportional to the full range of flow rates that can be measured using meter assembly 10. The signal produced by RTD temperature sensor 190 and appearing on lead 195 is used to vary the scaling of converter 360 for any temperature induced variations in the modulus of rigidity (sheer modulus) of the flow tubes. Specifically, the temperature signal is first linearized by circuit 370 to compensate for the non-linear characteristics of the RTD temperature sensor and thereafter applied over lead 372 to the GAIN input of converter 360. To produce a 4–20 mA analog output signal on lead 281, the frequency output appearing on lead 282 is applied to frequency to 4–20 mA converter 365. The reader is referred to an instruction manual entitled "Micro-Motion Model D Mass Flow Meters, December 1985" (c. 1985: Micro-Motion, Inc.) for more detailed information regarding the operation of mass flow circuit 30.

FIG. 4 depicts a block diagram of flow tube drive circuit 40, shown in FIG. 2. This circuit receives the left velocity signal produced by coil $160_L$ and, in response thereto, provides a square wave drive signal to drive coil 180 at a frequency equal to the resonant frequency of the tube and in phase with its movement. As such, this drive signal injects mechanical energy into the flow tubes to overcome inherent mechanical losses and thereby ensures that both tubes continuously vibrate at their common resonant frequency. Moreover, this circuit automatically adjusts the positive and negative magnitudes of the square wave drive signal in order to advantageously compensate for viscous damping properties of the fluid passing through the meter.

Specifically, synchronous amplifier 449 produces a square wave that switches from a positive drive level to a negative drive level synchronously with each zero crossing of the left velocity signal, $V_L$, i.e. when both flow tubes simultaneously reach an end point of their oscillatory travel. In particular, during the positive portion of the velocity signal—as shown by the waveforms appearing in the figure, the synchronous amplifier routes a positive drive level to drive coil 180, via lead 185. Likewise, during the negative portion of the velocity signal, synchronous amplifier 449 routes a negative drive level to lead 185. The left velocity signal, $V_L$, appearing on lead 41 and produced by left velocity sensor $160_L$, is amplified by amplifier 432 before being applied as a switching signal to synchronous amplifier 449.

The remainder of this circuit sets the proper amplitude (magnitude and sign) for each of these two drive levels. In particular, the left velocity signal is shifted in phase by ninety degrees and then inverted to produce an oscillatory signal, $V_M$, that leads the left velocity signal by ninety degrees. The sign of the anticipatory signal determines what specific drive voltages will be applied as the positive and negative drive level inputs to synchronous amplifier 449 during the next half cycle of the velocity signal.

Specifically, the sinusoidal left velocity signal, $V_L$, produced by coil $160_L$ is applied, via lead 41, as input to ninety degree phase shifter 431. The sinusoidal output of the phase shifter is applied through amplifier 438 and linear inverter 439 to yield signal $V_M$ which is, in turn, applied to the inverting input of difference amplifier 443. Signal $V_M$ leads left velocity signal $V_L$ by ninety degrees and, as such, is the integrated left velocity (position) signal.

Difference amplifier 443 compares signal $V_M$ against a pre-determined reference level $V_{LR}$. A comparison occurs, at every peak (positive and negative) of signal $V_M$ to determine if this peak value is a positive or negative peak. If the comparison indicates that the peak value lies below the reference level $V_{LR}$), then this peak value is a negative peak In this case, difference amplifier 443 will produce a positive level at its output which will result in a positive drive signal being produced by amplifier 445 and applied to the positive drive input to synchronous amplifier 449. Inasmuch, as the positive output of amplifier 445 is inverted by linear inverter 452, a negative drive signal is applied to the negative drive level input to the synchronous amplifier.

To prevent each of these drive signals from changing polarity during the next half cycle of signal $V_M$, differential amplifier 443 sample it inputs and provides a new output value only at tho occurrence of a high level on its ENABLE input. In particular, this amplifier is enabled only at each negative going zero crossing in the left velocity signal, $V_L$, by a suitable enable pulse appearing on lead 437. To generate this pulse, the output of amplifier 432 is applied as input to comparator 434 which functions as a zero crossing detector. The output of this detector is a square wave which is in phase with left velocity signal $V_L$. This square wave is, in turn, applied as input to negative edge detector 435 which produces a pulse at each negative going transition in this square wave, i.e. at each negative going zero crossing in the velocity signal.

Drive circuit 40 functions as an automatic gain control by automatically varying the magnitudes of both drive levels in order to maintain the magnitude of the integrated left velocity (position) signal equal to the magnitude of the reference signal, $V_{LR}$. As such and as noted, this circuit advantageously compensates the drive signal and flow tube motion for viscous damping properties of the fluid flowing through the meter. Specifically, since amplifier 45 is a linear amplifier with a pre-set gain, the output of this amplifier, and hence the magnitudes of both the positive and negative drive levels, will linearly vary with respect to the difference between the magnitudes of the position signal, $V_{Ml}$, and *the reference signal*, $V_{LR}$. For example, if the magnitude of position signal $V_M$ lies below (above) that of the reference signal, then the output of difference amplifier 443 increases positively (negatively). A drop in the magnitude of the position signal can result from an increase in the viscosity of the fluid passing through the meter which damps the motion of the flow tubes and correspondingly reduces the outputs of the velocity sensors and the magnitude of position signal. Similarly, a decrease in fluid viscosity can correspondingly increase the magnitude of both the velocity sensor output signals and the position signal. Now, for example, in the event the fluid viscosity increases and the amplitude of the position signal correspondingly decreases, the signal produced by amplifier 443 increases positively. This, in turn, increases the magnitudes of both drive levels which will subsequently increase the magnitude of the flow tube vibration. The magnitudes of both drive signals and hence the flow tube vibration will increase to whatever appropriate values are necessary to ensure that the magnitude of the position signal $V_M$, once again equals that of the reference signal, $V_{LR}$. By automatically varying the magnitudes of both drive levels and flow tube vibration in response to any changes in the magnitude of the position signal, drive circuit 40 advantageously compensates for any viscous damping imparted to the vibratory motion of the flow tubes by the fluid passing therethrough.

The gain of each amplifier and inverter in circuit 40 is selected to ensure that the magnitude of the drive signal applied to tho drive coil is sufficient to vibrate both flow tubes in an equal sinusoidal pattern at their common resonant frequency. These gains can be adjusted to provide different amplitudes for the positive and negative drive signals in order to compensate for any physical differences that occur between the two flow tubes, e g. bends, small kinks and the like that were incurred during mounting of both tubes into meter assembly 10 (see FIG. 1).

C. Densimeter Processor 50

This discussion will now turn to a detailed explanation of densimeter processor 50. The hardware that constitutes the densimeter processor is shown in block diagram form in FIG. 5. The software executed by this hardware will be discussed later in conjunction with FIGS. 7, 8 and 9A–9D.

1. Densimeter Hardware

FIG. 5 shows a block diagram of the hardware of densimeter processor 50. As discussed earlier, the densimeter processor appropriately processes the signals generated by RTD 190 and left velocity sensor $160_L$ appearing on leads 51 and 53, respectively, to determine the density of an unknown fluid passing through meter assembly 10, shown in FIG. 1. Resulting density values are provided on output lead 2832 in 4–20 mA form. Tube temperature is also provided in the same form on output lead 2831. Both output leads 2831 and 2832 collectively form output leads 283. Density and tube temperature output information is also provided in serial RS-232C form on serial communication lines 22. When the inventive metering system is used as a net oil computer, densimeter processor 50 also provides the values of oil cut and water cut density ratios, and a mass to volume conversion factor all in RS-232C form on serial communication lines 22. Densimeter processor 50 also provides high and low relay contact closures on leads 255 for appropriately actuating high and low level alarms.

In particular, the densimeter processor is a 8-bit microprocessor based system. The system illustratively contains common bi-directional address and data busses 540 that link 8b-it microprocessor 545, memory 547, analog-digital (A/D) converter 537, analog output circuit 560, display controller 571 and keyboard encoder 575. Tube period measurement circuit 530 is also connected to busses 540. Appropriate clock signals are provided by system clock circuit 580 which sets its time base from oscillations produced by crystal 585.

Tube period measurement circuit 530 measures the period at which the flow tubes vibrate and produces a digital value equivalent to the period. Specifically, the sinusoidal left velocity signal is applied over lead 53 to comparator 532 located within circuit 530. This comparator squares the velocity signal and applies the resulting squared signal to the data input of flip/flop 534 which, in turn, divides the frequency of the squared signal by half As long as the divided signal remains high (during exactly one period of the tube vibration), clock pulses are gated into 16-bit down counter 535 to successively decrement the contents of this counter from the hex value "FFFF". The decrementation stops once a falling transition occurs in the divided velocity signal. At this point, an interrupt to the microprocessor is generated by the falling transition appearing on ½ frequency interrupt line 536. At the same time, the falling transition causes counter 535 to hold its final value. The interrupt is then serviced by execution of tube period interrupt routine 800 (shown in FIG. 8 and discussed in detail later) which reads the count, resets the counter to "FFFF", subtracts the count from the hex value "FFFF" to generate an upcount and then suitably filters the resulting upcount to yield a measurement of the tube period for subsequent use by the microprocessor.

Tube temperature information is provided to the microprocessor, via busses 540, through RTD linearizing and scaling circuit 511 and A/D converter 537. In particular, RTD 190 is connected via lead 51 to an input of circuit 511. This circuit reads the voltage appearing across RTD 190. Inasmuch as this voltage varies non-linearly with temperature, circuit 511 linearizes the voltage, in a well known fashion, and thereafter scales it by a pre-determined constant to yield a resolution of 0.05 degree C./bit (after conversion by A/D 537) and referenced to 0 degrees C. The resulting scaled RTD voltage is applied to an input of 12 bit A/D (analog-to-digital) converter 537. This voltage is converted and read by the microprocessor every 20msec during execution of 20msec interrupt routine 900, shown in FIGS. 9A–9D and discussed in detail later.

Memory 547 contains random access memory (RAM) for temporary data storage, erasable a nd electronically programmable read only memory (EEPROM) for program storage and non-volatile RAM (NOVRAM) for storage of various values in the event of a power outage. New values for various constants are written into the NOVRAM whenever the densimeter is undergoing calibration, as is fully discussed in conjunction with FIGS. 9A–9D below.

Microprocessor 545 contains internal timer 544 which is set, early into the execution of main program 700 (see FIG. 7 which is discussed in detail later), to time out every 20 milli-seconds and generate an interrupt. This interrupt causes the microprocessor to execute the 20 msec interrupt routine. In addition, the microprocessor provides various output parameters (i.e. density, tube temperature and, when the inventive system is used as a net oil computer, oil cut and water cut. density ratios and a mass to volume conversion factor) in serial fashion, through appropriate input/output (I/O) port lines and via leads 543, to serial interface 551. The serial interface is a generally a line, driver/line receiver pair that provides an appropriate interface to serial communication lines 22. The microprocessor can also enable or disable selected alarm outputs, by placing an appropriate signal on its I/O port lines and via leads 546, to digital output circuit 553.

Analog output circuit 560 receives tube temperature and measured density values in parallel form and converts these values into separate analog 4–20 mA current signals for application to lines 2831 and 2832, respectively. Specifically, this circuit contains two digital to 4–20 mA converters: one being timer 561 and pulse width to 4–20 mA converter 563, and the other being timer 565 and pulse width to 4–20 mA converter 567. Specifically, timer 561 is loaded, in parallel, under control of microprocessor 545 with a digital temperature value appearing on the data bus within busses 540. The contents of the timer are thereafter successively decremented at each subsequent clock pulse to provide a pulse width modulated (PWM) pulse train wherein each pulse has a width that proportionally varies with the measured temperature. The resulting PWM pulse train is then converted by converter 563 into a 4–20 mA signal in a well known fashion. Every 20 milliseconds, microprocessor 545 reloads timer 561 with a new temperature value to update the 4–20 mA current outputs. Timer 565 and converter 567 function in an identical manner to produce the 4–20 mA measured density signal which is also updated every 20 milliseconds by the microprocessor.

Display 573, typically a pair of well known liquid crystal displays, continuously displays measured density and tube temperature. These displays are updated with current information every 400 milliseconds by microprocessor 545. At these times, new data is placed on the data bus, that forms part of busses 540, by the microprocessor and is thereafter loaded into display controller 571 which, in turn, controls the operation of display 573.

During operation of the inventive metering system, an operator enters various calibration information into the system, such as a desired unit of measure for display of density (e.g. brix, API units, pounds/barrel, etc. and density readings for various known fluids (air and water; and, when the inventive system is being used as a net oil computer, reference densities of crude oil and saltwater at 60 degrees F.). Under the control of the microprocessor, keyboard encoder 575 scans the keyboard every 20 milliseconds and applies incoming information onto the data bus that forms part of busses 540.

2. Densimeter Software

Figure 7:
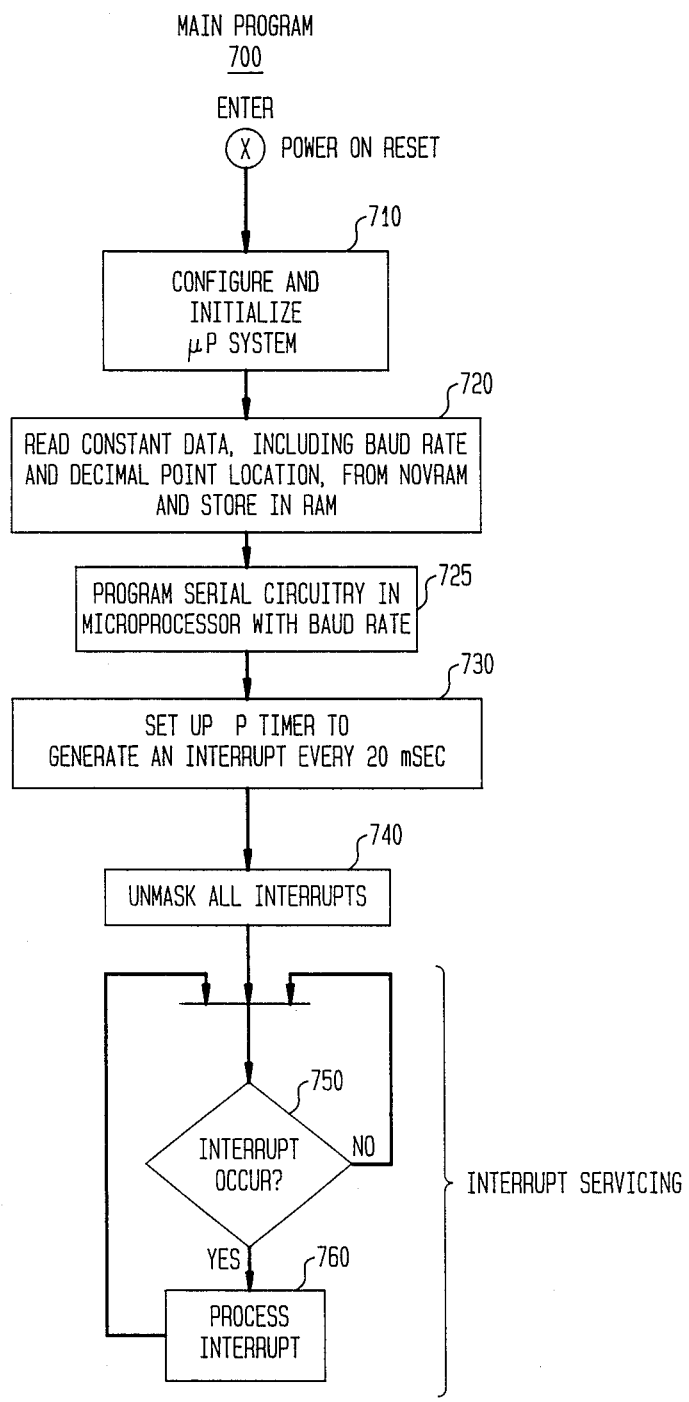
FIG. 7 is a flowchart of Main Program 700 which is executed by Densimeter Processor 50, shown in FIG. 5.

This discussion will now proceed with a detailed explanation of the software executed by densimeter processor 50. This software is basically interrupt driven. A flowchart of main program 700 executed by densimeter processor 50 is shown in FIG. 7. Tube period interrupt routine 800 and 20msec interrupt routine 900, which are also both executed in this processor, are respectively shown in FIGS. 8 and 9A–9D.

As shown in FIG. 7, upon power-up of the inventive system, execution of main program 700 initiates with entry into configuration and initialization block 710. First, this block, when executed, configures the microprocessor to read from EEPROM memory. Thereafter, this block establishes a software map which maps all the other bus devices, such as A/D converter 537 and display controller 571 (see FIG. 5), into appropriate RAM memory locations. Once this has been completed, block 110, shown in FIG. 7, performs various diagnostics and memory checks and also resets various memory locations, such as those used for temporary data storage and flags, to zero. Thereafter, execution passes to block 720 which, when executed, causes various constants to be read from NOVRAM into RAM for subsequent use. These constants include the baud rate for the serial circuitry located within the microprocessor and, where appropriate, decimal point locations. To save execution time, the microprocessor only performs integer arithmetic and therefore needs to monitor the location of the decimal point for calculation and display purposes. Once these operations have been completed, block 725 is executed which programs the serial circuitry located within the microprocessor with the baud rate that has just been accessed from NOVRAM. Thereafter, execution passes to block 730. Here, microprocessor 545 (see FIG. 5) sets up its internal timer such that it generates an interrupt every 20 milli-seconds. Now, as shown in FIG. 7, execution passes to block 740 which unmasks all interrupts. From this point on, main program 700 merely waits for an interrupt to occur, then processes the interrupt and finally re-enters a wait state until the occurrence of the next interrupt. To illustrate these steps, execution is shown as passing to decision block 750 which, as shown, continually re-executes unless an interrupt occurs. When an interrupt occurs, execution proceeds to block 760 wherein the interrupt will be serviced by a particular routine depending upon which interrupt occurs. Interrupts occur from two sources: tube period measurement circuit 530, as discussed above in connection with FIG. 5, and the 20 millisecond timer; each invokes a corresponding interrupt servicing routine (tube period interrupt routine 800 shown in FIG. 8 and 20msec interrupt routine 900 shown in FIGS. 9A-9D). An interrupt from tube measurement circuit 530 indicates that this circuit has completed a current measurement of the tube period and the resulting measurement needs to be read into the microprocessor for subsequent use. An interrupt from the 20 milli-second timer invokes a new density measurement calculation to update the analog density and temperature outputs 2831 and 2832 (see FIG. 5) and, at certain times as described below, display 573. At the conclusion of either interrupt servicing routine, execution returns to decision block 750 as shown in FIG. 7 to await the occurrence of the next interrupt.

Figure 8:
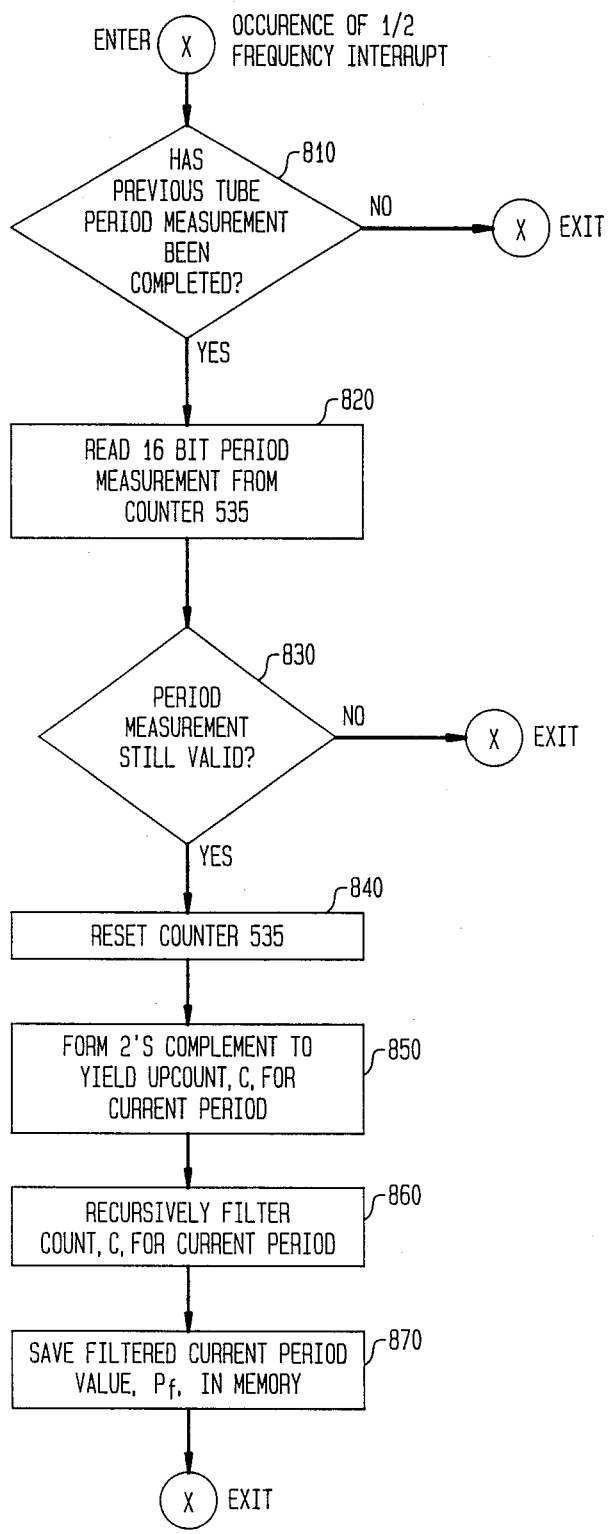
FIG. 8 is a flowchart of Tube Period Interrupt Routine 800 which is executed by Densimeter Processor 50.

Tube period interrupt routine 800 is depicted in flowchart form in FIG. 8. As noted, this routine when executed, provides a filtered digital value of the period, at which the flow tube is vibrating. In particular, this routine is entered whenever tube period measurement circuit 530 (see FIG. 5) completes a measurement of the tube period and generates an interrupt on lead 536 This interrupt signifies that a tube period measurement is ready to be read into the microprocessor for subsequent storage and eventual use in a density calculation. As shown in FIG. 8, execution first proceeds to block 810. This block determines whether the tube period measurement provided by circuit 530 has been completed. If so, the measurement is valid The measurement is not valid if the microprocessor consumed an excessive amount of time in servicing the 20msec interrupt routine and thereby forced the tube period interrupt to wait before it could be serviced. If this happens, then circuit 530 could have begun a new tube period measurement by counting down from the value "FFFF" before the microprocessor was able to read the previous measurement. In this case, the count occurring at the time the microprocessor reads counter 535 (see FIG. 5) would not be valid and must be ignored. Hence, if an incomplete (invalid) measurement is detected by decision block 810, then execution proceeds, via the NO path from this block, to exit from this routine and return to main program 700. Alternatively, if decision block 810 determines that the previous tube measurement has been completed and counter 535 has not been reset and/or decremented prior to its count being read by the microprocessor, then execution proceeds, via the Yes path from this decision block, to block 820. This latter block, when executed, reads the 16 bit count stored in counter 535 using two successive read operations each of which reads one 8-bit byte at a time. Once this has been completed, execution passes to decision block 830. This block determines whether the count that has just been read from the counter is valid. This count is not valid if its value changes during the read operation undertaken by execution block 820. This can occur inasmuch as the counter is able to be decremented while it is being read. In the event decision block 830 determines that the count (period measurement) has indeed changed during the interval it is being read, then the count is invalid and must be ignored. In that case as shown in FIG. 8, execution passes via the NO path from this block, then exits from this routine and finally returns to main program 700. Alternatively, if the period measurement is still valid, then execution proceeds, via the YES path, from decision block 830 to execution block 840, which when executed, resets counter 535.

Thereafter, execution passes to execution block 850. Here, the down count value read from counter 535 is two's complemented to convert the value to an upcount value, C. Once this occurs, block 860 is executed to recursively filter the resulting upcount value, C, through a digital filter in order to remove any measurement noise from the count and produce a filtered period value, Pf. The digital filter used in the present embodiment is given by the following equations:

$$\text{SUM}_n = \text{SUM}_{n-1} + C_n - \frac{1}{K}(\text{SUM}_{n-1} + C_n) \quad (1)$$

and $$Pf_n = \frac{256}{K}(\text{SUM}_{n-1} + C_n) \quad (2)$$

where:
n represents the current measurement;
n−1 represents the previous measurement;
256 is a scaling factor; and
K sets is the filter time constant. If the value of K is 16, 32 or 64, then the filter possesses time constants of 1, 2 or 4 seconds, respectively.

Once the filtering has been completed, execution passes to block 870, which, when executed, merely stores the current filtered period value, Pf, in RAM memory for a subsequent density calculation undertaken during the next execution of the 20msec interrupt routine. After the current filtered period value has been stored, execution then exits from routine 800 and re-enters main program 700.

Figure 9B:
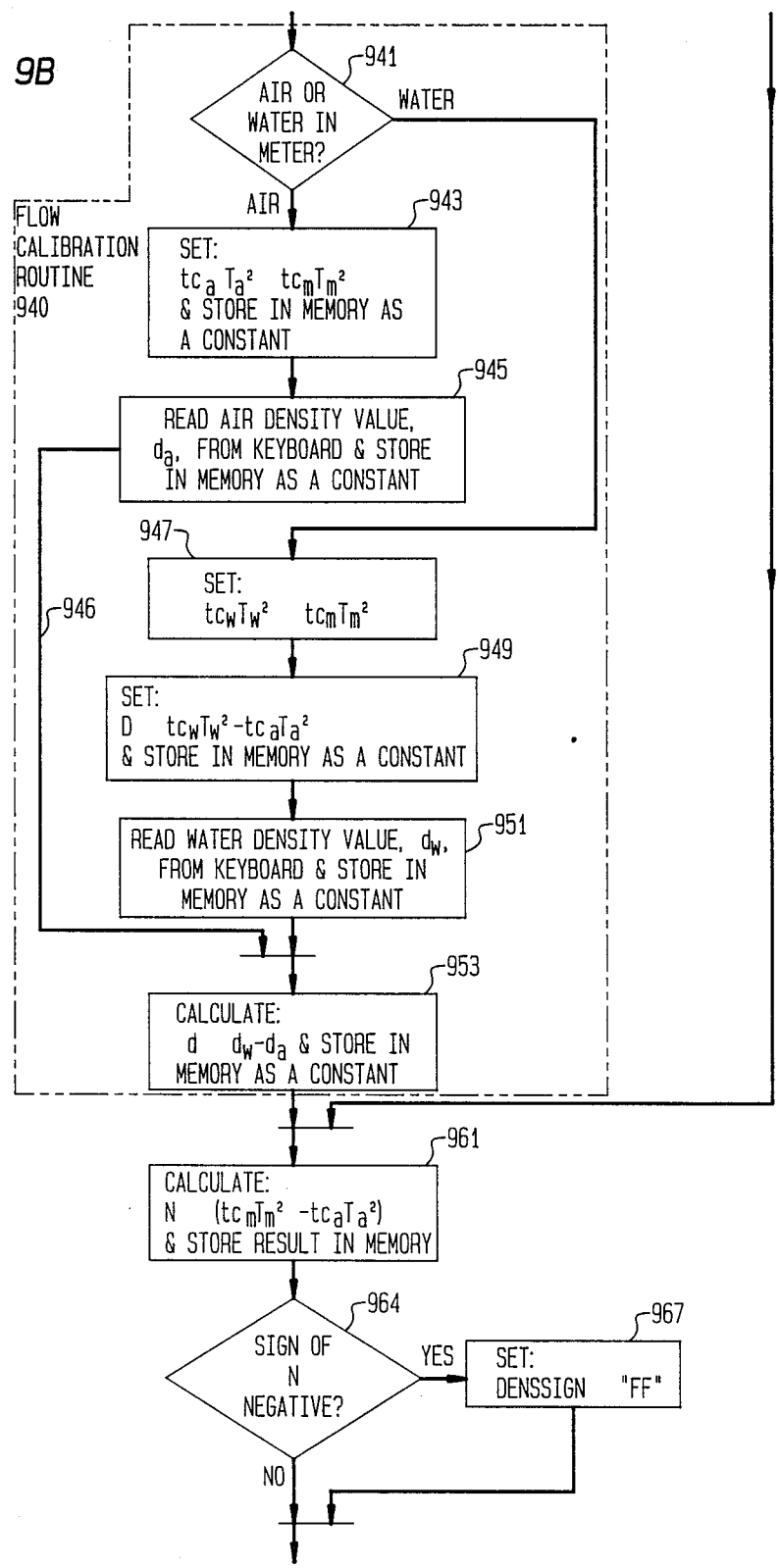
Figure 9C:
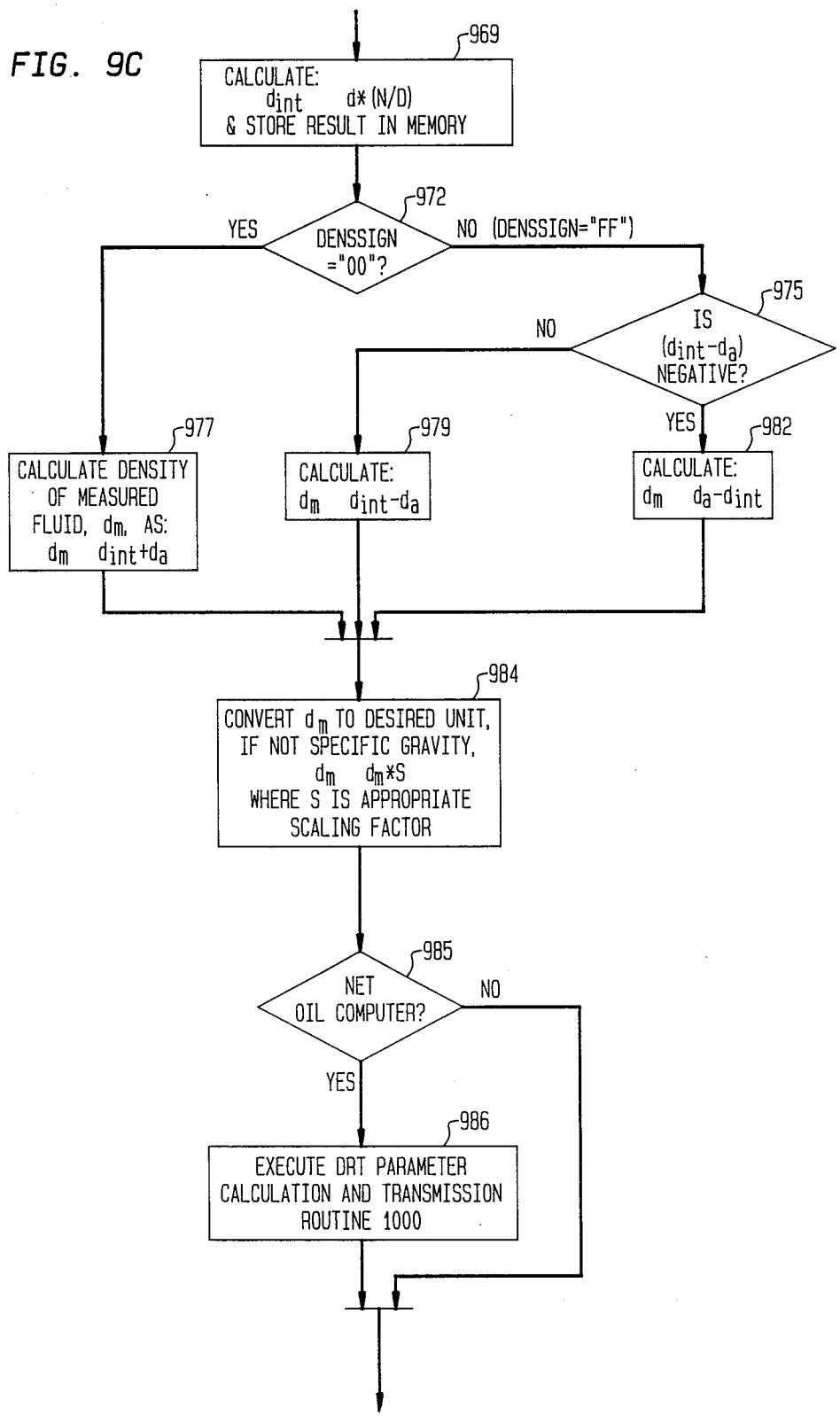
Figure 9D:
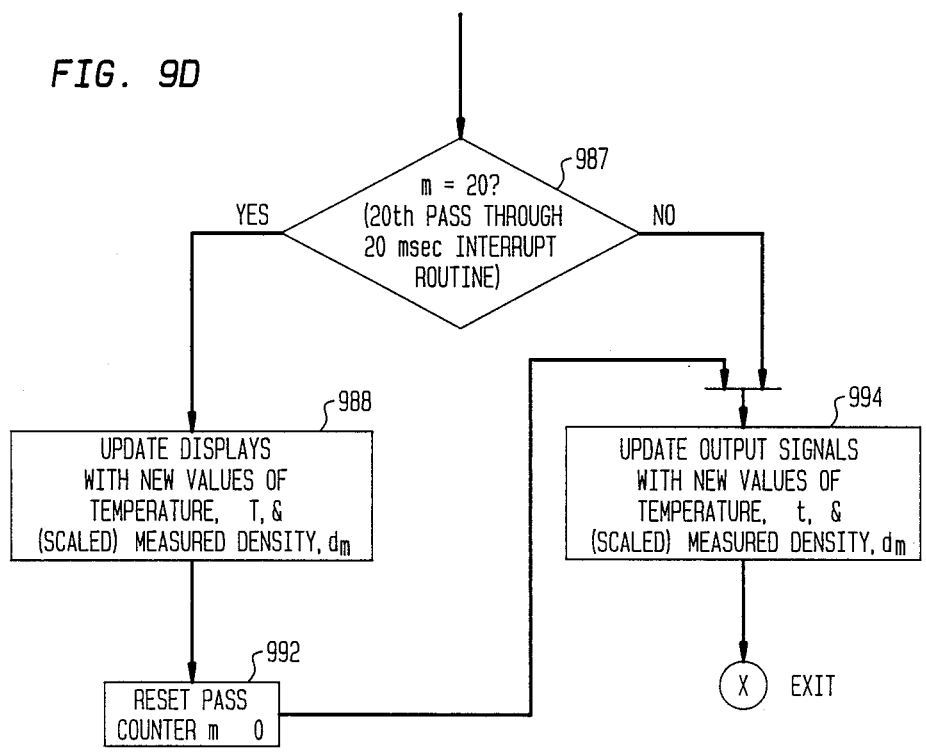

FIGS. 9A–9D collectively depict a flowchart of 20msec interrupt routine 900, with the correct alignment of the drawing sheets for these figures shown in FIG. 9. As noted previously, this routine is executed each time 20 milli-second timer 544 (see FIG. 5) times out. This invokes a density determination, a meter calibration procedure—when so selected by an operator, and an updating of the densimeter processor displays and analog outputs with current density and tube temperature information.

Now, in order to gain a full understanding of this routine, it is necessary to digress from the software and discuss two fundamental aspects of the present invention: the manner in which density is characterized in terms of tube movement and the manner in which the inventive system is calibrated using two known fluids.

For a vibrating spring-mass system, the frequency, f, at which, the spring-mass system vibrates is given by:

$$2(\pi) f = \text{sq. root } (K/M) \quad (3)$$

where:
 K = the spring constant of the system, and
 M = the total mass

Now, n a vibrating tube densimeter, the total mass, M, is comprised of the mass of the vibrating tube, $m_{tube}$, and the mass of the liquid, $m_{liquid}$, contained therein:

$$M = m_{tube} + m_{liquid} \quad (4)$$

The mass of the liquid equals the density of the liquid, rho, times the volume of the liquid, V, contained in the $$m_{liquid} = (\text{rho}) V \quad (5)$$

Therefore, $$M = m_{tube} + (\text{rho}) V \quad (6)$$

Now, substituting equation (6) into equation (3) and squaring both sides yields:

$$4(\pi)^2 f^2 = \frac{K}{m_{tube} + (\text{rho}) V} = \frac{4(\pi)^2}{T^2} \quad (7)$$

where: T = 1/f and is the period at which the tube oscillates.

Now, solving equation (7) for (rho) yields:

$$\text{rho} = \frac{K}{4(\pi)^2 V} T^2 - \frac{m_{tube}}{V} \quad (8)$$

In equation (8), terms 4, (pi), $m_{tube}$ and V are constants and the spring constant K varies linearly with temperature. As such:

Let:

$$\frac{K(t)}{4(\pi)^2 V} = K_1(t) \quad (9)$$

and $$\frac{m_{tube}}{V} = K_2 \quad (10)$$

Now, equation (8) can be re-written as follows:

$$\text{rho} = K_1(t) T^2 - K_2 \quad (11)$$

and further as:

$$\text{rho} = (K_1)(tc) T^2 - K_2 \quad (12)$$

where:
 tc is the temperature coefficient for the material, illustratively 316L stainless steel, that is used to construct the flow tubes, and $K_1$ and $K_2$ are fixed coefficients.

As one can appreciate, equation (12) generally characterizes the movement of the tube and advantageously relates density of any fluid flowing through the tube in terms of the period at which the flow tube vibrates. In accordance with the teachings of the present invention, use of this generalized quadratic equation advantageously forms the basis for measuring density of an unknown fluid that passes through the flow tube.

Now, to calibrate the inventive system, it is first necessary to determine the values of coefficients $K_1$ and $K_2$ in quadratic equation (12). This can be readily accomplished by successively passing two fluids, e.g. air and water, with known densities, $\text{rho}_a$ and $\text{rho}_w$, through the flow tubes in a meter assembly in use and measuring the corresponding tube period. Thereafter, the values of the density of these fluids, and the respective tube periods and temperature coefficients are successively substituted into equation (12) to yield two simultaneous equations that can be solved for the values of coefficients $K_1$ and $K_2$. Once calibration has been completed, the values for $K_1$ and $K_2$ are inserted into quadratic equation (12) to subsequently fit the generalized equation to the particular meter assembly being used and thereby relate density of an unknown fluid to the measured temperature and period of the flow tube, in this meter, while the unknown fluid passes therethrough. Now, to save execution time during execution of interrupt routine 900, several of the above steps are combined as will now be discussed.

In particular, the two simultaneous equations that can be solved to yield the values for coefficients $K_1$ and $K_2$ are: are:

$$\text{rho}_a = K_1(tc_a) T_a^2 - K_2 \quad (13)$$

$$\text{rho}_w = K_1(tc_w) T_w^2 - K_2 \quad (14)$$

where:
 $tc_a$ and $tc_w$ represent the respective temperature coefficients $K_1$ and $K_2$ expressed in terms of
 $T_a$ and $T_w$ represent the respective period at which the flow tue vibrates when either air or water flows therethrough Now, solving equations (13) and (14) for $K_1$ yields:

$$K_1 = \frac{\text{rho}_w - \text{rho}_a}{tc_w T_w^2 - tc_a T_a^2} \quad (15)$$

Substituting this value for $K_1$ into equation (14) provides:

$$K_2 = (\text{rho}_w - \text{rho}_a) \frac{tc_a T_a^2}{tc_w T_w^2 - tc_a T_a^2} \quad (16)$$

Now with coefficients $K_1$ and $K_2$ expressed in terms of known densities, known temperature coefficients and easily measured tube periods, these two terms can be substituted back into equation (12) to yield equation (17), as follows:

$$\text{rho}_m = (\text{rho}_w - \text{rho}_a) \frac{(tc_m T_m^2 - tc_a T_a^2)}{(tc_w T_w^2 - tc_a T_a^2)} + \text{rho}_a \quad (17)$$

where:
$\text{rho}_m$ is the unknown density of a measured fluid; $tc_m$ is the temperature coefficient of the flow tube while the unknown fluid flows therethrough; and
$T_m$ is the measured period at which the flow tube vibrates while the unknown fluid passes therethrough.

As is readily apparent, equation (17) determines the density of the unknown fluid as a linear function of the squared tube period measurement of the unknown fluid, and the squared tube period measurements and corresponding known density values of two known fluids e.g. air and water). This equation is implemented in the 20msec interrupt routine. In general, during execution of this routine, all terms appearing in equation (17), other than the term $tc_m T_m^2$, are determined during calibration and are appropriately entered into memory. To save time, those portions of equation (17), such as the denominator, which do not depend upon any measurements of the unknown fluid are also calculated during calibration and stored in memory. Hence, to measure the density of an unknown fluid, a tube period measurement, $T_m$, is obtained for the unknown fluid and its corresponding tube temperature coefficient, $tc_m$, is calculated. Thereafter, both of these parameters are inserted into equation (17) to calculate the density, $\text{rho}_m$, of the unknown fluid.

Now, with this description in mind, the discussion will now turn back to a detailed examination of 20 msec interrupt routine 900 depicted in flowchart form in FIGS. 9A-9D.

As discussed above, routine 900 is executed upon every occurrence of a 20 milli-second interrupt. Upon entry into this routine, block 903 is first executed. This block queries keyboard encoder 575 (see FIG. 5) to determine if any new values have been entered into the keyboard. If so, these values are appropriately stored in memory 547 for subsequent use. Thereafter, as shown in FIG. 9A, execution proceeds to block 906 which increments pass counter, m, by one. This counter is incremented by one every time interrupt routine 900 is executed. As will be seen below, the pass counter is used to update the displays every 400 milli-seconds, i.e. after 20 iterations have been completed through interrupt routine 900. After execution of block 906 is complete, execution then proceeds to block 909. Here, the latest filtered value of the tube period, $P_f$, which has been previously stored in memory 547 (see FIG. 5) by tube period interrupt routine 800, is first read from memory 547 and then squared to yield the squared measured tube period, $Tm^2$, which is stored in memory for subsequent use during execution of interrupt routine 900.

Execution now proceeds to block 911. This block instructs A/D converter 537 (see FIG. 5) to read the current value of tube temperature, delta t, sensed by RTD 190 and then to convert it into digital form. The value produced by the converter is referenced to 0 degrees Centigrade (C), i.e. the output of the converter is zero at this temperature; below zero temperatures are negative and above zero temperatures are positive. Thereafter, this temperature value is tested, by decision block 915, to determine whether the sign of the temperature value is positive or negative. In the event the sign is negative, then execution proceeds via the YES path from this decision block, to execution block 918 This latter block, when executed, sets a flag, here TEMPSIGN, to an appropriate value, here the hex value "FF", to signify a negative temperature. Inasmuch as the spring constant for metals varies negatively with increasing temperature, the status of this flag Will specific whether the temperature factor is added or subtracted in the next calculation.

Once the TEMPSIGN flag has been set or in the event the tube temperature is positive, then execution proceeds to block 921. This block, when executed, calculates the temperature factor for the flow tube, given its current temperature. This factor, for a 316L steel, is given by 225×(delta t). Inasmuch as the A/D converter provides a temperature value with a resolution of 0.05 degrees C, the temperature factor for 316 stainless steel at this resolution is 225 parts/10 million/0.05 degree C. Every metal has a different temperature factor. In the event the flow tub constructed from a material other than 316L stainless steel, then a different temperature factor other than 225 would be used. Thereafter, decision block 923 is executed. This block tests the TEMPSIGN flag to determine the sign of the temperature factor value. In the event the sign is positive, i.e. the value of TEMPSIGN equals zero, execution proceeds, via the NO path from decision block 923, to block 927. If, alternatively, the sign is negative, i.e. the value of TEMPSIGN equals "FF", execution proceeds, via the YES path, to block 925 instead. Blocks 925 and 927 both calculate the temperature coefficient for the fluid being measured, i.e. $tc_m$, and respectively add or subtract the value of the temperature factor in the calculation as dictated by its sign. Once either of these two blocks has been executed, execution then proceeds to block 929. This block, when executed, multiplies the value of the temperature coefficient by the squared period measurement to yield the variable $tc_m T_m^2$ and temporarily stores the result in memory for subsequent use.

The value of $tc_m T_m^2$ corresponds to whatever fluid is currently traveling through the flow tube. This value is for water, air or another known fluid if calibration is occurring; or is for an unknown fluid if that is being measured. The same form of the variable "temperature coefficient times squared tube period" appears in three different locations in equation (17). Therefore, different variables will be set to the value $tc_m T_m^2$ depending upon what fluid is passing through meter assembly 10 (see FIG. 1).

To set the proper variables to the value $tc_m T_m^2$, execution now proceeds to decision block 932. This block, based upon information entered through the keyboard, determines whether calibration is occurring. If not, execution passes via the NO path 936 from the decision block to block 961. In this case, the value $tc_m T_m^2$ is for an unknown fluid and equation (17) is then calculated, in the manner set forth below in conjunction with blocks 961-984, to determine the density of this fluid. Alternatively, if the operator has invoked calibration, control passes, via the YES path from decision block 932, to flow calibration routine 940.

Within flow calibration routine 940, decision block 941 is first executed to determine if water or air is flowing through the meter assembly. In the event that the operator has entered a certain key pattern for air or a different pattern for water, then execution respectively proceeds from decision block 941 either via the "AIR" path to block 943, or Via the "WATER" path to block 947. If control passes to block 943, signifying that the meter has just been purged with air and the flow tube is filled with air at atmospheric pressure, then this block, when executed, sets the variable $tc_A T_a^2$ the value of variable $tc_m T_m^2$ memory as a constant for later use. Thereafter, execution proceeds to block 945 which reads the density value for air that the operator has entered through the keyboard. This value is typically obtained by the operator from well-known tables which list air density as a function of altitude and temperature. The air density value is stored as a constant, $d_a$, in memory 545. Execution then proceeds to block 953, which will be discussed shortly. Alternatively, if the operator has entered "WATER" and control passes to block 947, then this block, when executed, sets the variable $tc_w T_w^2$ to and stores the result in the value of variable $tc_m T_w^2$ and $tc_a T_a^2$. a constant for later use. At this point, the system has stored values for $tc_w T_w^2$ and $tc_a T_a^2$. Therefore, execution proceeds to block 949 which calculates the denominator, D, of equation (17) and stores the resulting value in memory 547 (see FIG. 5) for subsequent use. Thereafter, as shown in FIG. 9B, execution proceeds to block 951 which reads the density value for water that the operator has been entered through the keyboard. This value is typically obtained by the operator from well-known tables which list water density as a function of temperature and is appropriately entered into the inventive system. The water density value is stored as a constant, $d_w$, in memory 547. At this point, execution proceeds either from block 945 or block 951 to block 953. This block updates the density difference, delta d, appearing in equation (17) and specifically the difference between the entered densities of air and water, with the newly entered density values and stores the result in memory as a constant. Execution of flow calibration routine 940 is now complete.

As can be seen, the densimeter is advantageously calibrated on a non-lumped basis, i.e. it is calibrated to physical flow conditions apart from the performance of the analog electronics. Inasmuch as the densimeter processor predominantly consists of digital circuitry, its performance is essentially unaffected by component aging, drift or the like that adversely affects the performance of analog circuitry used in densimeters known to the art. The performance of the analog circuitry that does exist in densimeter processor 50, specifically RTD linearizing and scaling circuit 511 and A/D 537, can, when needed, be independently calibrated using test signals without affecting the physical flow calibration. By bifurcating the physical flow calibration from the circuit calibration and maximizing the use of digital circuitry, better long term accuracy can be advantageously obtained from densimeter processor 50 than that obtainable in the art.

Now, at this point with flow calibration having been completed execution proceeds to block 961 to calculate the numerator of equation (17) for use in calculating the density of whatever fluid is currently flowing through the meter. Once the numerator has been calculated, its value is temporarily stored in memory as variable N. The value of $tc_m T_m^2$ will be that for whatever fluid is currently flowing through meter assembly 10. In the event the meter is being calibrated and either air or water is flowing therethrough, then the density of either air or water, respectively, will be subsequently calculated and displayed. The displayed density value can be visually compared against the value that was just entered to serve as a useful check on meter operation. Alternatively, if an unknown fluid is flowing therethrough, then its density will be subsequently calculated and displayed.

Execution then proceeds to decision block 964 which tests the sign of the value of the numerator, N. In the event this sign is negative, then block 967 is executed to set the value of an appropriate flag, here DENSSIGN, to an appropriate value, here the hex value "FF". Thereafter, execution proceeds to block 969. Alternatively, if the sign of the value of N is positive after block 967 has been executed, execution proceeds directly to block 969. This block, when executed, calculates the first term in equation (17), i.e. by multiplying the density difference, delta d, by the value of the numerator, N, and thereafter dividing by the value of the denominator, D. The resulting value is temporarily stored in memory 547 see FIG. 5) as the intermediate density value, $d_{int}$.

Once the intermediate density value has been stored, execution proceeds, as shown in FIG. 9C, to decision block 972 which tests the sign of this value. Execution is passed to block 977 if the sign is positive—i.e. the value of DENSSIGN equals "00", or to decision block 975 if the sign is negative—i.e. the value of DENSSIGN equals "FF". Block 977, when executed, calculates the value of the density of the fluid being measured, $d_m$, by adding the value of air density, $d_a$, previously stored during calibration, to the intermediate density value, $d_{int}$. Alternatively, if execution passes to decision block 975, then this block determines whether the magnitude of the value of the density of air, $d_a$, is greater than that of the intermediate density value. Inasmuch as density can never be a negative number, should this decision block determine that a negative value for $d_m$ will result, then execution passes, via the YES path from decision block 975, to execution block 982. This execution block calculates the value $d_m$ by subtracting the intermediate density value from the air density value. If on the other hand, the density value $d_m$ will not be negative, execution passes to execution block 979 which calculates the value of $d_m$ by subtracting the air density value from the intermediate density value. Once the density value $d_m$ has been calculated by block 977, 979 or 982, execution then passes to block 984. In the event the operator has instructed the metering system to provide density values in a desired unit other than specific gravity (e.g. brix, pounds/cubic foot, pounds/barrel), then this block multiplies the density value $d_m$, which is generated in specific gravity units by equation (17), by an appropriate scaling factor and then stores the scaled result as density value, $d_m$. If specific gravity units have been selected, no scaling is performed on density value $d_m$ by block 984.

Once these operations have been accomplished, execution passes to decision block 985. In the event the inventive system is not being used as a net oil computer, then execution passes from the NO path of this decision block to decision block 987 to update the density and temperature outputs and displays.

Alternatively, if the system is being used as a net oil computer, then execution proceeds to block 986. This block executes DRT parameter calculation and transmission routine 1000, which will be discussed shortly in detail in conjunction with FIG. 10. This routine, in essence, calculates various parameters, including a mass to volume conversion factor, temperature compensated density values for crude oil and saltwater, and water cut and oil cut density ratios. Once these parameters have been calculated, this routine then causes several of these parameters to be serially transmitted by serial interface 551 (see FIG. 5) over serial communication lines 22 to digital rate totalizer and display (DRT) 60 (shown in FIG. 6). Thereafter, as shown in FIGS. 9C and 9D, execution passes to block 987.

Now, at this point, all that remains for execution within 20msec interrupt routine 900 is to update the temperature and density displays, and update the temperature and density 4-20 mA analog outputs with current values of tube temperature and measured density. To prevent flicker, the analog displays are updated every 400 milliseconds, or at the conclusion of 20 iterations (passes) through the 20 msec interrupt routine. The 4-20 mA analog outputs are updated at the conclusion of each iteration, i.e. at 20 millisecond intervals. To perform this updating, execution first proceeds to decision block 987. This block determines whether twenty iterations of interrupt routine 900 have occurred, i.e. whether the current contents of pass counter, m, equals 20. If so, then execution proceeds, via the YES path from decision block 987 to block 9B. This latter block provides new values of tube temperature and measured density to display controller 571 (see FIG. 5) to appropriately update both displays. Thereafter, as shown in FIG. 9D, control passes to block 992 which resets the contents of the pass counter, m, to zero. Execution now passes to block 994 which updates the 4-20 mA analog outputs for tube temperature and density by providing new values to timers 561 and 563 (see FIG. 5), respectively. Execution also passes to block 994 to update these outputs if the contents of the pass counter have as not reached 20, namely via the NO path from decision block 987. This now concludes the density measurements and hence execution returns to main program 700.

Figure 10:
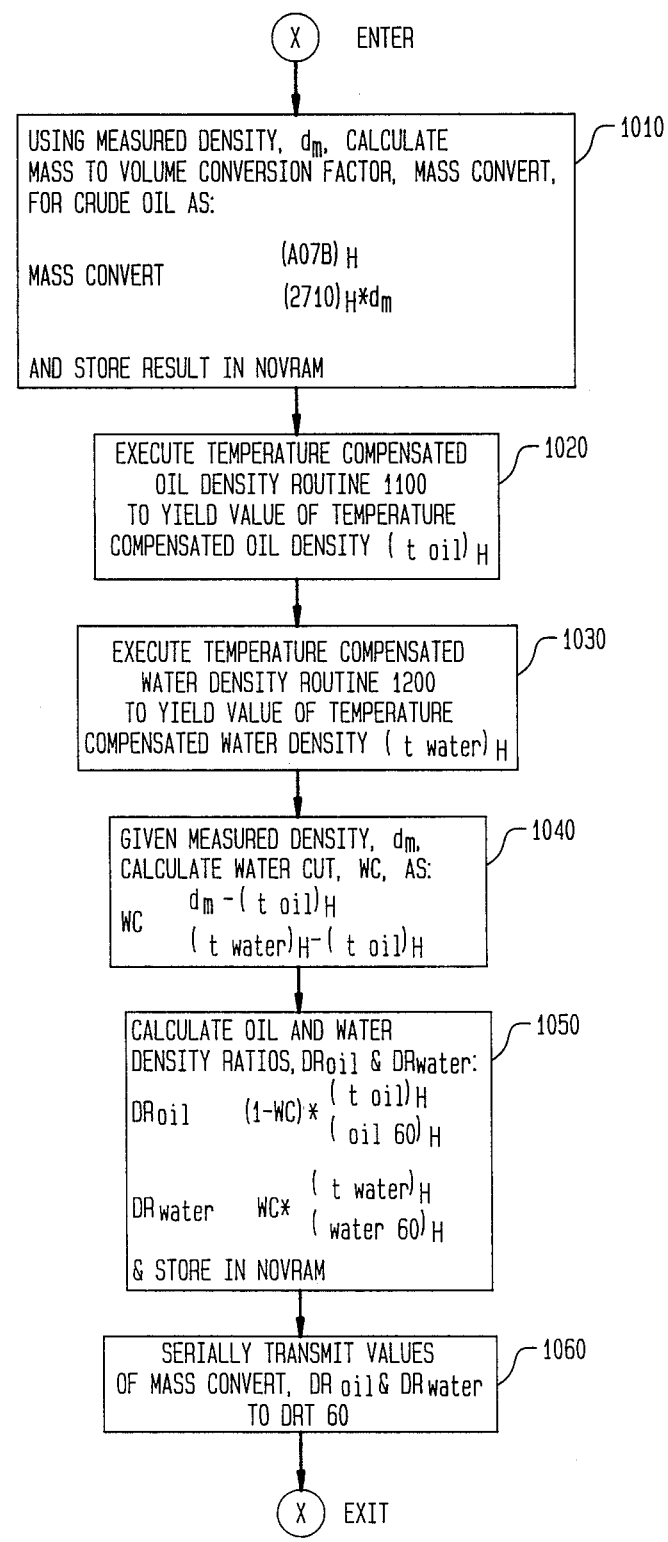
FIG. 10 depicts a flowchart of DRT Parameter Calculation and Transmission Routine 1000 that is executed as part of 20 msec Interrupt Routine 900 shown in FIGS. 9A-9D.

A flowchart of DRT parameter calculation and transmission routine 1000 is depicted in flowchart form in FIG. 10. As noted, this routine is only executed if the inventive system is being used as a net oil computer. The purpose of this routine, as discussed above, is twofold: first, to calculate the value of various parameters, such as, a mass to volume conversion factor for oil, temperature compensated density values for crude oil and saltwater and water and oil cut density ratios for oil and saltwater; and, second, to serially transmit the value of each of these parameters from densimeter processor 50 to DRT 60.

Upon entry into routine 1000, execution proceeds to block 1010. This block calculates a ratio (MASS CONVERT) that converts mass in terms of pounds/minute into volume in terms of standard barrels (42 gallons)/day. This ratio is given by the following equation:

$$\text{MASS CONVERT} = \frac{A07B_H}{2710_H \, d_m} \quad (18)$$

where:
A07B and 2710 are hexidecimal constants; and
$d_m$ is the density of the fluid as measured by densimeter processor 50.

The value of this ratio is then stored by the densimeter processor within the NOVRAM resident within memory 547 (see FIG. 5). At this point, routine 1000 will now determine temperature compensated density values for both water and oil. To do so, as shown in FIG. 10, execution proceeds to blocks 1020 and 1030. Inasmuch as the densities of crude oil and saltwater change with temperature, these blocks compensate reference densities for oil and water, i.e. $\text{rho}_{oil\ 60}$ and $\text{rho}_{water\ 60}$, for any changes in temperature as measured by the densimeter processor by executing temperature compensated oil density routine 1100 and temperature compensated water density routine 1200 in seriatim. The reference densities are previously obtained by using a laboratory densimeter to separately measure the densities of a sample of oil and a sample of water both taken from the flow stream and held at 60 degrees Fahrenheit (F.) during the respective measurements. Thereafter, execution block 1040 calculates the value of the water cut, WC which is the proportionate amount of the total volumetric flow of the oil-water emulsion attributable to water. The formula implemented within block 1040 is:

$$WC = \frac{d_m - (\text{rho}_{t\ oil})H}{(\text{rho}_{t\ water})H - (\text{rho}_{t\ oil})H} \quad (19)$$

where: $(\text{rho}_{t\ oil})H$ and $(\text{rho}_{t\ water})H$ are hexidecimal values of the temperature compensated reference densities for crude oil and saltwater.

Next, given the value of the water cut, block 1050 is executed to calculate the oil and water cut density ratios, $DR_{oil}$ and $DR_{water}$, i.e. the proportionate amount of the measured emulsion density attributable to the oil and water components, respectively. These ratios are given by the following equations:

$$DR_{oil} = (1 - WC)\frac{(\text{rho}_{t\ oil})H}{(\text{rho}_{oil\ 60})H} \quad (20)$$

$$DR_{water} = WC\frac{(\text{rho}_{t\ water})H}{(\text{rho}_{water\ 60})H} \quad (21)$$

where:
($\text{rho}_{oil\ 60})_H$ and $60)_H$ are hexidecimal values of the reference densities for crude oil and saltwater, respectively, taken at 60 degrees F. and measured in grams/cubic centimeter.

Now, at this point, execution passes to block 1060. This block serially transmits the values of three parameters, MASS CONVERT, $DR_{oil}$ and $DR_{water}$, through serial interface 551 (see FIG. 5) to DRT 60. Upon receipt of any incoming serial information, DRT 60 executes serial input interrupt routine 1400 (discussed below in conjunction with FIG. 14) which accepts this serial information and stores the values of these parameters, after they have been completely received, in NOVRAM resident within the DRT. Execution then exits from routine 1000.

As noted above, Temperature Compensated Oil Density Routine 1100 compensates the reference density of crude oil measured at 60 degrees F. (measured in grams/cubic centimeter) for the actual temperature of the flow stream traveling through meter assembly 10 (see FIG. 1). The general equation used to perform this compensation is:

$$\text{rho}_{t\ oil} = \text{rho}_{oil\ 60}\ e^{[-a^*delta\ t(1-.8^*a^*delta\ t)]} \quad (22)$$

where:
  delta t is measured temperature −60 (in fahrenheit); and fahrenheit; and $$a = \frac{3.1410957 \times 10^{-4}}{\text{rho}_{oil\ 60}}$$

To simplify processing, equation (22) can be accurately approximated by a second order polynomial obtained through a well known Taylor series expansion. In addition, values of the reference densities are entered into the inventive system in five digit integer units i.e. the actual value multiplied by 10,000), and temperature is measured in 0.05 degree C. increments. Therefore, equation (22) can be re-written as follows:

$$2710_H * \text{rho}_{t\ oil} = \text{rho}_{oil\ 60} * [2710_H - A - (0001F7_H)^* A^2] \quad (23)$$

where:
  $.0001F7_H$ = hexidecimal value .0001F7; and $$A = \frac{(1D46C.75_H)(t_{a/d} - 138_H)}{(2710_H)(\text{rho}_{oil\ 60})/256} \quad (24)$$

where:
  $t_{a/d}$ is the RTD temperature in centigrade measured by A/D converter 537 (see FIG. 5) located within densimeter processor 50; and
  $1D46C.75_H$ and $138_H$ are the hexidecimal values 1D46C.75 and 138.

Equations (23) and (24) are implemented within Temperature Compensated Oil Density Routine 1100.

Figures 11, 11A:
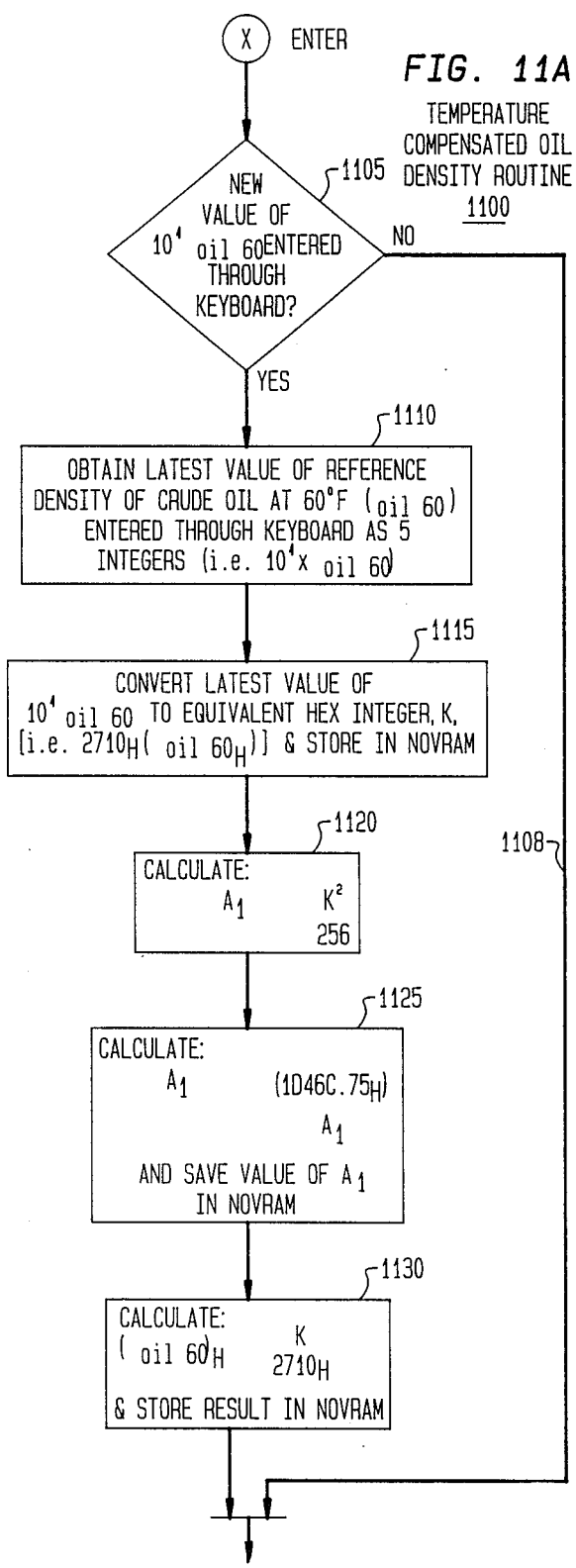
FIG. 11 is a diagram showing the correct alignment of the drawing sheets for FIGS. 11A-11C.
FIGS. 11A-11C collectively depicta flowchart of Temperature Compensated Oil Density Routine 1100 which is executed as part of DRT Parameter Calculation and Transmission Routine 1000, shown in FIG. 10.
Figure 11B:
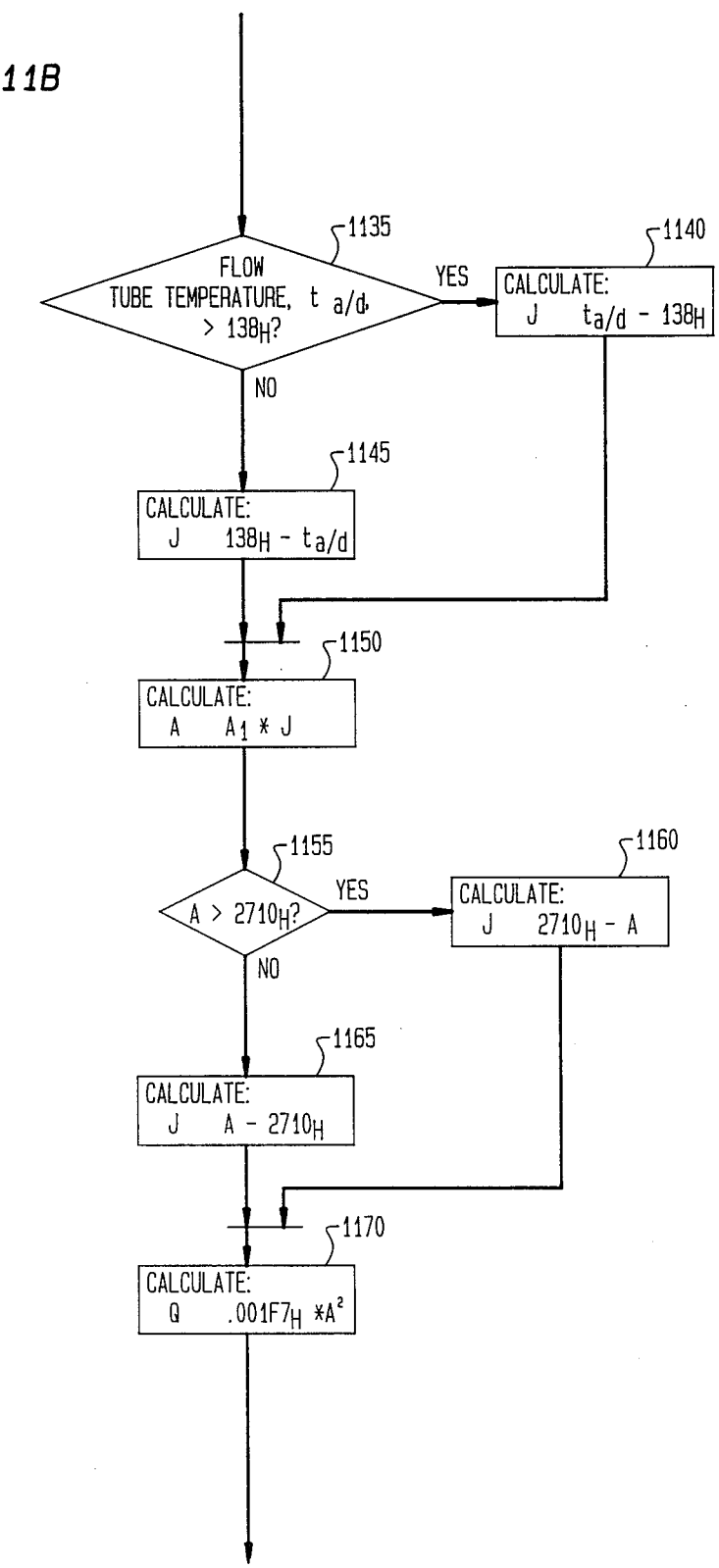
Figure 11C:
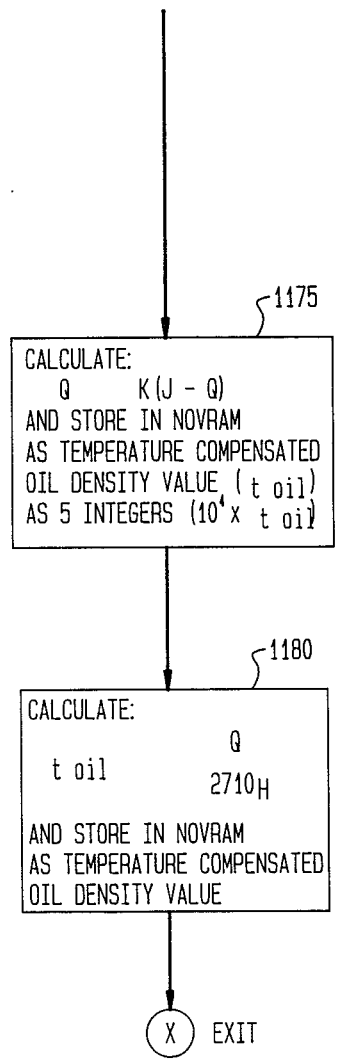

A flowchart of routine 1100 is depicted in flowchart form in FIGS. 11A–11C, with the correct alignment of the drawings sheets for these figures shown in FIG. 11. Upon entry into this routine, execution proceeds to decision block 105. This block tests whether the user has entered a new value of the reference oil density ($\text{rho}_{oil\ 60}$ times 10,000) into the inventive system. If not, the most recently entered value is read from NOVRAM and compensated for the actual temperature of the flow stream, in a manner discussed below in conjunction with blocks 1135 through 1180. Alternatively, i f a user has entered a new value for the reference oil density, then execution proceeds to block 1110. This block, when executed, obtains the latest five digit integer value of the reference oil density that has been entered through the keyboard. Thereafter, this reference value is first converted into hexidecimal integer form by block 1115 to yield integer K and thereafter stored within the NOVRAM located within the densimeter processor. Execution then proceeds to block 1120 which squares the hexidecimal integer K and divides by 256. The resulting value is then divided into the hex integer, 1D46C.75 by block 1125 with the result of this division then being stored in NOVRAM as an intermediary value, $A_1$. Then, block 1130 is executed to calculate the reference value of $\text{rho}_{oil\ 60}$ by dividing the five digit value for this quantity that was entered through the keyboard by hex 2710 (10,000 base 10) and then to store the result in NOVRAM for future use. At this point, execution proceeds to blocks 1135–1175 which collectively calculate the remainder of equation (24) and then equation (23). Specifically, decision block 1135 is executed, via block 1130 or NO path 1108 which emanates from decision block 1105. Decision block 1135 tests whether tho-difference between the temperature measured through the A/D converter ($t_{a/d}$) and the value $138_H$ is negative or positive. In either event, a positive difference, J, is formed by routing execution to either block 1140 or 1145 depending upon the outcome of the test performed by decision block 1135. Thereafter, block 1150, when executed, multiplies the difference by the intermediary value $A_1$ and temporarily stores the result within RAM as the value A for subsequent use in calculating equation (24). Now, to calculate this equation, execution proceeds to decision block 1155. This block tests whether the difference between the two largest subtractive terms appearing within the equation will be positive. Inasmuch as density is always a positive number, decision block 1155 routes execution to either block 1160 or 1165 to ensure that the difference, J, will be positive. Once this occurs, execution proceeds to block 1170 which calculates the second order term in this equation. The remainder of equation (24) is calculated by blocks 1175 and 1180. The results produced by blocks 1175 and 1180 are stored in NOVRAM for subsequent use as the temperature compensated reference oil density, $\text{rho}_{t\ oil}$, in five digit integer form, and in decimal form, respectively. Upon completion of block 1180, execution exits from routine 1100.

As noted above, Temperature Compensated Water Density Routine 1200 compensates the reference density of the saltwater measured at 60 degrees F. (measured in grams/cubic centimeter) for the actual temperature of the flow stream flowing through meter assembly 10 (see FIG. 1). The general equation used to perform this compensation is:

$$\text{rho}_{t\ water} = \text{rho}_{water\ 60} - 1.1872 \times 10^{-4}\ (\text{delta t}) - 1.004 \times 10^{-6}\ (\text{delta t})^2 \quad (25)$$

Inasmuch as reference density values are entered into system in five digit integer units (i.e. the actual value multiplied by 10,000) and temperature is measured in 0.05 degree C. increments, equation (25) can be re-written as follows:

$$2710_H * \text{rho}_{t\ water} = 2710_H * \text{rho}_{water\ 60} - .1B5A64_H * (t_{a/d} - 138_H) - .000554_H * (t_{a/d} - 138_H)^2 \quad (26)$$

Figures 12, 12A:
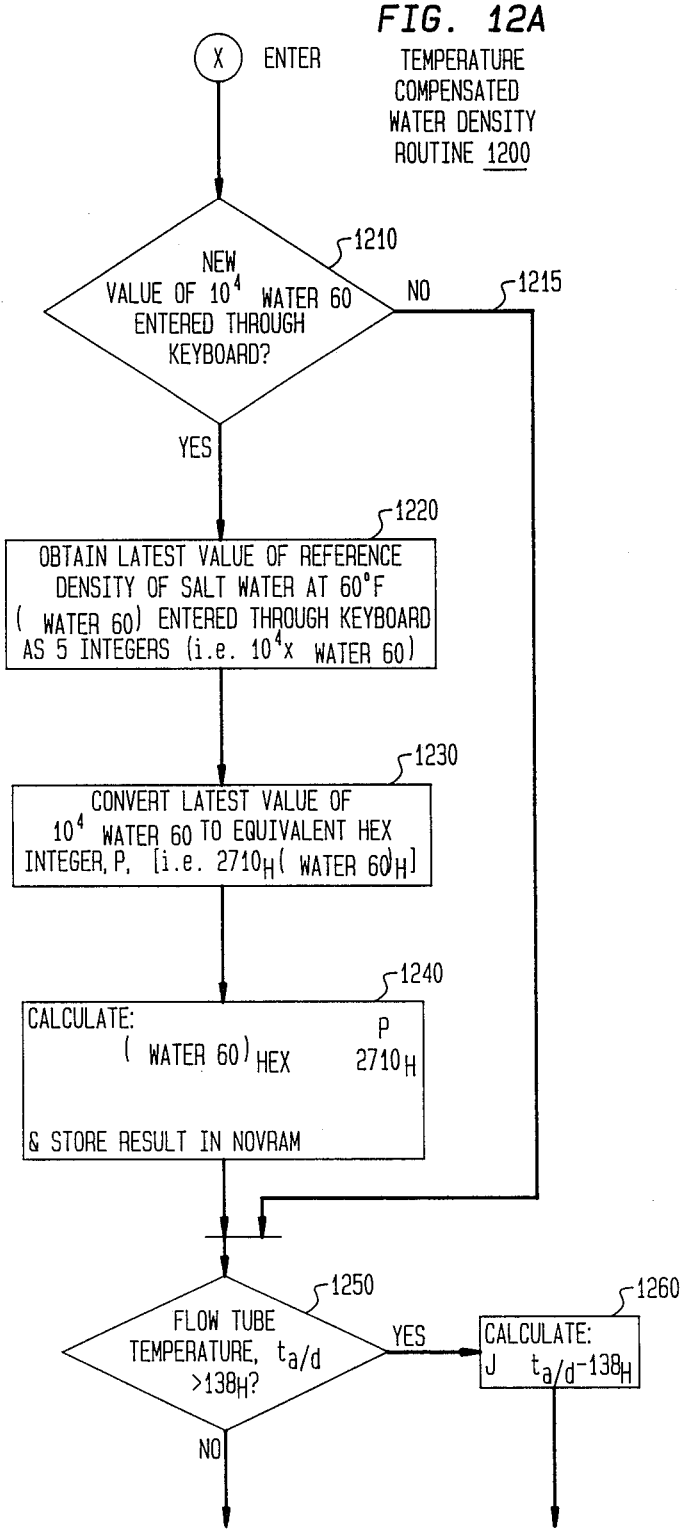
FIG. 12 is a diagram showing the correct alignment of the drawing sheets for FIGS. 12A and 12B.
FIGS. 12A and 12B collectively depict a flowchart of Temperature Compensated Water Density Routine 1200 which is also executed as part of DRT Parameter Calculation and Transmission Routine 1000, shown in FIG. 10.
Figure 12B:
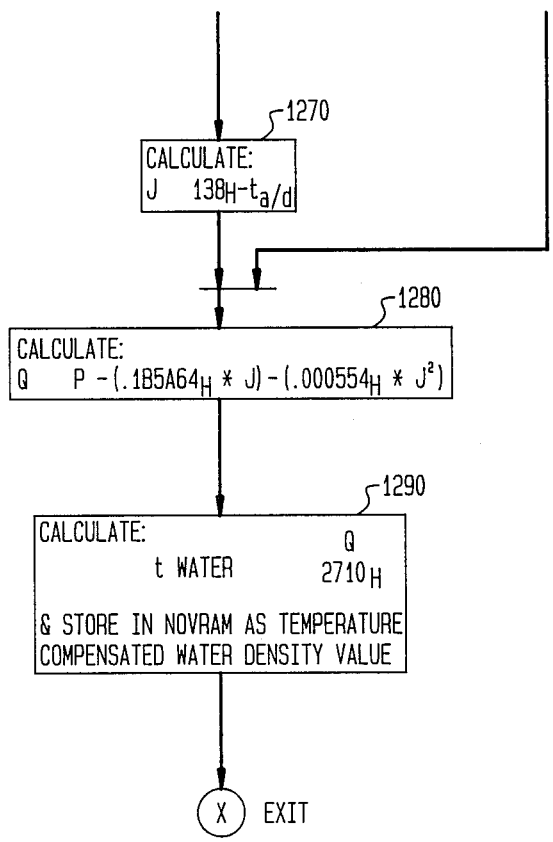

A flowchart of routine 1200 is depicted in flowchart form in FIGS. 12A–12B, with the correct alignment of the drawings sheets for these figures shown in FIG. 12. Upon entry into this routine, execution proceeds to decision block 1210. This block tests whether the user has entered a new value of the reference water density ($\text{rho}_{water\ 60}$ times 10,000) into the inventive system. If not, the most recently entered value is read from NOVRAM and compensated for the actual temperature of the flow stream, in a manner discussed below in conjunction with blocks 1250 through 1290. Alternatively, if a user has entered a new value for the reference water' density, then execution proceeds to block 1220. This block, when executed, obtains the latest five digit integer value of reference water density that has been entered through the keyboard. Thereafter, this reference value is first converted into hexidecimal integer form by block 1230 to yield integer P and thereafter stored within the NOVRAM located within the densimeter processor. Block 1240 is then executed to calculate the reference value of $\text{rho}_{water\ 60}$ by dividing the five digit value for this quantity that was entered through the keyboard by hex 2710 (10,000 base 10) and then to store the result in NOVRAM for future use. At this point, execution proceeds to decision block 1250 which is also executed, via NO path 1215 which emanates from decision block 1210. Decision block 1250 tests whether the difference between the temperature measured through the A/D converter ($t_{a/d}$) and the value $138_H$ is negative or positive. In either event, a positive difference, J, is formed by routing execution to either block 1260 or 1270 depending upon the outcome of the test performed by decision block 1250. At this point, equation (25) is calculated by blocks 1280 and 1290. The results produced by blocks 1280 and 1290 are stored in NOVRAM for subsequent use as the temperature compensated reference water density, $rho_{t\ water}$ in five digit integer form, and in decimal form, respectively. Upon completion of block 1290, execution exits from routine 1200.

D. Digital Rate Totalizer and Display Circuit 60

This discussion will now turn to a detailed explanation of digital rate totalizer and display circuit (DRT) 60. The hardware that constitutes the DRT is shown in block diagram form in FIG. 6. The software executed by this hardware will be discussed later in conjunction with FIGS. 13, 14 and 15A-15E.

1. DRT Hardware

Figure 6:
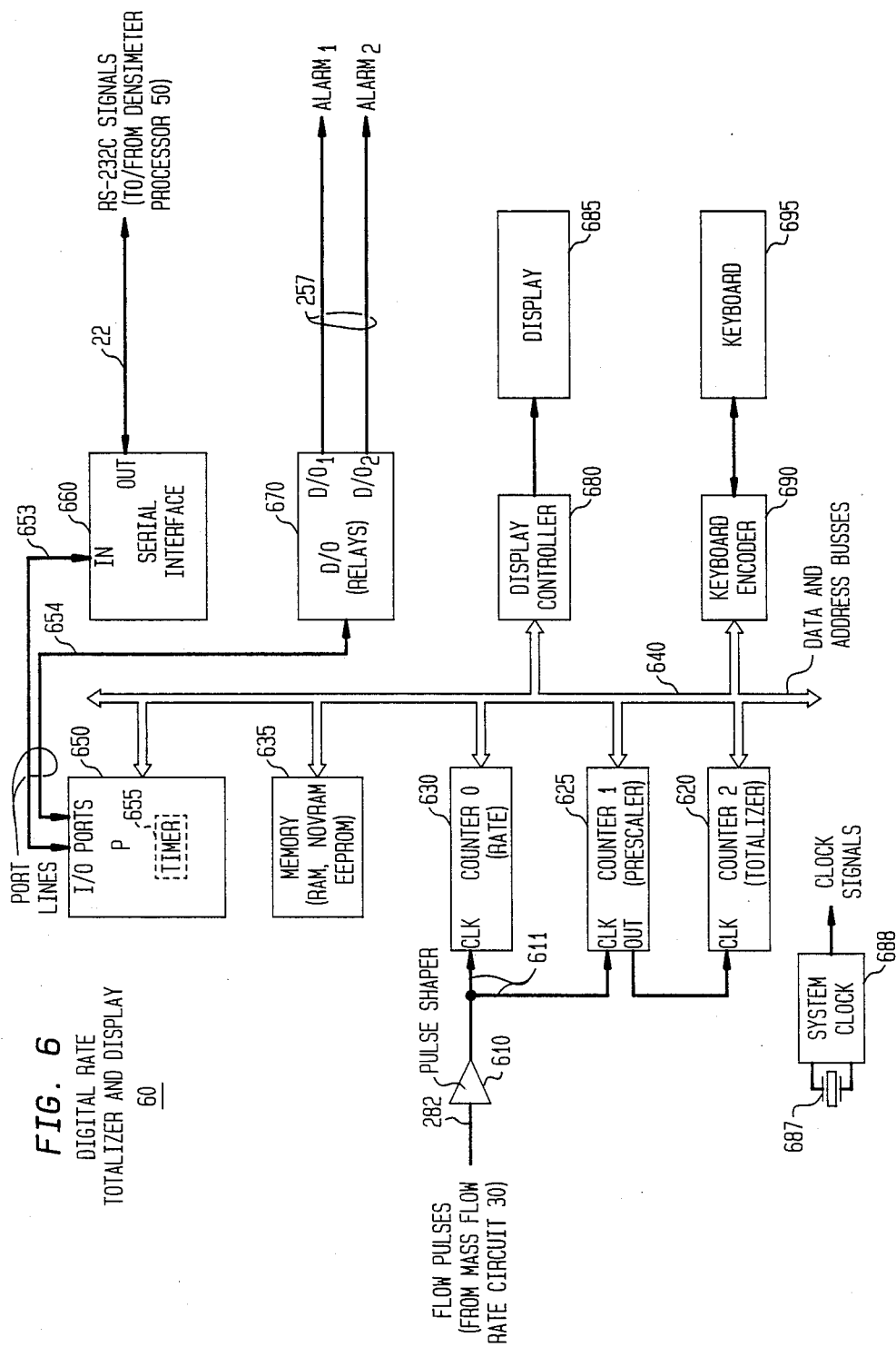
FIG. 6 is a block diagram of the hardware that constitutes Digital Rate Totalizer and Display Circuit (DRT) 60, also shown in FIG. 2.

The hardware that forms the DRT is depicted in block diagram form in FIG. 6. As shown, DRT 60 receives mass flow rate measurements, in scaled frequency form over lead 282, from mass flow rate circuit 30 located within mass flow rate electronics 100 and various parameters, as discussed above, calculated by and serially transmitted over serial communication lines 22 by densimeter processor 50 situated within densimeter electronics 200 (see FIG. 2) Digital rate totalizer and display 60 then calculates volumetric flow rate and totalized volumetric flow measurements for each component in a multi-component fluid stream. Hence, and as noted above, whenever the inventive meter is used to measure an oil-water flow stream, the system advantageously becomes a net oil computer.

Suitable contact closures are provided, as the $alarm_1$ and $alarm_2$ outputs, over leads 257 for indicating desired alarm conditions. These conditions are programmed in software and may include, for example, a volumetric flow rate that either exceeds a maximum setpoint or is less than a minimum setpoint.

Specifically, given the measured oil-water emulsion density value along with various constants previously entered by the user (such as the reference crude oil and saltwater densities at 60 degrees F.), densimeter processor 50, as noted above, calculates various parameters: a mass to volume conversion factor, and oil and water density ratios. These three parameters are then serially transmitted by the densimeter processor to DRT 60. The DRT then uses these parameters along with the measured mass flow rate for the oil-water flow stream, provided by mass flow rate circuit 30, to separately calculate the volumetric flow rate (in, for example, standard barrels/day) of the entire flow stream and of the water and oil components. Thereafter, the DRT separately totalizes these volumetric flow rates to yield totalized volumetric flow measurements of the entire emulsion and of the water and oil components. The volumetric flow and totalized flow measurements for the entire emulsion or either the water or oil components can be separately displayed. Also, as set forth below, DRT 60 possesses the capability to separately calculate the mass flow rate for the entire emulsion and for the water and oil components and also provide corresponding totalized mass flow values as well. The mass flow rate and totalized mass flow for the entire emulsion or either the water or oil components may also be selectively displayed.

In particular, as shown in FIG. 6, the DRT is a 8-bit microprocessor based system. The system illustratively contains common bi-directional address and data busses 640 that link counters 620, 625 and 630; memory 635; 8-bit microprocessor 650; display controller 680 and keyboard encoder 690. Appropriate clock signals are provided by system clock circuit 688 which sets its time base from oscillations produced by crystal 687.

Incoming pulses from mass flow rate circuit 30 appearing over lead 282 are shaped (squared) by pulse shaper 610 and applied to counters 625 and 630. These pulses represent the mass flow rate having an illustrative scaling factor of 0–100 pounds/minute corresponding to 0–10,000 Hz. Counter 630 totalizes these pulses to provide a mass flow measurement and is read every 0.5 second by microprocessor 650. Counter 625 divides (prescales) the flow pulses by a known factor, such as 60, 600, 3600 to provide flow rate in terms of a conveniently large time unit such as seconds, minutes or hours for use in subsequent totalization by counter 620. The contents of each of these three counters can be read by microprocessor 650.

Memory 635 contains random access memory (RAM) for temporary data storage, erasable programmable read only memory (EEPROM) for program storage and non-volatile RAM (NOVRAM) which advantageously maintains various values in the event of a power failure. In particular, the NOVRAM stores: the values of the three parameters supplied by densimeter processor 50; separate totalized volumetric flow measurements for the emulsion, and the oil and water components; and other system constants used by the DRT, such as the baud rate for serial circuitry located within microprocessor 650 and the prescaling constant for counter 625. New values for the three parameters are written into the NOVRAM every time these parameters are calculated by the densimeter processor and received by the DRT, i.e. every 20 milliseconds. All the totalized values are updated in NOVRAM immediately after they are calculated Microprocessor 650 contains internal timer 655, Which is set, early into the execution of main program 1300 (see FIG. 13 which is discussed in detail later), to time out every 20 milli-seconds and generate an interrupt. This interrupt causes the microprocessor to execute 20 msec interrupt routine 1500 (see FIGS. 15A-15E). The serial interface provides a serial communication path over serial communication lines 22 with densimeter processor 50 (see FIG. 5). The microprocessor can also enable or disable selected alarm outputs, by placing an appropriate signal on its I/0 port lines and via leads 654, to digital output circuit 670.

Serial interface 660, as shown in FIG. 6, transmits information from microprocessor 650 in RS-232C serial form over serial communication lines 22. To provide this function, microprocessor 650 serially applies a byte of information at a time, via leads 653 from its I/0 ports, to serial interface 660. The serial circuitry within microprocessor 650 is programmed with an appropriate baud rate during execution of main program 1300, as described below For purposes of the present embodiment, serial interface 660 is only used to receive data over serial communication lines 22 from densimeter processor 50; while serial interface 551 (located in densimeter processor 50 shown in FIG. 5 is only used to transmit data over these leads. Serial interface 660 functions in a similar though reverse manner to serial interface 551 and is a generally a line driver/line receiver pair that provides an appropriate interface to serial communication lines 22.

Display 685, as shown in FIG. 6 and typically a pair of well known liquid crystal displays, continuously displays volumetric flow rate and totalized volumetric flow for any one of three items, as selected by the user: the entire oil-water flow stream, the oil component or the water component. The microprocessor updates the totalized flow display every 20 milliseconds and the flow rate display every 500 milliseconds. At these times, new data is placed by the microprocessor on the data bus that forms part of busses 640 and is thereafter loaded into the display controller 680 which, in turn, control operation of displays 685. Regardless of which particular item is being displayed, the microprocessor continuously totalizes the volumetric flow for all three items.

During the operation of the inventive system, an operator can enter commands through keyboard 695, such as to select various items for display. Under the control of microprocessor 650, keyboard encoder 690 scans the keyboard every 20 milliseconds and applies incoming information onto the data bus that forms part of busses 40.

2. DRT Software

The discussion will now proceed with a detailed explanation of the software executed by DRT 60. This software is basically interrupt driven. A flowchart of main program 1300 is shown in FIG. 13. Serial input interrupt routine 1400 and 20 msec interrupt routine 1500, which are also both executed by the DRT, are respectively shown in FIGS. 14 and 15A–15E. To facilitate understanding, the reader should also simultaneously refer to FIG. 6 during the following discussion of the DRT software.

As shown in FIG. 13, upon entry into main program 1300, block 1310 is executed. This block configures and initializes the microprocessor system in the DRT. Specifically, this block configures the microprocessor to access the EEPROM located within memory 635 (see FIG. 6). Thereafter, block 1310 shown in FIG. 13 establishes a software map which maps all the other bus devices, such as counters 620, 625 and 630; and display controller 680, into appropriate RAM locations. Once these tasks have been completed, this block performs various diagnostics and memory checks and also resets various memory locations, such as those used for temporary data storage and flags, to zero. Thereafter, execution passes to block 1320. Here, this block accesses various constants from NOVRAM, such as the scale factor for counter (prescaler) 625, the baud rate for the serial circuitry located within the microprocessor and, where appropriate, the decimal point location, and reads these constants into RAM memory. To save execution time, the microprocessor only performs integer arithmetic and therefore needs to monitor the location of the decimal point for calculation and display purposes. At this point, execution passes to block 1330. This block when executed, programs counter 625 with the scale factor and also programs the serial circuitry within microprocessor 650 with the baud rate. Once this has occurred, execution passes to block 1340. Upon execution of this block, the microprocessor programs counters 620 and 630 to be down counters and also loads these counters with the value "FFFF". Two memory locations, "OLDCOUNT0" and "OLDCOUNT2", which are used in conjunction with these counters as described in detail below, are also set the value "FFFF". Now, block 1350 is executed which programs timer 645 located within microprocessor 650 to time out every 20 milliseconds and generate an interrupt. Next, block 1360 is executed which unmasks all interrupts to the microprocessor.

From this point on, main program 1300 merely waits for an interrupt to occur, then processes the interrupt and finally re-enters a wait state. To illustrate these steps, execution is shown as passing to decision block 1370 which continually re-executes unless an interrupt occurs. When an interrupt occurs, execution passes to block 1380 wherein the interrupt will be serviced by a particular routine depending upon which interrupt occurs. Interrupts can occur from two sources: whenever the microprocessor detects incoming serial data, and the 20 millisecond timer. Each interrupt invokes a corresponding service routine: serial input interrupt routine 1400 shown in FIG. 14 for incoming serial information, and 20 msec interrupt routine 1500 shown in FIGS. 15A–15E for the 20 millisecond timer. Execution of serial input interrupt 1400 transfers the incoming serial information from the serial circuitry contained within the microprocessor into RAM memory 635 for subsequent processing. Execution of 20 msec interrupt routine 1500 causes the DRT to calculate the volumetric flow rate and totalized volumetric flow and then update the totalized values stored in ,NOVRAM. At the conclusion of either interrupt servicing routine, execution returns to decision block 1370 to await the occurrence of the next interrupt.

Figure 14:
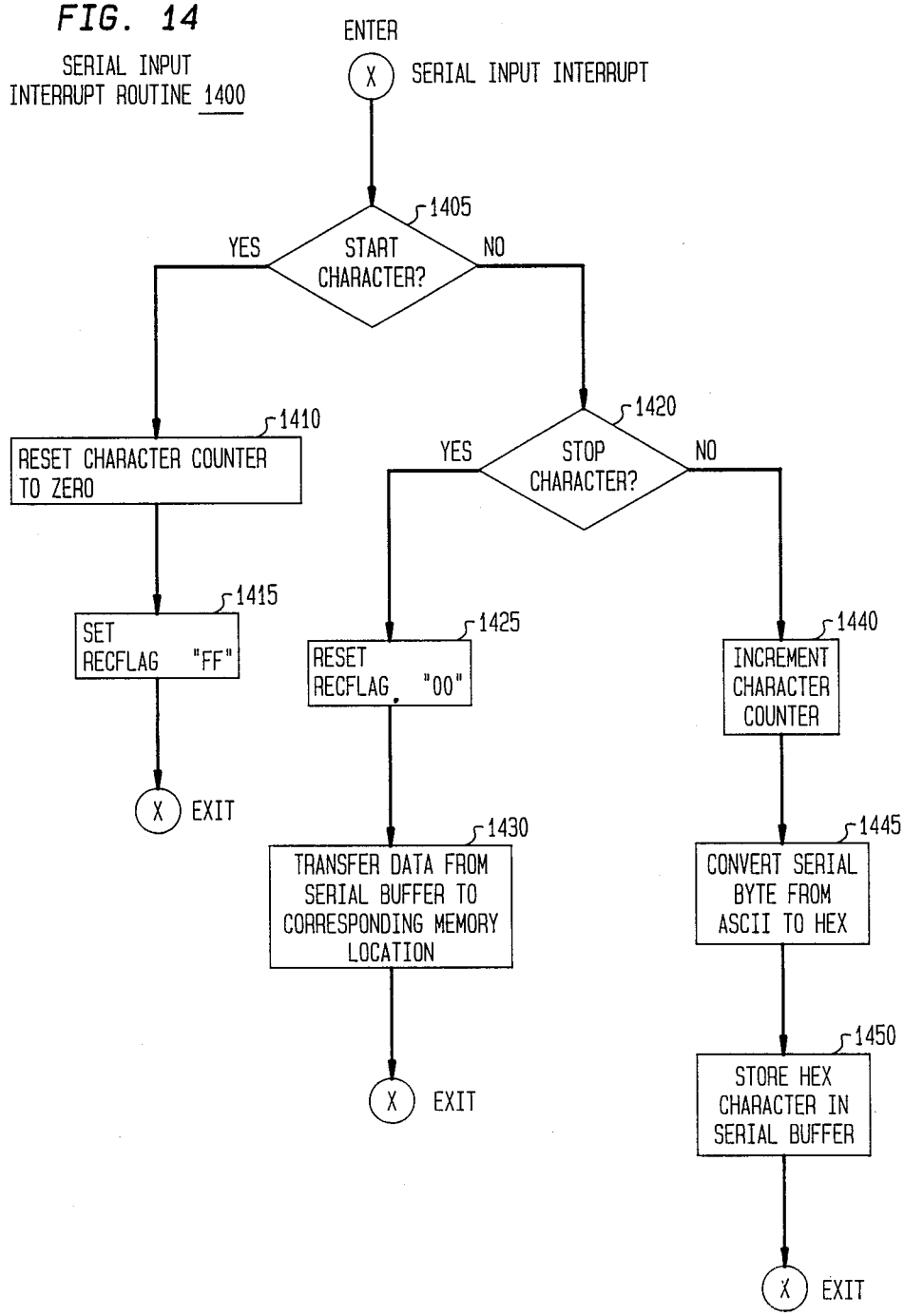
FIG. 14 is a flowchart of Serial Input Interrupt Routine 1400 which is also executed by DRT 60.

A flowchart of serial input interrupt routine 1400 is shown in FIG. 14. In the event densimeter processor 50 (see FIG. 5) needs to initiate a serial data transfer to DRT 60, the densimeter processor will first place a high level on a "request to send" lead (well known and not specifically shown) which forms one of serial communication lines 22. Once this occurs, serial interface 660 see FIG. 1, if it is not already receiving serial data, will place a high level on "clear to send" lead (also well known and not specifically shown) which forms another one of serial communication lines 22. Shortly thereafter, the microprocessor located in the densimeter processor will, through its serial interface, serially transmit a character via serial interface 660 to microprocessor 650 located within the DRT. Once the character is received, microprocessor 650 generates a serial input interrupt. At this point, execution of serial input interrupt routine 1400 begins. As shown in FIG. 14, execution first passes to decision block 1405. The serial communication used by these microprocessors uses a simple start/stop protocol to serially transfer data therebetween. Hence, in the event the received character is a "start" character, then execution proceeds, via the YES path from this decision block, to block 1410. This block resets a character counter to zero. Next, block 1415 is executed to set an appropriate flag, RECFLAG, to the value "FF". This flag is read by the microprocessor to indicate that it is receiving data through its serial circuitry. Execution then exits from this interrupt routine but will re-enter it whenever the next serial character is received through serial interface 660. Alternatively, in the event the received serial character is not a "start" character, then execution passes to decision block 1420 which tests this character to determine if it is a "stop" character. If the received character is not a "stop" character, then execution proceeds down the NO path from decision block 1420 to block 1440. This block, when executed, increments the character counter. This counter is used by the microprocessor to monitor the number of incoming characters and thereby determine whether an entire item of data has been received and, if so, to initiate further storage and/or processing of this data. If all the expected number of characters has not received, then the microprocessor will ignore this item of incoming data. Thereafter, execution proceeds to block 1445 which converts the received serial character from ASCII to hexadecimal (hex) form. Next, block 1450 enters the resulting hex character into a serial buffer located within RAM memory. At this point, execution exits from this interrupt routine and will re-enter this routine whenever the next serial character is received through serial interface 660. Lastly, in the event the received character is a "stop" character which indicates that all the characters that form a particular data item have been received, then execution proceeds, via the YES path from decision block 1420, to block 1425. This block resets the value of the receive flag, RECFLAG, to "00" thereby indicating the microprocessor is no longer receiving serial data and hence that its serial circuitry is not busy. Block 1430 is then executed to transfer the entire data item, in hex form, (such as the mass to volume conversion factor or oil cut density ratio produced by the densimeter processor) from the serial buffer in RAM to a corresponding memory location in NOVRAM that has been assigned to this data item. Thereafter, execution exits from this routine.

A flowchart of 20 msec interrupt routine 1500 is shown in FIGS. 15A-15E. Upon entry into this routine, execution begins with block 1502. This block, when executed, enables the serial input interrupt such that it can be serviced during execution of the 20 msec interrupt routine. This nesting of interrupts is necessary to ensure that incoming serial characters are processed by the microprocessor as soon they are received. Execution now proceeds to block 1504 which decrements the value stored in pass counter N by one. The pass counter is initially loaded with the value "25" and decremented by one each time 20 msec interrupt routine 1500 is executed. Hence, the contents of the pass counter will reach zero every 0.5 second. The volumetric flow rate display is updated every 0.5 second to minimize flicker. To provide this updating, decision block 1506 tests whether the value of the pass counter equals zero. In the event the pass counter equals zero, then execution proceeds, from the YES path of the decision block, to ½ second displayed rate update routine 1510. This routine calculates the present volumetric flow rate of either the entire emulsion, or the oil or water component—as selected by a user—and updates the display with the result. At the conclusion of update routine 1510, execution proceeds to totalizer and display routine 1560. Execution also passes to this routine, via NO path 1507, from decision block 1506. As a result, routine 1560 executes every 20 milliseconds. In particular, this routine calculates the volumetric flow that has occurred during the preceding 20 millisecond interval for the entire emulsion and for the water and oil components. These flow values are then continually added to corresponding totalized flow values previously stored in NOVRAM to produce current totalized flow values which are, in turn, stored back into NOVRAM. Once this has occurred, routine 1560 displays whichever one of these three totalized volumetric flow values has been selected by the user. Whenever totalizer and display routine 1560 finishes executing, execution then exits from 20 msec interrupt routine 1500.

As noted, ½ second displayed rate update routine 1510 calculates one of three volumetric flow rates (the emulsion, r the oil or water component) and updates the rate display with the result. In essence, this routine calculates the mass flow rate (i.e. total mass flow/second) by totalizing the individual mass flow pulses that occur every 0.5 second and combining the totalized value with the totalized value that was generated during the preceding 0.5 second. The resulting combined value directly represents mass flow per second. Hence, a new combined reading is generated every 0.5 second and, once converted to appropriate volumetric units, is used to update the volumetric flow display. Determining the mass flow rate using mass flow that has occurred during past and present 0.5 second intervals advantageously smooths variations in the displayed rate.

Specifically, upon entry into routine 1510, block 1511 executes to reset the pass counter, N, to the value "25". Thereafter, block 1513 is executed to read e current count stored within counter 630 into temporary memory location NEWCOUNTO. This count, in down-count form, represents mass flow that has occurred during the immediately preceding 0.5 second interval. Counter 630 is not reset during execution of this routine. The contents of this counter, that have just been read, are simply retained in memory and used as a base from which to subtract the value read from the counter during the next iteration through this routine in order to obtain the incremental count, in upcount form. As such, the contents in this counter are allowed to wrap around. Specifically, block 515 is executed which calculates the proper mass flow, in upcount form, that has occurred during this 0.5 second interval by subtracting the downcount value of NEWCOUNTO from OLDCOUNTO, the latter holding the totalized mass flow that has occurred during the preceding half second. Thereafter, execution passes to block 1517 which adds the upcount totalized mass flow that has occurred during the present 0.5 second interval (OLDCOUNTO) to that which has occurred during the immediately prior 0.5 second interval (RATE) to yield a direct value of the current mass flow rate (RATE). Once these operations have occurred, execution passes to decision block 1519 which determines whether this mass flow rate will be converted to appropriate volumetric units for display or will be directly displayed as the mass flow rate for the entire emulsion. In the event a mass mode display has not been selected by the user, then execution passes, via the NO path from decision block 1519, to block 1522. This block, when executed, multiplies the mass flow rate by the mass to volume conversion factor, MASS CONVERT, that has been previously calculated by densimeter processor 50 (see FIG. 5 and specifically FIG. 10) and serially transmitted to DRT 60 and stored there in NOVRAM. The result is the volumetric flow rate for the entire emulsion, E VOL R. Execution now passes to decision block 1524 to select whether the volumetric flow rate for the entire oil-water emulsion (emulsion mode) is to be displayed If the entire emulsion has not been selected, then decision block 1527 is executed. This decision block selects the volumetric flow rate for either the oil or water component. If the oil component has been selected (oil mode), then execution proceeds to block 1530 which, when executed, multiplies the volumetric flow rate of the entire emulsion by the oil cut density ratio, $DR_{oil}$, to yield the volumetric flow rate for the oil component alone, OIL VOL R. As discussed above, this density factor has been previously calculated by densimeter processor 50 (see FIG. 5 and specifically FIG. 11A–11C) and serially transmitted to DRT 60 and stored there in NOVRAM. Alternatively, if the water component has been selected (water mode), then execution proceeds, via NO path 1528 from decision b-lock 1527, to block 1532. This block, when executed, multiplies the volumetric flow rate for the entire emulsion by the water cut density ratio $DR_{water}$, to yield the volumetric flow rate for the water component alone, W VOL R. As previously discussed, this ratio was also calculated by densimeter processor 50, serially transmitted to DRT 60 and stored there in NOVRAM. Execution now proceeds to decision block 1534 from: YES path 1520 of decision block 1519 (indicating that mass mode has been selected), from YES path 1525 of decision block 1524 (indicating that the volumetric flow rate for the entire emulsion is to be displayed), or from block 1530 or 1532 (indicating that the volumetric flow rate for the oil or water component, respectively, is to be displayed).

If the mass mode has been selected. Decision block 1534 routes execution to block 1536 which sets the display variable, RDISPLAY, to the value of RATE (the current mass flow rate of the entire emulsion). If the mass mode has not been selected, execution passes to decision block 1539. If the emulsion mode has been selected, then execution proceeds, via the YES path from decision block 1539, to block 1541. This latter block sets the display variable to the value of E VOL R (the volumetric flow rate for the entire emulsion). If the emulsion mode has not been selected, then execution passes, via the NO path from decision block 1539, to decision block 1542. If the oil mode has been selected by the user, then execution proceeds, via the YES path from decision block 1542, to block 1544 Which sets the value of the display variable equal to the value of OIL VOL R (the volumetric flow rate for the oil component). In the event the water mode has been selected, then execution passes, via the NO path from decision block 1542, to block 1546. This latter block, when executed, sets the display variable equal to the value W VOL R (the volumetric flow rate for the water component). Once any of blocks 1536, 1541, 1544 or 1546 is executed, block 1548 is executed Block 1548 converts the value of the display variable, RDISPLAY, to binary coded decimal (BCD) form for subsequent display by block 1550 as the current flow rate appearing on displays 685. Now, to save the downcount mass flow value and upcount mass flow rate value that just occurred during the present 0.5 second interval for use during the next 0.5 second interval block 1552, is executed to appropriately set the value of RATE and OLDCOUNT0 to the values of OLDCOUNT0 and NEWCOUNT0, respectively. This concludes execution of ½ second displayed rate update routine 1510.

As noted, totalizer and display routine 1560 is executed at 0.5 second intervals at the completion of routine 1510 and at every 20 millisecond interval therebetween, via NO path 1507 emanating from decision block 1506. As noted, this routine: calculates the volumetric flow that has occurred during the preceding 20 millisecond interval for the entire emulsion and for the water and oil components; separately and continually totalizes these three volumetric flow values and, lastly, displays whichever one of these three totalized volumetric flow values has been selected by the user.

Figure 15B:
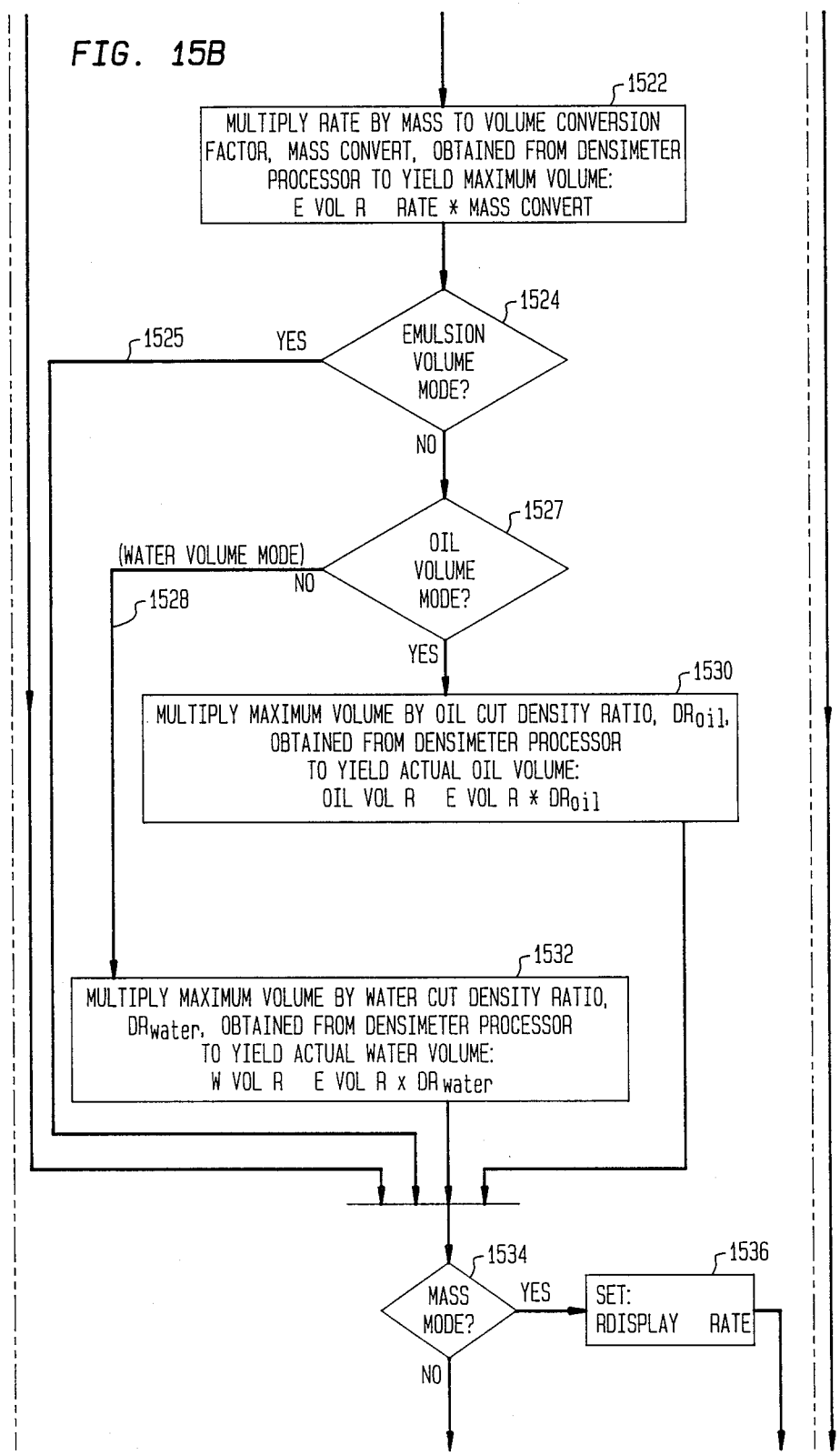
Figure 15C:
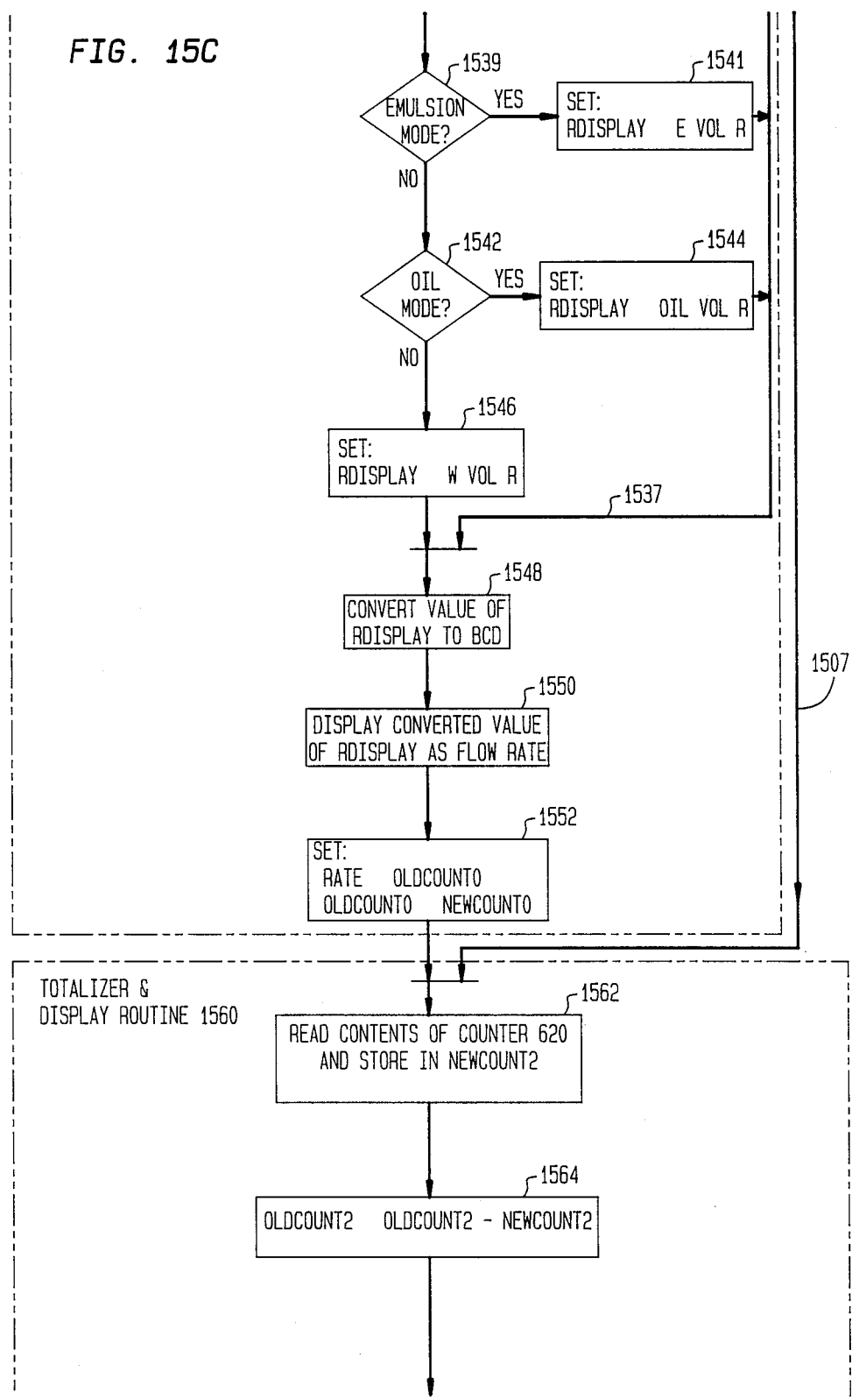
Figure 15D:
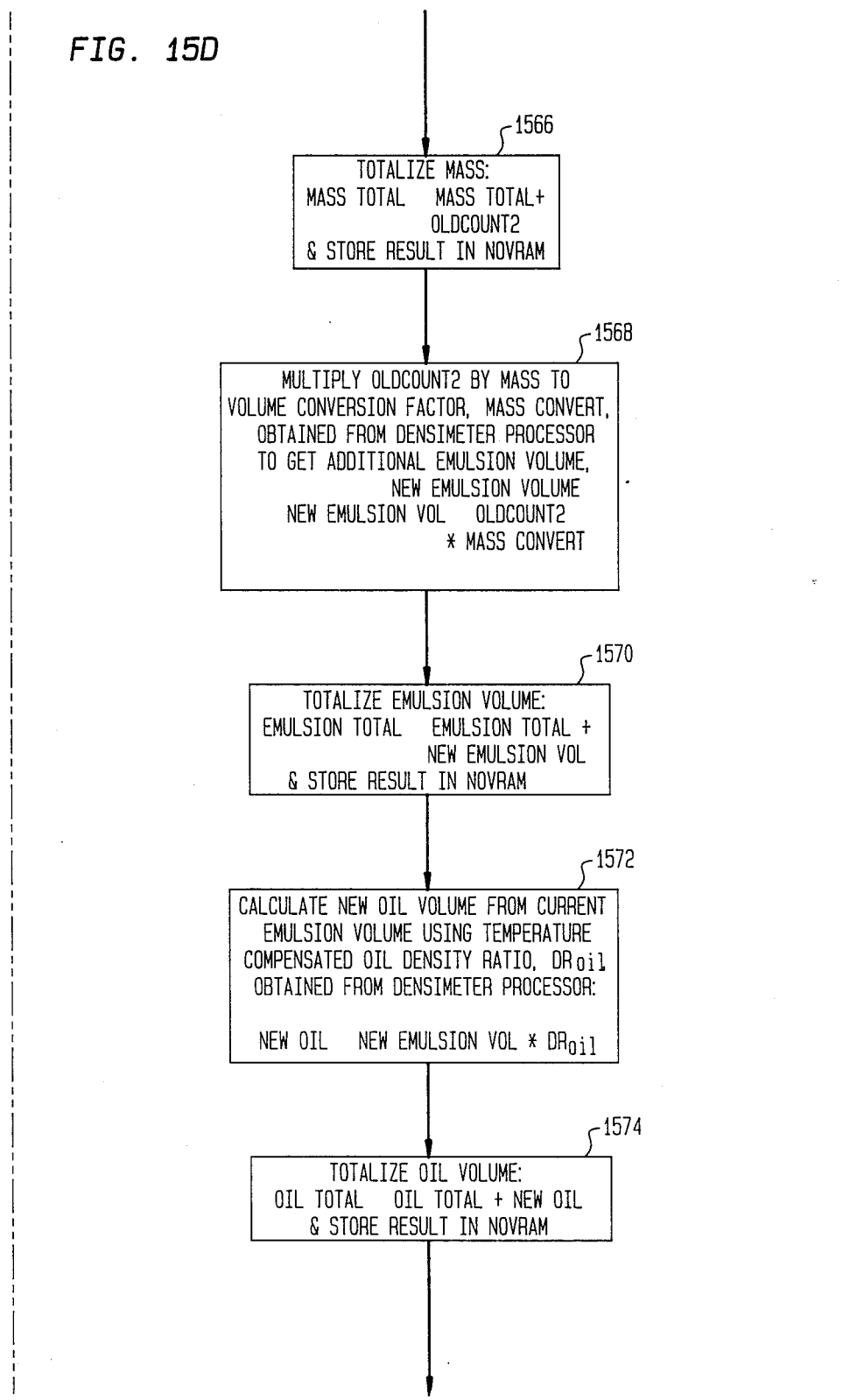
Figure 15E:
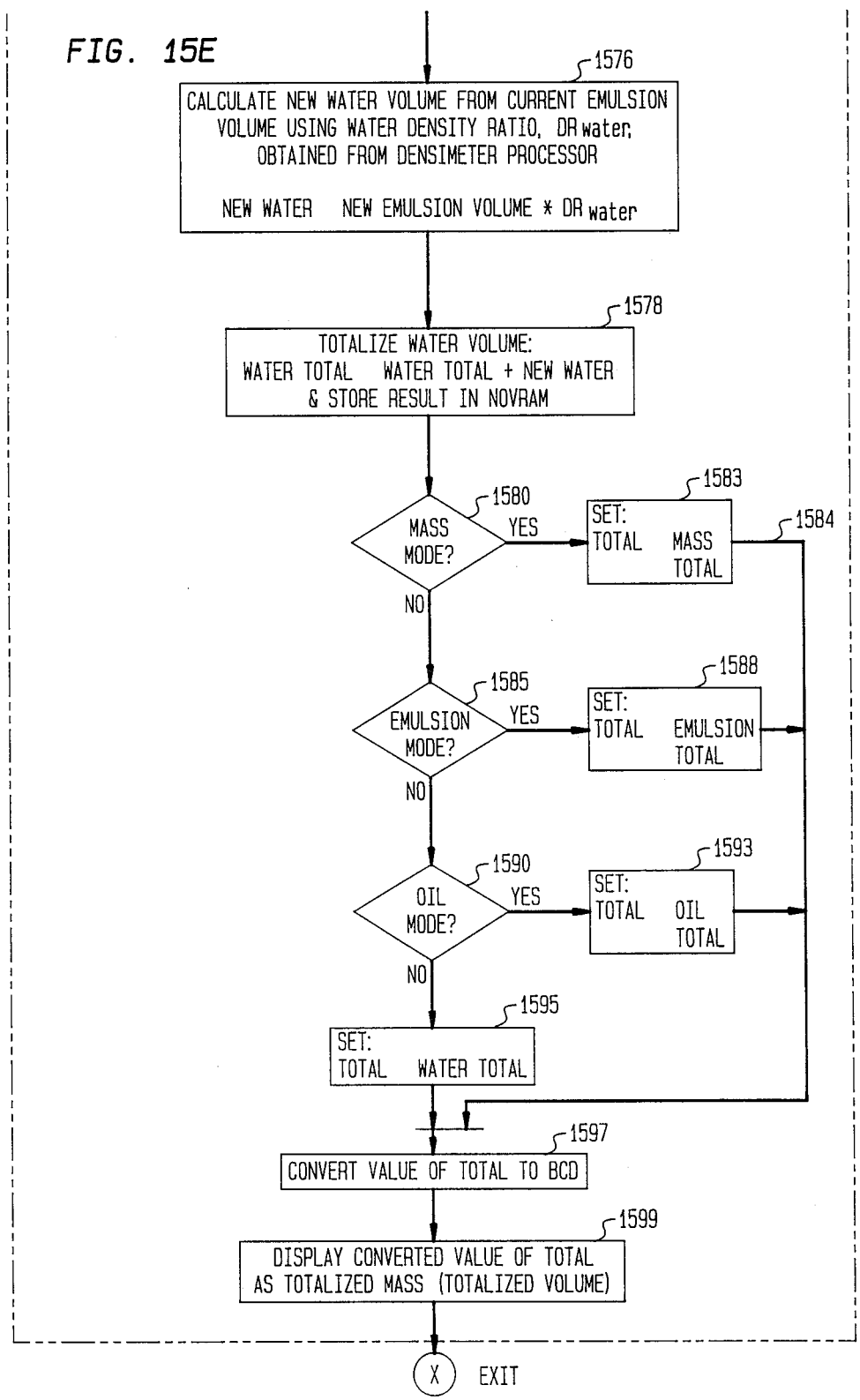

Execution of this routine begins with block 1562. This block, when executed., causes the microprocessor to read the count stored within counter 620, which totalizes the prescaled flow pulses produced by counter 625 (see FIG. 6) during the preceding 20 millisecond interval. As shown in FIG. 15C, this count is then stored in temporary memory location NEWCOUNT2. This counter is not reset during execution of this routine. The contents of this counter, that have just been read, are simply retained in memory and used as a base from which to subtract the value read from the counter during the next iteration through this routine in order to obtain the incremental count, in upcount form. As such, the contents in this counter are allowed to wrap around. Specifically, execution passes to block 1564 which provides a totalized upcount value, OLDCOUNT2, of prescaled mass flow pulses by subtracting the value of NEWCOUNT2, which is in downcount form, from the present value OLDCOUNT2 and storing the result in OLDCOUNT2. Once this has occurred, execution passes to block 1566 which calculates totalized mass flow by adding OLDCOUNT2 to the present value of totalized mass flow, MASS TOTAL, and storing the result back into MASS TOTAL, the value of which is then stored back into NOVRAM.

Now, at this point, block 1568 is executed to calculate and totalize the volumetric flow of the entire oil-water emulsion, NEW EMULSION VOL, that occurred during the preceding 20 millisecond interval. To do so, the microprocessor first reads the value of the mass to volume conversion factor, MASS CONVERT, from NOVRAM. As discussed above, this factor was previously calculated by densimeter processor 50, serially transmitted to DRT 60 and then stored within the NOVRAM existing within the DRT. Thereafter, the value of OLDCOUNT2, which represents the mass flow that occurred during the preceding 20 millisecond interval, is multiplied by MASS CONVERT to yield a volumetric measure of the entire emulsion, NEW EMULSION VOL, that flowed during the preceding 20 millisecond interval. Thereafter, block 1570 is executed to totalize the emulsion volume, by adding the value of NEW EMULSION VOL to the present totalized volumetric measure of the emulsion, EMULSION TOTAL. The result is an updated value of EMULSION TOTAL which is itself stored back into NOVRAM.

Now, having determined the volumetric measure of the emulsion that flowed during the preceding 20 millisecond interval, NEW EMULSION VOL, this value can be used to calculate and totalize the volumetric measures of the individual oil and water components present in the emulsion. Specifically, execution first passes to block 1572. This block when executed, accesses the oil cut density ratio $DR_{oil}$, from NOVRAM. As discussed above, the value of this ratio was previously calculated by densimeter processor 50, as discussed above, serially transmitted to DRT 60 and stored there in NOVRAM. The value of $DR_{oil}$ is then multiplied by the value of the emulsion volume NEW EMULSION VOL to yield a volumetric measure of the oil component, NEW OIL, that occurred during the preceding 20 millisecond interval. Block 1574 is then executed to totalize the volumetric oil volume by adding the value of NEW OIL to the present totalized volumetric value for oil, OIL TOTAL. The result is an updated value for OIL TOTAL which is then stored in NOVRAM. To calculate the volumetric measure of water, execution proceeds to block 1576. This block, when executed, first accesses the value of the water cut density ratio, $DR_{water}$. As with $DR_{oil}$, the value of $DR_{water}$ has been previously calculated by densimeter processor 50, serially transmitted to DRT 60 and stored there in NOVRAM. Once the value of $DR_{water}$ has been accessed, block 1576 multiplies this value by the value of the emulsion volume, NEW EMULSION VOL, to yield a volumetric measure of water, NEW WATER. Block 1578 is then executed to totalize the volumetric water value by adding the value of NEW WATER to the present totalized volumetric value for water, WATER TOTAL. The result is an updated value for WATER TOTAL which is then stored in NOVRAM.

At this point, since all the volumetric values have been totalized, execution passes to a sequence of blocks to select one of the volumetric flow measures and corresponding totalized flow values for display. Specifically, execution passes to decision block 1580 which, if mass mode has been selected by a user, transfers execution, via its YES path, to execution block 1583. This latter block sets the value of a display variable, TOTAL, equal to the value of the totalized mass flow, i.e. MASS TOTAL. If the mass mode has not been selected, then execution proceeds, via the NO path from decision block 1580, to decision block 1585. In the event the user has selected the emulsion mode, then execution passes via the YES path from decision block 1585 to execution block 1588. This latter block, when executed, sets the value of the display variable, TOTAL, to the value of the totalized volumetric flow of the entire oil-water emulsion, i.e. EMULSION TOTAL. If, however, the user has not selected the emulsion mode, then execution proceeds, via the NO path from decision block 1585 to decision block 15 90 to select either the totalized volumetric flow for oil or water. Specifically, if the user has selected the oil mode, then execution passes, via the YES path from decision block 1590 to execution block 1593. Here, this block, when executed, sets the value of the display variable, TOTAL, equal to the value of the totalized volumetric oil flow, i.e. OIL TOTAL. If the oil mode has not been selected, then execution proceeds, via the NO path from decision block 1590 to execution block 1595 which, when executed, sets the value of the display variable, TOTAL, equal to the totalized volumetric water flow, i.e. WATER TOTAL. After block 1583, 1588, 1593 or 1595 has been executed, block 1597 executes. Block 1597 converts the value of the display variable, TOTAL, from binary to BCD form for subsequent display by block 1599 as the current value Of totalized flow appearing on displays 685. Once block 1599 has fed the appropriate information to display controller 680, execution exits from DRT and display routine 1500 and once again returns to main program 1300 (see FIG. 13).

Clearly, as noted, DRT 60 could easily provide mass flow measurements of the individual oil and water components in the emulsion in addition to volumetric measurements of each component. To provide this function, the following equation would be used to provide a mass based water cut $WC_m$, and a mass based oil cut, $OC_m$, which here would equal the proportionate amount of the total mass flow of the emulsion attributable to the mass flow of water and oil components, respectively:

$$WC_m = \frac{(\text{rho}_{t\ water})_H [d_m - (\text{rho}_{t\ oil})_H]}{d_m [(\text{rho}_{t\ water})_H - (\text{rho}_{t\ oil})_H]} \quad (27)$$

$$OC_m = 1 - WC_m \quad (28)$$

The mass flow rate and totalized mass flow values would then merely be multiplied by the value of the mass based water cut and the mass based oil cut to yield the individual mass flow rate and totalized mass flow of the water and oil components, respectively, that are present in the emulsion. By performing separate calculations within DRT 60 using the volumetric based water and oil cut density ratios (equations 20 and 21), and mass based water and oil cuts (equations 27 and 28), both volumetric and mass measurements of flow rate and totalized flow may be advantageously and simultaneously obtained. Consequently, whenever the inventive system would be used as a net oil computer, the system could easily provide both volumetric and mass based measurements.

Additionally, as described above, the densimeter is calibrated by taking tube period and temperature measurements on two fluids, with known densities, that are successively passed through the meter. Although the preferred embodiment utilizes air and water, preferably in this sequence, for these two fluids any other fluids may be used instead as long as their density values as a function of temperature are known.

Furthermore, although digital rate totalizer and display 60 has been described in terms of providing volumetric and mass measurements of oil and water components in an oil-water flow stream, DRT 60 could easily be adapted to provide volumetric and mass measurements of any two immiscible components in a flowing emulsion. Once the value of a reference density of each component is known and entered into the system by the user, the calculations would proceed in essentially the manner as set forth above. However, for an emulsion other than a crude oil-saltwater emulsion, different formulas, other than those described above, would be used to characterize the physical characteristics of the entire emulsion and each specific component appearing therein. For example, different formulas would be used for compensating the reference density value of each component for temperature variations, and for calculating the density ratios of each component and the mass to volume conversion factor of the total emulsion. The inventive system could be expanded to provide volumetric and mass based flow measurements of multiphase emulsions having more than two immiscible components. In this case, 20 msec interrupt routine 1500 would be modified to calculate a..n additional density ratio and perform appropriate volumetric and mass low totalization for each additional component in the emulsion.

Moreover, although the disclosed embodiment utilizes U-shaped flow tubes, flow tubes of almost any size and shape may be used as long as the tubes can be oscillated about an axis to establish a non-inertial frame of reference. For example, these tubes may include but are not limited to straight tubes, S-shaped tubes or looped tubes. Moreover, although the meter has been shown as containing only two parallel flow tubes, more than two parallel flow tubes—such as three, four or even more—may be used if desired. Furthermore, although the flow tubes have been described as being constructed from a material having a linear spring constant (such as 316L stainless steel), the flow tubes could alternatively be fabricated from a material having a non-linear spring constant as long as the spring constant can be accurately characterized as being linear throughout the range of movement in which the flow tubes are vibrated.

Although a particular embodiment of the present invention has been shown and described herein, many varied embodiments incorporating the teachings of the present invention may be easily constructed by those skilled in the art.

I claim:

1. Apparatus for a flow metering system using a Coriolis meter having at least one flow tube which is driven to resonantly oscillate in a substantially sinusoidal manner about a bending axis while an emulsion formed of at least two substantially immiscible components flows through said flow tube, said apparatus comprising:

a flow rate measuring circuit comprising:

means for sensing a time interval occurring between a first point in time at which one side leg of said flow tube reaches a pre-defined point in its travel and a second point in time at which a second side leg of said flow tube and counterpart to said first side leg reaches a corresponding pre-defined point in its travel, whereby the duration of this interval is proportional to both Coriolis forces induced by movement of a given fluid flowing through said flow tube and to flow rate of said given fluid flowing through said flow tube; and means, responsive to said sensed time interval, for producing a stream of flow rate pulses having a frequency proportional to the flow rate of said given fluid; and a first circuit comprising:

means for measuring a value of a period at which said flow tube resonantly vibrates while the given fluid flows therethrough and for generating a first interrupt at the conclusion of each period value measurement;

means for measuring a temperature of said flow tube;

first means for displaying a value of density of said given fluid; and a first processing circuit comprising:

means, responsive to an occurrence of said first interrupt, for filtering said period value measurement to yield a filtered period measurement;

means for generating a second interrupt at a first pre-defined periodic interval of time;

means, operative in response to an occurrence of said second interrupt and to said temperature measuring means, for providing a measured temperature value of said flow tube coincidentally occurring while said given fluid flows therethrough;

means for determining, in response to the measured temperature value, a temperature coefficient value for said given fluid;

means, responsive to said temperature coefficient determining means and to said filtered period measurement, for determining a first factor as being a product of said temperature coefficient value and a square of said period value;

means, responsive to said first factor and to second and third factors associated with first and second known calibration fluids, for producing a current density value of said given fluid;

means, responsive to said current density value, for updating the displayed density value appearing on said first displaying means with said current density value at a second pre-defined periodic interval of time, wherein said second pre-defined interval is longer than said first pre-defined interval;

means for compensating corresponding first and second reference density values for first and second immiscible components present in said emulsion to the measured temperature value in order to yield corresponding first and second temperature compensated density values;

means, responsive to said current density value, and to said first and second temperature compensated density values, for generating corresponding first and second density ratios of the first and second immiscible components that are present within said given emulsion; and means for applying said first and second density ratios to a second circuit; and a second circuit, operative in response to said first and second density ratios and said flow rate pulses, comprising:

means for totalizing the flow rate pulses to produce a totalized flow value;

means for receiving said first and second density ratios from said first circuit to generate corresponding first and second received density ratios and, in response thereto, for generating a third interrupt;

second means for displaying either a corresponding flow rate of said emulsion, said first or said second immiscible components or corresponding totalized values of the flow of said emulsion or said first or said second immiscible components;

a second processing circuit comprising:

means, operative in response to said receiving and generating means, for storing the first and second received density ratios, at an occurrence of said third interrupt, in appropriate memory locations in order to provide corresponding stored first and second density ratios;

means for generating a fourth interrupt at a third pre-defined periodic interval of time;

means, responsive to the occurrence of said fourth interrupt, for converting the totalized flow value that occurs over a fourth periodic interval of time into a current flow rate value; wherein said fourth interval is longer than said third interval;

means, responsive to the stored first and second density ratios and to said totalized flow rate value occurring over said fourth interval, for generating corresponding current values of totalized flow for said emulsion and of said first and second components;

means, responsive to the corresponding current values of flow rate and totalized flow for said emulsion and said first and second components, for selectively updating a corresponding displayed value appearing on said second display means;

wherein said apparatus further comprises means for corresponding setting each of the second and third factors substantially equal to the first factor that occurs when the first and second known calibration fluids are correspondingly and selectively passed through the flow tube in order to calibrate the meter.

2. The apparatus in claim 1 wherein said flow tubes are U-shaped, straight, S-shaped or looped.

3. The apparatus in claim 2 wherein said first and second calibration fluids have corresponding first and second known density values, and wherein said second and third factor setting means comprises:
means for forming a first fractional value as being substantially equal to a difference between said second and third factors; and
means for forming a multiplicative factor as being substantially equal to a difference between the first and second known density values; and wherein said current density value producing means comprises:
means for forming a second fractional value as being substantially equal to a difference between said first factor and said second factor;
means for forming an intermediate density value as being a product of said multiplicative factor and said second fractional value divided by said first fractional value; and
means for setting said current density value, if said intermediate density value has a positive sign, substantially equal to a sum of said intermediate density value and said second known density value or, if said intermediate density value has a negative sign, substantially equal to an absolute value of a difference between the intermediate density value and the second known density value.

4. The apparatus in claim 3 wherein the first and second immiscible components are saltwater and crude oil, respectively.

5. The apparatus in claim 3 wherein said first and second calibration fluids are water and air, respectively.

6. The apparatus in claim 3 wherein said first processing circuit further comprises:
means, responsive to said current density value and a pre-defined constant, for determining a mass to volume conversion factor; and
means for applying said conversion factor to said second circuit; and wherein said second processing circuit further comprises:
means for determining volumetric flow and flow rate for said emulsion and for said first and second components present therein in response to said conversion factor, said stored first and second density ratios, said current emulsion flow rate and said totalized flow value for said emulsion; and
means, responsive to said volumetric flow and flow rate for said emulsion and for said first and second components, for selectively updating a corresponding displayed value appearing on said second display.

7. The apparatus in claim 6 wherein said second circuit value generating means comprises: means for separately totalizing the volumetric flow values for said first and second components and said emulsion so as to yield the corresponding current values of totalized volumetric flow of said first and second components and said emulsion.

8. The apparatus in claim 7 wherein the first and second immiscible components are saltwater and crude oil, respectively.

9. The apparatus in claim 7 wherein said first and second calibration fluids are water and air, respectively.

10. The apparatus in claim 3 wherein said second circuit current value generating means comprises: means for multiplying each of said stored first and second density ratios by the current value for the totalized flow of said emulsion to yield the corresponding current values of totalized mass flow for said first and second components.

11. The apparatus in claim 10 wherein said second circuit current value generating means further comprises: means for multiplying each of the stored first and second density ratios by the current value of the flow rate in order to yield corresponding mass flow rate values for the first and second components.

12. The apparatus in claim 11 wherein the first and second immiscible components are saltwater and crude oil, respectively.

13. The apparatus in claim 11 wherein said first and second calibration fluids are water and air, respectively.

14. Apparatus for a flow metering system which measures the flow of each of two substantially immiscible components in a flowing emulsion, said apparatus comprising:
a Coriolis meter assembly comprising:
first and second flow tubes;
inlet and outlet manifolds for respectively conducting a given fluid into and out of both of said flow tubes, wherein said inlet manifold divides the given fluid between both of said flow tubes and said outlet manifold combines the given fluid exiting from both of said flow tubes;
first and second mounting blocks, which receive corresponding ends of both of said flow tubes and are fixedly secured to said inlet and outlet manifolds, for respectively dividing the given fluid emanating from said inlet manifold and routing the divided given fluid into both of said flow tubes or combining the divided given fluid emanating from both of said flow tubes and routing the combined given fluid into said outlet manifold;
means, responsive to a drive signal, for vibrating both of said flow tubes in an opposing sinusoidal pattern at a resonant frequency;
means for sensing movement of at least one of the flow tubes;
means, affixed to one of said flow tubes, for sensing temperature thereof; and
a flow rate measuring circuit comprising:
means, responsive to said movement sensing means, for sensing a time interval occurring between a first point in time at which one side leg of said flow tube reaches a pre-defined point in its travel and a second point in time at which a second side leg of said flow tube and counterpart to said first side leg reaches a corresponding pre-defined point in its travel, whereby the duration of this interval is proportional to both Coriolis forces induced by movement of the given fluid flowing through said flow tube and to flow rate of said given fluid flowing through said flow tube; and
means, responsive to said sensed time interval, for producing a stream of flow rate pulses having a frequency proportional to the flow rate of said given fluid; and a first circuit comprising:

means, responsive to said movement sensing means, for measuring a value of a period at which said flow tube resonantly vibrates while the given fluid flows therethrough and for generating a first interrupt at the conclusion of each period value measurement;

means, responsive to said temperature sensing means, for measuring a temperature of said flow tube;

first means for displaying a value of density of said given fluid; and a first processing circuit comprising:

means, responsive to an occurrence of said first interrupt, for filtering said period value measurement to yield a filtered period measurement;

means for generating a second interrupt at a first pre-defined periodic interval of time;

means, operative in response to an occurrence of said second interrupt and to said temperature measuring means, for providing a measured temperature value of said flow tube coincidentally occurring while said given fluid flows therethrough;

means, for determining, in response to the measured temperature value, a temperature coefficient value for said given fluid;

means, responsive to said temperature coefficient determining means and to said filtered period measurement, for determining a first factor as being a product of said temperature coefficient value and a square of said period value;

means, responsive to said first factor and to second and third factors associated with a first and second known calibration fluids, for producing a current density value of said given fluid;

means, responsive to said current density value, for updating the displayed density value appearing on said first displaying means with said current density value at a second pre-defined periodic interval of time, wherein said second pre-defined interval is longer than said first pre-defined interval;

means for compensating corresponding first and second reference density values for first and second immiscible components present in said emulsion to the measured temperature value in order to yield corresponding first and second temperature compensated density values;

means, responsive to said current density value, and to said first and second temperature compensated density values, for generating corresponding first and second density ratios of the first and second immiscible components that are present within said given emulsion; and means for applying said first and second density ratios to a second circuit; and a second circuit, operative in response to said first and second density ratios and said flow rate pulses, comprising:

means for totalizing the flow rate pulses to produce a totalized flow value;

means for receiving said first and second density ratios from said first circuit to generate corresponding first and second received density ratios and, in response thereto, for generating a third interrupt;

second means for displaying either a corresponding flow rate of said emulsion, said first or said second immiscible components or corresponding totalized values of the flow of said emulsion or said first or said second immiscible components;

a second processing circuit comprising:

means, operative in response to said receiving and generating means, for storing the first and second received density ratios, at an occurrence of said third interrupt, in appropriate memory locations in order to provide corresponding stored first and second density ratios;

means for generating a fourth interrupt at a third pre-defined periodic interval of time;

means, responsive to the occurrence of said fourth interrupt, for converting the totalized flow value that occurs over a fourth periodic interval of time into a current flow rate value, wherein said fourth interval is longer than said third interval;

means, responsive to the stored first and second density ratios and to said totalized flow value occurring over said fourth interval, for generating corresponding current values of totalized flow for said emulsion and for said first and second components;

means, responsive to the corresponding current values of flow rate and totalized flow for said emulsion and said first and second components, for selectively updating a corresponding displayed value appearing on said second display means;

wherein said apparatus further comprises means for corresponding setting each of the second and third factors substantially equal to the first factor that occurs when the first and second known calibration fluids are correspondingly and selectively passed through the flow tube in order to calibrate the meter.

15. The apparatus in claim 14 wherein said first and second calibration fluids have corresponding first and second known density values, and wherein said second and third factor setting means comprises:

means for forming a first fractional value as being substantially equal to a difference between said second and third factors; and means for forming a multiplication factor as being substantially equal to a difference between the first and second known density values; and wherein said current density value producing means comprises:

means for forming a second fractional value as being substantially equal to a difference between said first factor and said second factor;

means for forming an intermediate density value as being a product of said multiplicative factor and said second fractional value divided by said first fractional value; and means for setting said current density value, if said intermediate density value has a positive sign, substantially equal to a sum of said intermediate density value and said second known density value or, if said intermediate density value has a negative sign, substantially equal to an absolute value of a difference between the intermediate density value and the second known density value.

16. The apparatus in claim 15 wherein said first processing circuit further comprises:
   means, responsive to said current density value and a pre-defined constant, for determining a mass to volume conversion factor; and
   means for applying said conversion factor to said second circuit; and wherein said second processing circuit further comprises:
   means for determining volumetric flow and flow rate for said emulsion and for said first and second components present therein in response to said conversion factor, said stored first and second density ratios, said current emulsion flow rate and said totalized flow value for said emulsion; and
   means, responsive to said volumetric flow and flow rate for said emulsion and for said first and second components, for selectively updating a corresponding displayed value appearing on said second display.

17. The apparatus in claim 16 wherein said second circuit value generating means comprises: means for separately totalizing the volumetric flow values for said first and second components and said emulsion so as to yield the corresponding current values of totalized volumetric flow of said first and second components and said emulsion.

18. The apparatus in claim 17 wherein the first and second immiscible components are saltwater and crude oil, respectively.

19. The apparatus in claim 17 wherein said first and second calibration fluids are water and air, respectively.

20. The apparatus in claim 15 wherein said second circuit current value generating means comprises: means for multiplying each of said stored first and second density ratios by the current value for totalized flow of said emulsion to yield the corresponding current values of totalized mass flow for said first and second components.

21. The apparatus in claim 20 wherein said second circuit current value generating means further comprises: means for multiplying each of the stored first and second density ratios by the current value of the flow rate in order to yield corresponding mass flow rate values for the first and second components.

22. The apparatus in claim 21 wherein the first and second immiscible components are saltwater and crude oil, respectively.

23. The apparatus in claim 21 wherein said first and second calibration fluids are water and air, respectively.

24. Apparatus for a net oil computer which measures the flow of crude oil and saltwater in a flowing crude oil-saltwater emulsion, said apparatus comprising:
   a Coriolis meter assembly comprising:
      first and second flow tubes;
      inlet and outlet manifolds for respectively conducting a given fluid into and out of both of said flow tubes, wherein said inlet manifold divides the given fluid between both of said flow tubes and said outlet manifold combines the given fluid exiting from both of said flow tubes;
      first and second mounting blocks, which receive corresponding ends of both of said flow tubes and are fixedly secured to said inlet and outlet manifolds, for respectively dividing the given fluid emanating from said inlet manifold and routing the divided given fluid into both of said flow tubes or combining the divided given fluid emanating from both of said outlet manifold;
      means, responsive to a drive signal, for vibrating both of said flow tubes in an opposing sinusoidal pattern at a resonant frequency;
      means for sensing movement of at least one of the flow tubes;
      means, affixed to one of said flow tubes, for sensing temperature thereof; and
   a flow rate measuring circuit comprising:
      means, responsive to said movement sensing means, for sensing a time interval occurring between a first point in time at which one side leg of said flow tube reaches a pre-defined point in its travel and a second point in time at which a second side leg of said flow tube and counterpart to said first side leg reaches a corresponding pre-defined point in its travel, whereby the duration of this interval is proportional to both Coriolis forces induced by movement of the given fluid flowing through said flow tube and to flow rate of said given fluid flowing through said flow tube; and
      means, responsive to said sensed time interval, for producing a stream of mass flow rate pulses having a frequency proportional to the mass flow rate of said given fluid; and
   a first circuit comprising:
      means, responsive to said movement sensing means, for measuring a value of a period at which said flow tube resonantly vibrates while the given fluid flows therethrough and for generating a first interrupt at the conclusion of each period value measurement;
      means, responsive to said temperature sensing means, for measuring a temperature of said flow tube;
      first means for displaying a value of density of said given fluid; and
   a first processing circuit comprising:
      means, responsive to an occurrence of said first interrupt, for filtering said period value measurement to yield a filtered period measurement;
      means for generating a second interrupt at a first pre-defined periodic interval of time;
      means, operative in response to an occurrence of said second interrupt and to said temperature measuring means, for providing a measured temperature value of said flow tube coincidently occurring while said given fluid flows therethrough;
      means for determining, in response to the measured temperature value, a temperature coefficient value for said given fluid;
      means, responsive to said temperature coefficient determining means and to said filtered period measurement, for determining a first factor as being a product of said temperature coefficient value and a square of said period value;
      means, responsive to said first factor and to second and third factors associated with first and second known calibration fluids, for producing a current density value of said given fluid;
      means, responsive to said current density value, for updating the displayed density value appearing on said first displaying means with said current density value at a second pre-defined periodic interval of time, wherein said second pre-defined interval is longer than said first pre-defined interval;

means for compensating corresponding first and second reference density values for oil and saltwater to the measured temperature value in order to yield corresponding temperature compensated oil and saltwater density values;

means, responsive to said current density value, and to said temperature compensated oil and saltwater density values, for generating corresponding oil and saltwater density ratios of the oil and saltwater that are present within said given emulsion; and means for applying said oil and saltwater density ratios to a second circuit; and a second circuit, operative in response to said oil and saltwater density ratios and said mass flow rate pulses, comprising:

means for totalizing the mass flow rate pulses to produce a totalized mass flow value of said emulsion;

means for receiving said oil and saltwater density ratios from said first circuit to generate corresponding received oil and saltwater density ratios and, in response thereto, for generating a third interrupt;

second means for displaying either a corresponding flow rate of said emulsion, said oil or saltwater present therein or corresponding totalized values of the flow of said emulsion or said oil or saltwater;

a second processing circuit comprising:

means, operative in response to said receiving and generating means, for storing the received oil and saltwater density ratios, at an occurrence of said third interrupt, in appropriate memory locations in order to provide corresponding stored oil and saltwater density ratios;

means for generating a fourth interrupt at a third pre-defined periodic interval of time;

means, responsive to the occurrence of said fourth interrupt, for converting the totalized mass flow value of said emulsion that occurs over a fourth periodic interval of time into a current flow rate value for said emulsion wherein said fourth interval is longer than said third interval;

means, responsive to the stored oil and saltwater density ratios and to said totalized mass flow value occurring over said fourth interval, for generating corresponding current values of totalized mass flow for said emulsion and for said oil and saltwater;

means, responsive to the corresponding current values of mass flow rate and totalized mass flow for said emulsion and said oil and saltwater, for selectively updating a corresponding displayed value appearing on said second display means;

wherein said apparatus further comprises means for correspondingly setting each of the second and third factors substantially equal to the first factor that occurs when water and air as the first and second known calibration fluids are correspondingly and selectively passed through the flow tube in order to calibrate the meter.

25. The apparatus in claim 24 wherein said first and second calibration fluids have corresponding first and second known density values, and wherein said second and third factor setting means comprises:

means for forming a first fractional value as being substantially equal to a difference between said second and third factors; and means for forming a multiplication factor as being substantially equal to a difference between the first and second known density values; and wherein said current density value producing means comprises:

means for forming a second fractional value as being substantially equal to a difference between said first factor and said second factor;

means for forming an intermediate density value as being a product of said multiplicative factor and said second fractional value divided by said first fractional value; and means for setting said current density value, if said intermediate density value has a positive sign, substantially equal to a sum of said intermediate density value and said second known density value or, if said intermediate density value has a negative sign, substantially equal to an absolute value of a difference between the intermediate density value and the second known density value.

26. The apparatus in claim 25 wherein said first processing circuit further comprises:

means, responsive to said current density value and a pre-defined constant, for determining a mass to volume conversion factor; and means for applying said conversion factor to said second circuit; and wherein said second processing circuit further comprises:

means for determining volumetric flow and flow rate for said emulsion and for said first and second components present therein in response to said conversion factor, said stored first and second density ratios, said current emulsion flow rate and said totalized flow value for said emulsion; and means, responsive to said volumetric flow rate for said emulsion and for said first and second components, for selectively updating a corresponding displayed value appearing on said second display.

27. The apparatus in claim 26 wherein said second circuit value generating means comprises: means for separately totalizing the volumetric flow values for said first and second components and said emulsion so as to yield the corresponding current values of totalized volumetric flow of said first and second components and said emulsion.

28. The apparatus in claim 26 wherein said second circuit current value generating means comprises: means for multiplying each of said stored first and second density ratios by the current value for the totalized flow of said emulsion to yield the corresponding current values of totalized mass flow for said first and second components.

29. The apparatus in claim 28 wherein said second circuit current value generating means further comprises: means for multiplying each of the stored first and second density ratios by the current value of the flow rate in order to yield corresponding mass flow rate values for the first and second components.

30. In a flow metering system using a Coriolis meter having at least one flow tube which is driven to resonantly oscillate in a substantially sinusoidal manner about a bending axis while an emulsion formed of at least two substantially immiscible components flows through said flow tube, a method comprising the steps of:

in a flow rate measuring circuit:
  sensing a time interval occurring between a first point in time at which one side leg of said flow tube reaches a pre-defined point in its travel and a second point in time at which a second side leg of said flow tube and counterpart to said first side leg reaches a corresponding pre-defined point in its travel, whereby the duration of this interval is proportional to both Coriolis forces induced by movement of a given fluid flowing through said flow tube and to flow rate of said given fluid flowing through said flow tube; and
  producing, in response to said sensed time interval, a stream of flow rate pulses having a frequency proportional to the flow rate of said given fluid; and in a first circuit:
  measuring a value of a period at which said flow tube resonantly vibrates while the given fluid flows therethrough and for generating a first interrupt at the conclusion of each period value measurement;
  measuring a temperature of said flow tube;
  displaying a value of density of said given fluid on a first display; and in a first processing circuit:
  filtering, in response to an occurrence of said first interrupt, said period value measurement to yield a filtered period measurement;
  generating a second interrupt at a first pre-defined periodic interval of time;
  providing, in response to an occurrence of said second interrupt and to said temperature measuring means, a measured temperature value of said flow tube coincidentally occurring while said given fluid flows therethrough;
  determining, in response to the measured temperature value, a temperature coefficient value for said given fluid;
  determining, in response to said temperature coefficient determining means and to said filtered period measurement, a first factor as being a product of said temperature coefficient value and a square of said period value;
  producing, in response to said first factor and to second and third factors associated with first and second known calibration fluids, a current density value of said given fluid;
  updating, in response to said current density value, the displayed density value appearing on said first display with said current density value at a second pre-defined periodic interval of time, wherein said second pre-defined interval is longer than said first pre-defined interval;
  compensating corresponding first and second reference density values for first and second immiscible components present in said emulsion to the measured temperature value in order to yield corresponding first and second temperature compensated density values;
  generating, in response to said current density value, and to said first and second temperature compensated density values, corresponding first and second density ratios of the first and second immiscible components that are present within said given emulsion; and
  applying said first and second density ratios to a second circuit; and in a second circuit, operative in response to said first and second density ratios and said flow rate pulses:
  totalizing the flow rate pulses to produce a totalized flow value;
  receiving said first and second density ratios from said first circuit to generate corresponding first and second received density ratios and, in response thereto, for generating a third interrupt;
  displaying either a corresponding flow rate of said emulsion, said first or second immiscible components or corresponding totalized values of the flow of said emulsion or said first or said second immiscible components on a second display;

in a second processing circuit:
  storing, in response to said receiving and generating means, the first and second received density ratios, at an occurrence of said third interrupt, in appropriate memory locations in order to provide corresponding stored first and second density ratios;
  generating a fourth interrupt at a third pre-defined periodic interval of time;
  converting, in response to the occurrence of said fourth interrupt, the totalized flow value that occurs over a fourth periodic interval of time into a current flow rate value, wherein said fourth interval is longer than said third interval;
  generating, in response to the stored first and second density ratios and to said totalized flow value occurring over said fourth interval, corresponding current values of totalized flow for aid emulsion and for said first and second components;
  selectively updating, responsive to the corresponding current values of flow rate and totalized flow for said emulsion and said first and second components, a corresponding displayed value appearing on said second display;

wherein each of the second and third factors are set substantially equal to the first factor that occurs when the first and second known calibration fluids are correspondingly and selectively passed through the flow tube in order to calibrate the meter.

31. The method in claim 30 wherein said first and second calibration fluids have corresponding first and second known density values, and wherein said second and third factor setting step comprises the steps of:
  forming a first fractional value as being substantially equal to a difference between said second and third factors; and
  forming a multiplicative factor as being substantially equal to a difference between the first and second known density values; and wherein said current density value producing means comprises:
  forming a second fractional value as being substantially equal to a difference between said first factor and said second factor;
  forming an intermediate density value as being a product of said multiplicative factor and said second fractional value divided by said first fractional value; and setting said current density value, if said intermediate density value has a positive sign, substantially equal to a sum of said intermediate density value and said second known density value or, if said intermediate density value has a negative sign, substantially equal to an absolute value of a difference between the intermediate density value and the second known density value.

32. The method in claim 31 wherein the first and second immiscible components are saltwater and crude oil, respectively.

33. The method in claim 31 wherein in said first processing circuit:
    determining, in response to said current density value and a pre-defined constant, a mass to volume conversion factor; and
    applying said conversion factor to said second circuit; and
in said second processing circuit:
    determining volumetric flow and flow rate for said emulsion and for said first and second components present therein in response to said conversion factor, said stored first and second density ratios, said current emulsion flow rate and said totalized flow value for said emulsion; and
    selectively updating, in response to said volumetric flow and flow rate for said emulsion and for said first and second components, a corresponding displayed value appearing on said second display.

34. The method in claim 33 wherein said second circuit value generating step comprises: separately totalizing the volumetric flow values for said first and second components and said emulsion so as to yield the corresponding current values of totalized volumetric flow of said first and second components and said emulsion.

35. The method in claim 31 wherein said second circuit current value generating step comprises the step of: multiplying each of said stored first and second density ratios by the current value for the totalized flow of said emulsion to yield the corresponding current values of totalized mass flow for said first and second components.

36. The method in claim 35 wherein said second circuit current value generating step comprises the step of: multiplying each of the stored first and second density ratios by the current value of the flow rate in order to yield corresponding mass flow rate values for the first and second components.

* * * * *